(12) United States Patent
Hartley et al.

(10) Patent No.: US 12,004,707 B2
(45) Date of Patent: Jun. 11, 2024

(54) AIRWAY VISUALIZATION SYSTEM

(71) Applicant: The Board of Trustees of The Leland Stanford Junior University, Stanford, CA (US)

(72) Inventors: Bryan I. Hartley, Redwood City, CA (US); Norbert Pelc, Los Altos, CA (US); Dimitri Augustin, Los Altos, CA (US); Racquel Redwood, Sunnyvale, CA (US); Zach Wolf, Redwood City, CA (US); Benjamin Berkowitz, Palo Alto, CA (US); Harmeet Bedi, Los Altos, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 920 days.

(21) Appl. No.: 16/998,278

(22) Filed: Aug. 20, 2020

(65) Prior Publication Data

US 2020/0375448 A1    Dec. 3, 2020

Related U.S. Application Data

(63) Continuation of application No. PCT/US2019/027949, filed on Apr. 17, 2019.
(Continued)

(51) Int. Cl.
*A61B 5/00* (2006.01)
*A61B 1/00* (2006.01)
(Continued)

(52) U.S. Cl.
CPC ........ *A61B 1/2676* (2013.01); *A61B 1/00082* (2013.01); *A61B 1/015* (2013.01);
(Continued)

(58) Field of Classification Search
CPC ... A61B 1/2676; A61B 1/00082; A61B 1/015; A61B 6/12; A61B 6/487; A61B 6/50; A61B 6/541
See application file for complete search history.

(56) References Cited

U.S. PATENT DOCUMENTS 5,271,401 A * 12/1993 Fishman ............... A61B 6/481
424/9.4
5,549,119 A    8/1996 Solar
(Continued)

FOREIGN PATENT DOCUMENTS

WO   WO 2010/005575   1/2010
WO   WO 2012/106260   8/2012
WO   WO 2019/204499   10/2019

OTHER PUBLICATIONS

Shaw et al. "Endobronchial ultrasound to assess airway wall thickening: validation in vitro and in vivo" European Respiratory Journal, vol. 23, 2004, pp. 814-817.

*Primary Examiner* — Joel F Brutus
(74) *Attorney, Agent, or Firm* — Levine Bagade Han LLP

(57) ABSTRACT

An airway visualization system is described herein having an elongate delivery sheath and defining at least one lumen therethrough, wherein the length is positionable within an airway of a subject. An isolation component positioned near or at a distal end of the elongate delivery sheath is expandable to at least partially obstruct the airway and a controller is in communication with the delivery sheath. The controller is also configured to manipulate a fluid flow through the at least one lumen whereby a pressure change within the airway of the subject is imparted sufficiently to at least partially expand or collapse the airway to alter the density of the airway.

83 Claims, 47 Drawing Sheets

Related U.S. Application Data

(60) Provisional application No. 62/737,793, filed on Sep. 27, 2018, provisional application No. 62/659,032, filed on Apr. 17, 2018.

(51) Int. Cl.
*A61B 1/015* (2006.01)
*A61B 1/267* (2006.01)
*A61B 6/00* (2006.01)
*A61B 6/12* (2006.01)
*A61B 6/50* (2024.01)

(52) U.S. Cl.
CPC ............... *A61B 6/12* (2013.01); *A61B 6/487* (2013.01); *A61B 6/50* (2013.01); *A61B 6/541* (2013.01); *A61B 2562/0247* (2013.01)

(56) References Cited

U.S. PATENT DOCUMENTS

| | | |
|---|---|---|
| 6,398,775 B1 | 6/2002 | Perkins et al. |
| 6,411,852 B1 | 6/2002 | Danek et al. |
| 7,100,616 B2 | 9/2006 | Springmeyer |
| 7,130,457 B2 | 10/2006 | Kaufman et al. |
| 7,343,195 B2 | 3/2008 | Strommer et al. |
| 7,458,963 B2 | 12/2008 | Perkins et al. |
| 9,107,606 B2 | 8/2015 | Radhakrishnan et al. |
| 9,526,424 B2 | 12/2016 | Judell et al. |
| 9,545,497 B2 | 1/2017 | Wenderow et al. |
| 9,782,148 B2 | 10/2017 | Waters et al. |
| 2002/0077593 A1 | 6/2002 | Perkins et al. |
| 2003/0055331 A1 | 3/2003 | Kotmel et al. |
| 2004/0143251 A1 | 7/2004 | Sampson et al. |
| 2005/0187464 A1 | 8/2005 | Ho et al. |
| 2006/0100666 A1* | 5/2006 | Wilkinson ............ A61B 5/085 607/1 |
| 2009/0209906 A1* | 8/2009 | Tanaka .................. A61M 13/00 604/93.01 |
| 2010/0161023 A1 | 6/2010 | Cohen et al. |
| 2011/0074943 A1* | 3/2011 | Modell ................ H04N 25/531 348/E7.085 |
| 2011/0245665 A1 | 10/2011 | Nentwick |
| 2012/0158047 A1 | 6/2012 | Edwards et al. |
| 2013/0035434 A1* | 2/2013 | Wilson, III ............... C08L 9/00 524/517 |
| 2013/0103059 A1 | 4/2013 | Mathis et al. |
| 2013/0281885 A1 | 10/2013 | Rowbottom et al. |
| 2013/0296751 A1* | 11/2013 | Martin ............... A63B 21/0085 601/148 |
| 2014/0276173 A1* | 9/2014 | Banner ............. A61M 16/0434 600/533 |
| 2014/0303665 A1 | 10/2014 | Gerrans et al. |
| 2014/0366874 A1 | 12/2014 | Deutsch et al. |
| 2016/0184013 A1* | 6/2016 | Brannan ................ A61B 18/14 600/424 |
| 2016/0249860 A1 | 9/2016 | Kotmel et al. |
| 2016/0256646 A1 | 9/2016 | Vazales |
| 2016/0367747 A1 | 12/2016 | Loske |
| 2017/0143289 A1 | 5/2017 | Fouras |
| 2018/0049693 A1 | 2/2018 | Krimsky |

* cited by examiner

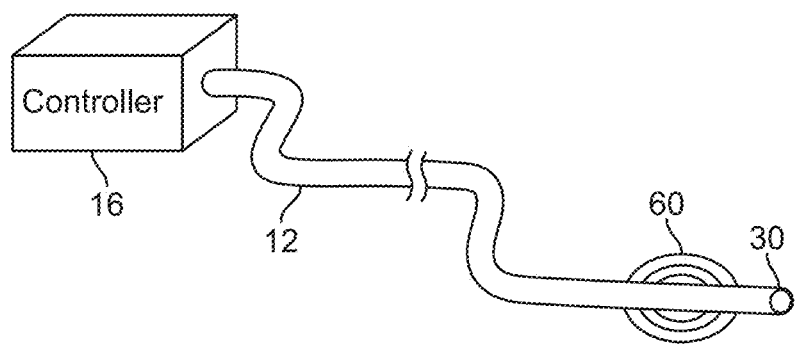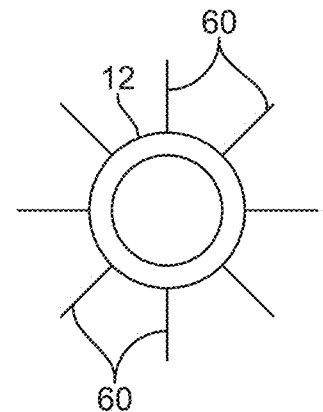
FIG. 5A  FIG. 5B
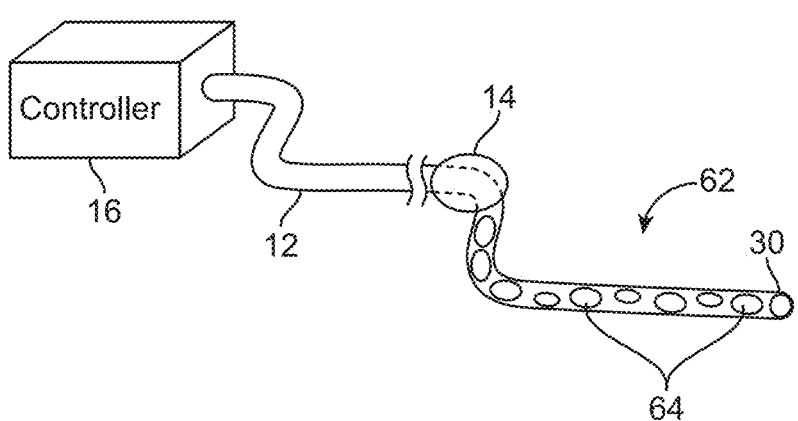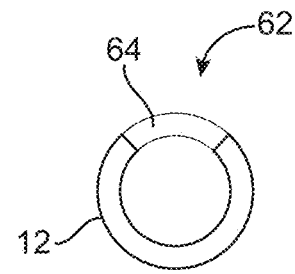
FIG. 6A  FIG. 6B

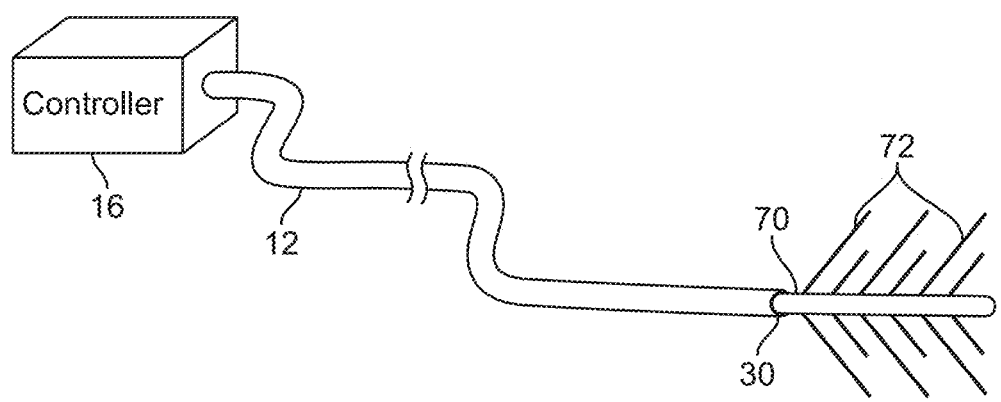
FIG. 7
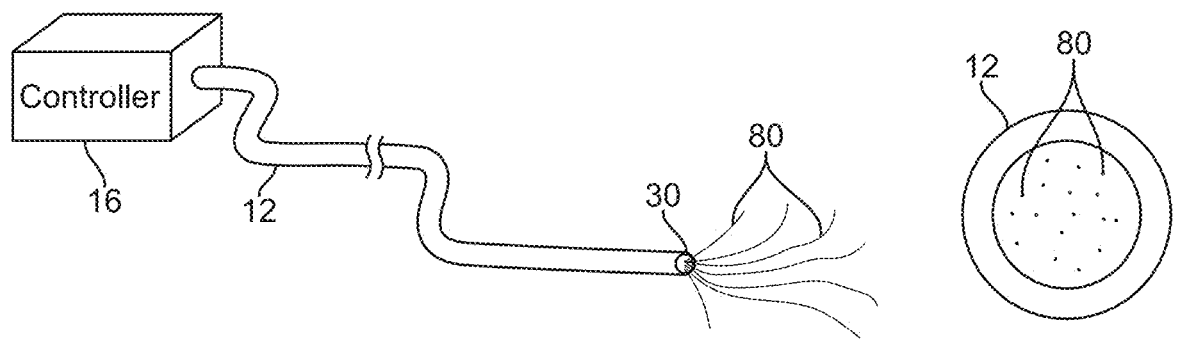
FIG. 8A
FIG. 8B

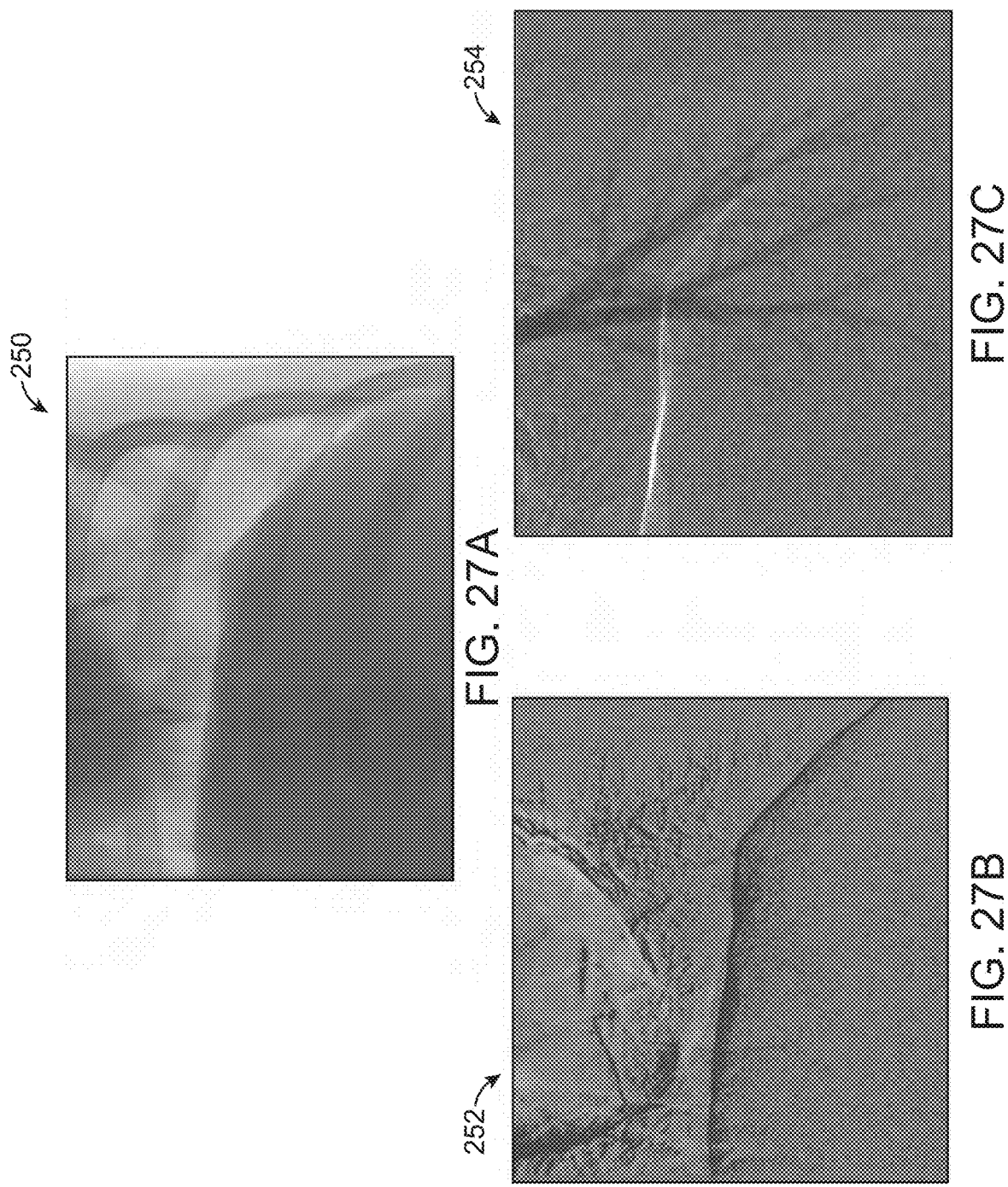

AIRWAY VISUALIZATION SYSTEM

CROSS-REFERENCE TO RELATED APPLICATIONS

This application is a continuation of International App. No. PCT/US2019/027949 filed Apr. 17, 2019, which claims the benefit of priority to U.S. Prov. Apps. 62/659,032 filed Apr. 17, 2018 and 62/737,793 filed Sep. 27, 2018, each of which is incorporated herein by reference in its entirety.

FIELD OF THE INVENTION

This application relates generally to medical devices and methods. More particularly, the application relates to systems and methods for visualizing airways and other structures in the lungs including pathologic structures (e.g. lung nodules), for example, to facilitate lung biopsies.

BACKGROUND OF THE INVENTION

Early diagnosis and treatment are vital for improving lung cancer survival rates. To diagnose lung cancer, most often some form of imaging (CT, chest X-ray) is performed to look for any abnormal growths in the lungs (called pulmonary nodules). Once found, a lung biopsy is performed, where a doctor removes a piece of tissue from the nodule, to determine if the growth is benign or malignant. In one technique to obtain tissue from the nodule, the biopsy is taken by advancing an endoscope (called a bronchoscope when used in the lung) through the mouth and into the lung, and then removing tissue through the bronchoscope working channel (open channel within the center of the bronchoscope through which tools can be placed into the lung). Because the lung contains around 1,500 miles of continuously branching airways, it can be challenging to navigate the bronchoscope to the correct part of the lungs to take a biopsy from the growth. Interestingly, in the blood vessels, accurate navigation is accomplished by using a liquid iodinated contrast material which can easily be seen on x-ray. Unfortunately, iodinated contrast cannot be used safely in the lungs as it can often lead to lung failure.

However, in the lung, multiple imaging techniques are used to increase the likelihood of reaching the nodule. Techniques include x-rays (fluoroscopic, or continuous x-ray), ultrasound, and electromagnetic navigation bronchoscopy (ENB). Ultrasound is limited, because sound waves cannot see into air-filled lung tissue. Fluoroscopic x-ray is suboptimal because the airways are not naturally of a density to be visible on x-ray. In blood vessels, this problem is solved by using iodinated contrast with fluoroscopic x-ray imaging. In addition, x-ray subtraction processing is often used to software-enhance the density change from the injection of iodinated contrast, which subtracts the pixel values of the first x-ray image from the pixel values of subsequent images. Subtraction processing is thus helpful to highlight and enhance a density change such as iodinated contrast injection on fluoroscopic x-ray imaging. Unfortunately, iodinated contrast media and most other substances that can be seen on x-ray (e.g. are dense enough to be detected) are not safe for use in the lungs, causing severe lung injury and even death. Electromagnetic navigation bronchoscopy (ENB) is used by many physicians to try to overcome these shortcomings. However, ENB is not real-time but instead uses an old CT scan to generate a virtual "roadmap" of the airways. This virtual roadmap can lead to localization errors of greater than 2 cm, due to normal breathing movement and local environment variability between the CT scan acquisition and the procedure. These localization errors can lead to unacceptably low diagnostic rates of around 40-60%, meaning up to 60% of patients will undergo a bronchoscopy-guided biopsy procedure but not obtain an adequate diagnosis, which delays care and increases healthcare costs through repeat biopsy and surgical procedures. In fact, the primary reason that electromagnetic navigation is used in the lungs is primarily because there is still no safe, clinically useful method for real time visualization of the airways.

Thus, there is a need in the art to create an intraprocedural, real-time roadmap of the airways in the lungs on x-ray so that the operator can easily navigate to the nodule and have the best chance at obtaining a diagnosis for the patient.

SUMMARY OF THE INVENTION

Airways within the lungs are typically not visible under imaging modalities such as x-ray imaging. However, if the density of the airway tissues or the airways themselves are specifically altered, they may be detectable using x-ray imaging to produce previously unobtainable x-ray images of the airways. The density of the airways may be altered in a specific manner such that these changes are visible or detectable on x-ray imaging.

Generally, a catheter or delivery sheath may be introduced through the working channel of a bronchoscope while a proximal end of the delivery sheath may be connected to a controller or control unit. The distal end of the delivery sheath may be open to the airways of the lung region of interest and the delivery sheath may have lumens, e.g., for air/liquid injection, suction, and to transmit pressure measurements. Additionally, the delivery sheath may also incorporate a pressure transducer affixed to the distal tip of the catheter or integrated into any location along the length of the delivery sheath or within the controller. The delivery sheath may also incorporate a steerable component to allow bending of the tip of the catheter.

An isolation member may also be incorporated into the distal end of the delivery sheath where the isolation member may be formed as an expanding member, such as a compliant balloon, in order to occlude airways of varying size. The isolation member may be expanded to isolate fluid and/or pressure changes to the region of interest in the lung.

The delivery sheath may be connected to a controller which may include a microcontroller which is configured to receive signals and measurements, process these signals and measurements, and determine the optimal administration of fluid (e.g. gas, suction pressure or liquid such as saline) in order to meet pre-programmed or learned timings and thresholds. The controller may generally comprise a combination of connections or reservoirs for fluid, suction and gas, pumps, valves, computer processing units (microcontroller or microprocessor), pressure sensors, user controls, spirometer sensors, and x-ray triggering signal output connections. This controller could also comprise a fully mechanical system (for example, a configuration of syringes, springs, and pressure-limiting mechanical devices, etc.) or an electromechanical system (for example, a configuration of processing units, electromechanical pumps, valves and sensors, etc.).

The controller may receive a signal from a user, for instance, in the form of a button press, that the procedure has begun and the controller may also monitor for pressure signals from within the airways using, e.g., a piezoelectric chip at the distal tip and transmits the signal via a wire back to the controller. This pressure signal may be connected to the appropriate instrumentation, then communicated to the microprocessor within the controller. The microprocessor could then signal to a gas pressure modulation system to begin a routine.

This gas pressure modulation system may include any number of different types of pumps or a valve between positive and negative pressure lines. In this way, it may transmit a pressure waveform through the connection to the delivery sheath, through the delivery sheath itself, and distal to the delivery sheath inside the airways of the lung to create an oscillating pressure within the lung in order to cause alternating collapse and expansion of the airway. Alternatively, a fluid may be pumped into the delivery sheath from a reservoir until a particular pressure is reached. The pressure may be monitored by the pressure monitoring sensor and communicated to the microprocessor. The microprocessor may then turn a pump on and off to administer fluid from a reservoir to the delivery sheath connector. The microprocessor may monitor the pressure monitoring sensor continuously until a threshold pressure is achieved, at which point the microprocessor may turn the pump off. After a preprogrammed or learned timing, the microprocessor may signal to open a valve connected to a suction connector which may aspirate the fluid that had been administered from the delivery sheath.

The preprogrammed or learned routine controlled by the microprocessor may monitor the pressure distal to the isolation member in order to modulate the suction valve, flow of gas, and flow of fluid. The routine could also have set upper and lower bounds in pressure in order to avoid barotrauma and other pressure-induced damage to the airways and lung structures.

In one variation, the delivery sheath may be advanced into an airway which contains the region of interest (such as a lung nodule). The region of interest may then be isolated from the remainder of the lung and the controller system may then use, e.g., air suction (negative pressure) alternating with positive air pressure to cause the relatively elastic airways to collapse and then open, respectively (going from small diameter airway to a larger diameter). These changes in airway diameter can create airway density changes that can be detected on x-ray imaging. Other imaging modalities may also be used, e.g., CT, MRI, ultrasound, nuclear imaging, etc. Specifically, the density of an open airway (predominately air density) is significantly less than an airway that is collapsed (predominately water density).

When the airway is unmodulated it exists at a resting airway pressure and diameter. When the controller is in use, the airway pressure may be modulated from the above resting pressure to below resting pressure such that diameter of the airway increases and decreases. Specifically, if the pressure within the distal airways is increased, then the diameter of those airways increase from resting diameter to some larger diameter. When the pressure in the distal airways is below the resting pressure, then the diameter of the airway decreases from resting diameter to some smaller diameter. These differences in airway diameter create x-ray attenuation changes that can be displayed as a "roadmap" image which could be overlaid in real-time over a live x-ray image and allow the operator to navigate the catheter based on visualization of the airway roadmap. Unlike the existing technology, e.g. electromagnetic navigation bronchoscopy (ENB), which is not able to recreate a new map during the procedure, the airway visualization system described here may create a new map during the procedure at will and from various x-ray projection angles, showing the true location of the airways in real time.

In another variation, once the airways of interest have been isolated within the lung, the airways distal to the seal are at their resting pressure and diameter. Once in this position, x-ray imaging can be performed and at the same time the pressure in the airways distal to the starting airway/seal may be varied by the controller. Specifically, the controller may alternate negative pressure and positive pressure within the airways to induce airway diameter changes. Once begun, the pressure may be alternated between resting pressure, to a relatively higher pressure level, and then to a relatively lower pressure level which is less than the resting pressure, resulting in airway diameter changes from resting diameter to higher than resting diameter and then to a lower than resting diameter. This sequence of pressure changes may happen simultaneously with the x-ray imaging so that the density changes are captured and displayed on the x-ray monitor.

In another variation, a specialized bronchoscope may be advanced to the starting airway and the bronchoscope itself may be used to isolate a region of lung. The bronchoscope may be connected directly to the controller which, once activated, may vary the pressure of the distal airways from a maximum pressure to a minimum pressure which creates changes in airway density as the airways expand to a larger diameter and contract to a smaller diameter, respectively. The x-ray imaging may be performed concurrently with the sequence of pressure changes so that the density changes are captured and displayed on the x-ray monitor.

The sequence of pressure alterations can be modified in several different ways for optimal image creation. For example, the airway may be collapsed first and then expanded, or expanded first and then collapsed. Further, the pressure changes may steadily increase or decrease in force, applying increased (or decreased) pressures after each cycle.

The timing of the pressure changes in relation to the image acquisition is also relevant. Ideally, the pressure is varied at a known temporal pattern and the x-ray images are collected at times when the pressure, and therefore the airway dimensions, are different, and the resulting x-ray signal changes are used to enhance the visibility of the distal airways relative to the remainder of the lung which does not generate an x-ray signal.

In another variation of the temporal relationship between pressure changes and image acquisition, x-ray images may be acquired at a rapid rate, e.g., fluoroscopy at 30 frames per second, and the pressure may be oscillated while the fluoroscopy images are collected. The image acquisition rate may be relatively higher than the pressure oscillation frequency. Every image is ideally taken at a known temporal location compared to the pressure oscillation. The images may be processed in real-time to enhance pixels whose temporal signal variation is related to the pressure oscillation. For example, a matched filter can be designed which forms a weighted sum of the image sequence, with image frames having a higher pressure, having a positive weight and images with a negative pressure having a negative weight. Preferably, the average combination weight is zero. The result may show only pixels with a temporal variation related to the oscillation with static structures subtracted. That image can be displayed directly or overlaid on a real-time fluoroscopy image frame, or the average of several live frames, that would provide anatomic context. The temporally processed image can be overlaid on real-time fluoroscopy images, like a roadmap, while the operator is navigating the device.

Another variation of the temporal relationship between pressure changes and image acquisition may have the image acquisition rate at least twice the frequency of the pressure oscillation rate. The image acquisition rate may be phase-locked to the pressure oscillation rate so that images are acquired at the peaks and valleys of the pressure. Again, weighted combinations of the images may enhance the pixels with changes related to the pressure changes and, if the average weight is zero, static tissues may be cancelled (subtraction).

Generally, if the average weight of the combination of images is non-zero but small, some static tissue signal will remain and can provide anatomic reference. Simulations of expected signal changes suggest that inflation of the airway may provide more reliable signal changes than using suction sufficient to collapse the bronchi. The signal change related to collapse of a bronchus may depend on whether the collapse is side-to-side or front-to-back as seen from the x-ray source. That is, a higher contrast-to-noise ratio may be generated when the airway collapses from side-to-side rather than front-to back relative to the x-ray source. Thus, the airway collapse may be controlled such that the distal airways collapse from side-to-side relative to the x-ray source in order to generate the greatest contrast between the collapsed and expanded airways. Thus, a pressure change may have inflation at one extreme, and deflation but less than complete collapse at the other extreme (from side-to-side). The direction of collapse could be initiated by a particular delivery device cross-sectional geometry. In one embodiment there could be a delivery sheath with an elliptical cross-section, and an isolation member with elliptical cross-section. The major axes of the elliptical cross sections of the delivery sheath and isolation member may both be oriented such that they are front-to-back (in the line of transmission between the x-ray emitter and detector). As the pressure is decreased distal to the isolation member, the airway would preferentially collapse such that the major axis of the collapsed airway is also oriented front-to-back.

With respect to the choice of pressure modulation patterns, the choice of modulation pattern may affect the sensitivity of the method to unrelated patient motion (e.g., breathing, heart beating, or voluntary movement), or immunity therefrom. If the pressure modulation in the distal airways is relatively different compared to the unrelated motion (e.g. faster or slower, controlled by the pressure modulation device), then the airway density changes should be detectable relative to the unrelated motion. The image may still have blurring from the undesired motion, but the image will be less sensitive to motion unrelated to the pressure changes.

The strongest signal changes related to the pressure changes may come from the extremes of the pressure pattern. Image frames collected in-between the extremes of the pressure pattern may contribute less to the bronchial map, though they can contribute to the depiction of the underlying anatomy. Thus, the pressure patterns may be configured like square waves, with quick transitions, than smoother, more sinusoidal patterns.

In yet another variation, the controller may introduce a liquid (e.g., saline, etc.) into the airways before activating the controller to initiate positive pressure. If saline is replaced by air then a density difference can be observed on fluoroscopic x-ray which can be enhanced with subtraction processing. Once the imaging acquisition has been completed, the controller may automatically aspirate the liquid that was introduced into the airways. X-ray imaging can be performed concurrently with the controller activation and the images displayed on the x-ray monitor.

In yet another variation, the controller may create the density changes in the distal airways that can be displayed on the x-ray imaging device. Once the images are displayed as a roadmap, the isolation member may be removed (e.g., deflating the balloon). Using the roadmap for guidance, the delivery sheath may be navigated throughout the airways to reach the target area. This navigation would be possible because the delivery sheath may have a pre-curved shape or may be steerable.

In yet another variation, the pump system may be configured to generate an initial positive pressure between, e.g., 1 to 50 cmH2O, to ensure opening and to initially decrease the density of airways (which could be applied gradually). Once the airways are open, the x-ray imaging can be triggered and the pump system may stop generating positive pressure and switch to generating negative pressure through the delivery sheath and into the isolated segment of lung, with possibly a rapid drop in pressure or a more gradual drop in pressure until the minimum negative pressure is reached that generates sufficient increase in airway density to be detected on x-ray imaging (e.g., between −1 and −150 cmH20). Imaging may be stopped automatically once preset pressure safety limits have been reached or when the physician instructs the imaging to stop (radiation dose reduction techniques can be employed). The pump system may then stop the negative pressure, and the isolation member may be deflated, allowing the airways to open to its baseline size and shape once again. The delivery sheath and isolation member may then be advanced through the airway using the density change x-ray map for guidance, after which additional images may be performed if necessary. The delivery sheath may be steerable and could be used with a single hand so that the user can maintain the position of the bronchoscope. The physician may navigate to the target nodule and a biopsy can be obtained.

In yet another variation, the airway density may be maximally decreased while imaging. To accomplish this, before activating the x-ray imaging, the physician may instruct the controller and/or pump system to generate negative pressure within the isolated lung segment to collapse the airway walls and increase the density of the airway maximally (e.g., between −1 and −150 cmH20, reaching minimum pressure rapidly or gradually). Once collapsed or closed, the user can activate the x-ray imaging through the connection between the x-ray machine and the controller. Once imaging is activated, the controller may trigger the pump system to run a preprogrammed routine. The pump system may then release the negative pressure, allowing the airways to recoil open and return to their resting density while imaging is performed. Simultaneously, or just after this return to baseline density/shape, positive pressure may be applied from the pump system to generate some pressure above resting baseline to open the smaller airways that may not have recoiled open independently when the negative pressure was released. The volume of air injected by the pump system may be regulated by the pressures that are generated within the lung during injection (pressure limited, to prevent both filling of the alveoli which would degrade image quality as well as preventing damage to the lung, called barotrauma; pressure ranges from 0 to 50 cm H20 with the pressure rise being rapid or gradual). The air injection may stop when maximal airway density drop has been achieved, imaging is satisfactory or prescribed safety limits of pressure are reached. Once that occurs, the x-ray machine and pump system may stop, and the isolating component may be deflated (or reconstrained). The user may navigate to the target nodule and can generate additional bronchogram images as the delivery sheath advances deeper into the lung as needed.

In yet another variation to maximally increase the density change of the airways, before activating the imaging x-ray machine, the user can instruct the controller/pump system to generate positive pressure (between, e.g., 1 to 50 cmH20, gradually or rapidly) within the isolated lung segment to open any airways that might be collapsed at baseline. Once the airways are open (specifically lowering the density of the airways), the controller may trigger the pump system to run a preprogrammed routine and inject saline (normal or 0.9% saline) to then maximally increase the density of the airway. This specifically increases the density of the airways, which can be detected on x-ray imaging and enhanced with subtraction processing. The pump system may stop injecting when prescribed safety pressure limits are reached. Once that occurs, the x-ray machine and pump system may stop, and the isolating component may be disengaged (or deflated). Additionally, the pump system can run a preprogrammed post-imaging routine to automatically suction the saline from the airways and collect it for laboratory analysis, if needed.

In yet another variation, the user can instruct the controller/pump system to inject saline into the isolated lung segment (pressure range from, e.g., 1 to 50 cmH20). With saline in the airways and alveoli, the controller may then inject air or a bubble mixture (with a range of bubble sizes to prevent filling of the alveoli during imaging) into the airways (pressure range from, e.g., 1 to 50 cmH20). This may create an airway density change between the saline filled airways which are high density to low, air density, when the air or bubbles are injected. These specific airway density changes can be enhanced with subtraction x-ray image processing. The pump system may stop injecting when imaging is satisfactory or prescribed safety pressure limits are reached. Once that occurs, the x-ray machine and pump system stop, and the isolating component may be disengaged (or deflated). Additionally, the pump system can run a preprogrammed post imaging routine to automatically suction the saline from the airways. The physician can use the images generated from the density change to navigate to a specific target within the lung.

In yet another variation, before activating the imaging x-ray machine, the user can instruct the pump system to generate positive pressure within the isolated lung segment to open the airways that might be collapsed at baseline (and thus to decrease the density of the airways) as well as to fill the alveolar sacs with air to a certain pressure (range from, e.g., 1 to 50 cmH2O). Once certain airway pressures are reached, implying that any baseline closed airways are open and the alveolar sacs are filled (confirmed by pressure readings from the sensors), the user can trigger the x-ray system as well as the controller/pump system to run a preprogrammed routine. The pump system may then release or inject a radiodense gas (e.g., Xenon or Krypton) while x-ray imaging is performed. The density difference between the air-filled airways and radiodense gas may be detected as a contrast change by the imaging detector. The pump system may stop injecting when an adequate bronchogram is generated or when prescribed safety pressure limits are reached. Once that occurs, the x-ray machine and pump system may stop, and the isolating component may be disengaged (or deflated). Additionally, the pump system can run a preprogrammed post imaging routine to automatically suction the radiodense gas from the airways.

In yet another variation, the density of the airways may be changed and not the density of the lung tissue (as this would obscure the underlying airways). The lung tissue/alveoli may be deflated before airway density changes are performed. For example, once the isolating component is in place, the controller/pump system may run a preprogrammed routine to gradually remove the excess gas from the alveoli before the controller airway routine is triggered (e.g., to deflate the lung tissue) so that upon negative pressure application, the lung tissue cannot change in density any further. Alternatively, application of high oxygen percentage within the air injected by the controller (e.g., 20 to 100% O2) can also cause the alveoli to close, thus mitigating further density change by the lung tissue while airway density change routines are being triggered. Alternatively, the airways may be filled with a fluid before the controller airway routine is triggered. In this case, if the airways are already expanded with a fluid, then the lung tissue may not change in density when the controller airway routine is triggered. Specifically, if the lung tissue is filled with saline to a range of pressure (e.g., 0.1 to 50 cmH2O), then the lung tissue will resist changing in shape or density when the airway routines are applied secondary to the cohesive properties of liquid saline (e.g., the alveoli may not be susceptible to movement by a gas such as air if they are filled with a liquid). In other variations, the timing of the pressure changes within the lungs may prevent the lung tissue from changing in density. Either the gradual or rapid application of pressure from the controller might alter the airway density without affecting the lung tissue.

In yet another variation, the lung nodule or tissue region of interest may be visualized in addition to the airways, e.g., while performing a biopsy procedure. The density of the alveolar lung tissue itself, rather than the airways, may be altered. In this method, density changes may be used to highlight a soft tissue growth or tumor in the lung. The controller can apply a negative pressure to collapse the alveolar lung tissue (pressure range from, e.g., −1 to −150 cmH2O, gradually applied). This may increase the density of the lung tissue surrounding the growth. Once certain pressure measurements have been reached, then x-ray imaging can be activated and the controller can reverse the negative pressure and apply positive pressure to the alveolar lung tissue (range, e.g., 1 to 50 cmH2O). This may significantly decrease the density of the alveolar lung tissue as it expands with low density air. The growth, however, will not expand with air, as it is a solid tissue mass. Thus, while the surrounding lung tissue may become less dense on x-ray, the lung growth itself may remain the same density, and will be displayed as a dark outline surrounded by low-density, air-expanded lung tissue on the x-ray image. These density changes can then be enhanced using subtraction image processing. The user could then use the airway map and the nodule shadow to navigate towards the nodule.

In yet another variation, the controller could apply an initial positive pressure of, e.g., 1 to 50 cmH2O to decrease the density of the isolated region of interest. Once certain safety pressures have been reached, then x-ray imaging could be performed and the pressure reversed to negative pressure (range, e.g., −1 to −150 cmH2O). The negative pressure delivered to the alveolar lung tissue may collapse the tissue, and thus increase the surrounding lung tissue density, being displayed as a darkening of the lung tissue. The growth, however, may not collapse or deflate, and thus would remain the same density. This could be visualized as a light outline of the growth surrounded by darkened (higher density collapsed) lung tissue. The user could then navigate to the nodule using the airway map and the nodule shadow to navigate towards the nodule.

In yet another variation, the system and method may be used to improve the visualization of lung nodules on x-ray tomographic imaging such as CT. With CT imaging, when a bronchoscope is advanced into an airway there is decreased ventilation of that area. As a consequence, the region of lung that is supplied with air through the airway that contains the bronchoscope tends to develop atelectasis, or collapse/deflation of the lung tissue. This increases the density of the lung tissue surrounding the nodule to a range that is very similar with the soft tissue nodule, which can obscure visualization of the nodule on imaging (including CT imaging). To prevent the nodule from becoming invisible, introduction of positive air pressure (continuous or intermittent, range of, e.g., 1 to 50 cm H2O) into the isolated region of the lung could be used to pressurize/inflate the alveolar lung tissue with gas, thus decreasing the density of the lung tissue relative to the soft tissue nodule, which could be used to again visualize the nodule with x-ray on either CT imaging or with x-ray fluoroscopy (with or without enhancement with subtraction processing). This could improve the ability of a user to target the nodule during x-ray or CT guided biopsies, with CT guidance being a high resolution imaging platform, that might otherwise be limited if lung deflation or atelectasis occurs around the nodule. This atelectasis limits imaging of the lung nodule because the collapsed lung tissue is relatively similar in density to the underlying lung nodule, such that the nodule is not well distinguished from the surrounding collapsed lung tissue. Re-expanding the lung tissue decreases the density of the alveolar tissue, allowing for the nodule to be distinguished relative to the now expanded and less dense lung tissue.

In one variation of the airway visualization system, the system may generally comprise an elongate delivery sheath having a length and defining at least one lumen therethrough, wherein the length is positionable within an airway of a subject. An isolation component may be positioned near or at a distal end of the elongate delivery sheath and expandable to at least partially obstruct the airway and a controller may be in communication with the delivery sheath. The controller may be configured to manipulate a fluid flow through the at least one lumen whereby a pressure change within the airway of the subject is imparted sufficiently to at least partially expand or collapse the airway at a rate detectable by an imager.

In one method of visualizing an airway within a subject, the method may generally comprise fluidly isolating the airway in proximity to a tissue region of interest via an elongate delivery sheath positioned through at least a portion of the airway and obtaining a baseline image of the airway via an imager. A fluid flow through at least one lumen of the delivery sheath may be manipulated such that a pressure change is imparted within the airway sufficient to at least partially expand or collapse the airway whereby a density of the airway is altered. The pressure change may also oscillate between relative positive and negative pressure states such that the airways alternately expand and collapse, also creating repeated density changes within the airways that can be visualized. This density alteration can be enhanced using subtraction image processing.

In another method of visualizing an airway within a subject, the method may generally comprise fluidly isolating the airway in proximity to a tissue region of interest via an isolation member positioned upon an elongate delivery sheath which is positioned through at least a portion of the airway and obtaining a baseline image of the airway via an imager. A fluid flow through at least one lumen of the delivery sheath may be manipulated such that a pressure change is imparted within the airway sufficient to at least partially expand or collapse the airway at a rate detectable by the imager, thus creating a density change. This density alteration can be enhanced using subtraction image processing.

BRIEF DESCRIPTION OF THE DRAWINGS

FIGS. 5A and 5B show perspective and end views of another variation of a delivery sheath having an expandable structure formed as a stent-like device.

FIGS. 6A and 6B show perspective and end views of another variation of a delivery sheath having a plurality of openings along a distal portion.

FIG. 7 shows a perspective view of another variation of a delivery sheath having a plurality of tubular branching compliant balloons.

FIGS. 8A and 8B show perspective and end views of another variation of a delivery sheath having a plurality of radiopaque wires or ribbons.

FIGS. 27A to 27C show x-ray images of an in vivo porcine model in which the airways become visible after density changes to the airways and density change enhancement with subtraction image processing have been applied.

DETAILED DESCRIPTION OF THE INVENTION

This disclosure relates generally to lung imaging and procedures. Specifically, it relates to systems and methods for displacing specific structures within the lung or lungs (e.g. expanding/collapsing airways to change the density of the airways, moving the airway walls in such a way to distinguish the airways from surrounding structures such as blood vessels, expanding alveoli relative to a pulmonary nodule to enhance the nodule) to enable visualization of these structures using various imaging modalities such as x-ray. This x-ray visualization will facilitate any number of bronchoscopy-guided lung procedures such as lung biopsies, tumor ablation, bronchoscopic valve placement for COPD patients, etc. The system may be generally comprised of a controller, pump system, and a delivery sheath which may be used to temporarily alter the density of the lung structures (such as airways and alveolar lung tissue, also called lung parenchyma) in such a manner as to be useful, e.g., for bronchoscopy-guided procedures.

Because most airways of the lungs are not typically visible on x-ray imaging (e.g., bronchogram showing branching images of the airways), the images generated using the system may generally involve advancing a delivery sheath to a position in the lung airways in proximity to the region of interest, and then displacing the airway walls to alter the density pattern of the airways or altering the density between the air or fluids within the airways and the surrounding tissue walls. The density may be altered within a localized region of the lung or localized regions within both lungs. Alternatively, the entire lung or both lungs may have their respective airways altered in density for imaging the airways of one or both lungs. This changing of airway density may be accomplished through any of the systems and methods described herein. As the density of the tissue defining the airways are altered temporarily, the airways of interest become visible on an x-ray imaging system and the resulting image or images can then be used to aid the physician, e.g., in airway navigation during the biopsy procedure.

Figure 1:
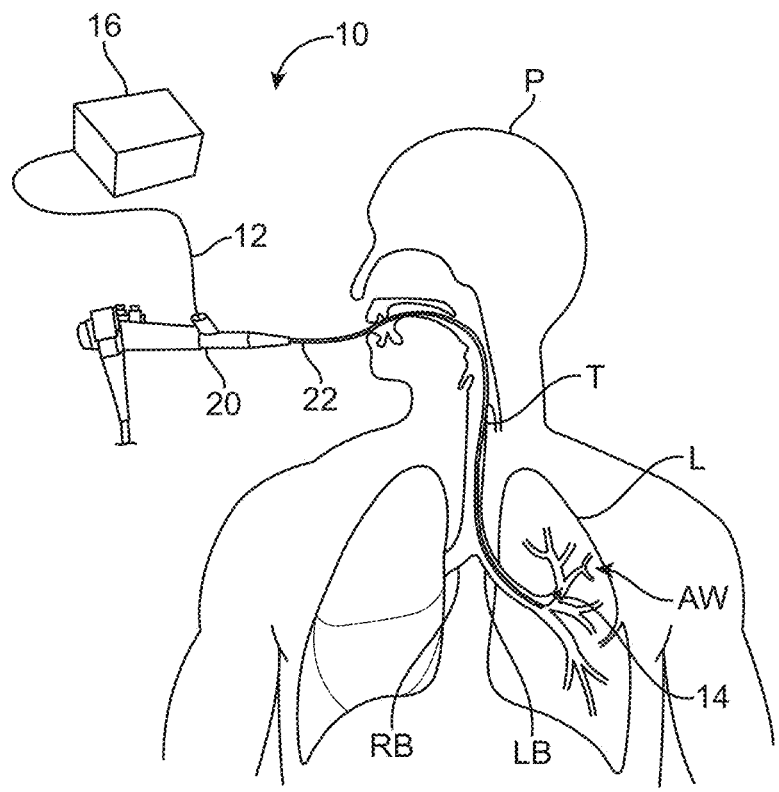
FIG. 1 shows a schematic illustration of one variation of the imaging system.
Figure 2A:
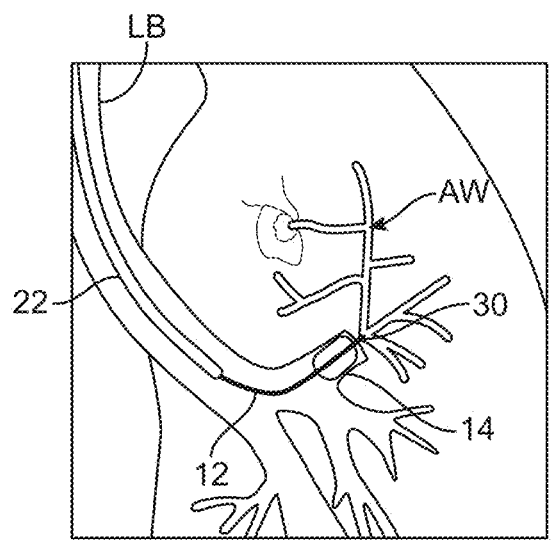
FIGS. 2A and 2B show examples of the delivery sheath altering the density of an isolated airway.

Referring to FIG. 1, one example of the system 10 is shown in use for imaging the airways AW of interest within a lung L of a patient P seen having a trachea T with a left bronchus LB and right bronchus RB and nodule or lesion ND. An endoscopic device 20, such as a bronchoscope, may be introduced through the trachea T and into proximity of the tissue region of interest. In this example, the elongate body 22 of the bronchoscope 20 may be introduced, e.g., into the left bronchus LB and a delivery sheath 12 may be introduced, e.g., through a working lumen of the elongate body 22, until the distal end of the delivery sheath 12 exits out of the elongate body 22 and is further advanced into the airways AW of interest. The delivery sheath 12 could have an isolating component 14, e.g., an expandable balloon positioned near or at a distal end of the delivery sheath 12, which may be reconfigured from a low-profile delivery configuration into an expanded configuration, as shown in FIG. 2A, such that the isolating component is expanded against the surrounding walls of an airway AW of interest such as one of the bronchioles to isolate a segment of lung L.

The delivery sheath 12 may generally comprise an elongate structure, similar to a catheter or bronchoscope, with proximal and distal ends and at least one central lumen or several lumens that could connect a pump system to the internal environment of the lung through the nose or mouth. The delivery sheath 12 may also include a steerable distal portion for facilitating navigating within the airways. The diameter of the delivery sheath 12 could be small enough to fit within existing bronchoscope 20 working channels (e.g., outer diameter less than 3 mm) or it could be placed alongside the bronchoscope 20 or replace the bronchoscope completely in which case its diameter could be larger (e.g., larger than 3 mm and less than 20 mm). The delivery sheath 12 could also be a modified bronchoscope. The delivery sheath could have at the distal end an isolating component (e.g. expandable member such as a compliant balloon), which could fluidly isolate the segment of lung being imaged.

With the airway of interest AW isolated from the rest of the lung L, a fluid such as a gas and/or liquid may be optionally administered through the delivery sheath 12 and into the airway AW in order to assist with imaging of the airways. When the airways AW are open and unaffected, the airway tissues have an initial density (e.g., from the air within the airways) which is typically not visible when imaging under x-ray. However, altering or moving the airway tissue enables x-ray imaging to visualize the tissue. That is, x-ray imaging is able to detect and image the tissue region of interest as the density of the airway is altered from the air to the surrounding airway tissues. Hence, altering the airway tissues to change density from an initial density value to a relatively higher or relatively lower subsequent density will allow for x-ray imaging to image the changing density. By imaging this change in density, structures such as the airways of interest AW may be imaged by altering the density of the airways. Moreover, the surrounding airway tissues may be moved a nominal amount relative to a resting position of the airway. For example, the airways may be displaced a nominal distance of at least their wall thickness, e.g., 1.5 to 2 mm, for relatively thicker regions of airway walls or, e.g., 0.5 to 1 mm, for relatively thinner regions of airway walls. Moreover, the altering or movement of the airway walls may be accomplished by the introduction of a negative and/or positive pressure within the airways at a frequency of, e.g., 0.5 to 50 Hz, or at a frequency of, e.g., 5 Hz. The frequency of the airway wall movement may be varied depending at least in part upon the imaging frame rate, as described in further detail herein.

Figure 2B:
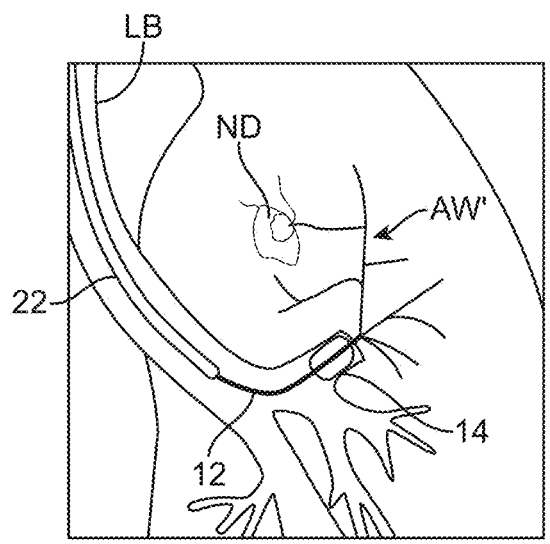

In one variation, a negative pressure suction may be applied through the delivery sheath 12 while the isolating component 14 is expanded while in another variation, a positive pressure may be introduced within the airways AW. Whether a positive pressure or negative pressure is applied, so long as the tissue walls of the airways are displaced enough to create a temporary and localized density pattern change in the airways relative to the rest of the lung tissue, the airways may be sufficiently imaged. If x-ray imaging is performed simultaneously, then the airways AW' of interest may be imaged as dark branching structures, as shown in FIG. 2B.

While different embodiments are described using the delivery sheath 12, other variations may instead utilize other devices such as an endotracheal tube or a mouth adapter which may impart or deliver the pressure changes described herein to the entire lung including the airways AW of interest.

Delivery Sheath

Figure 3A:
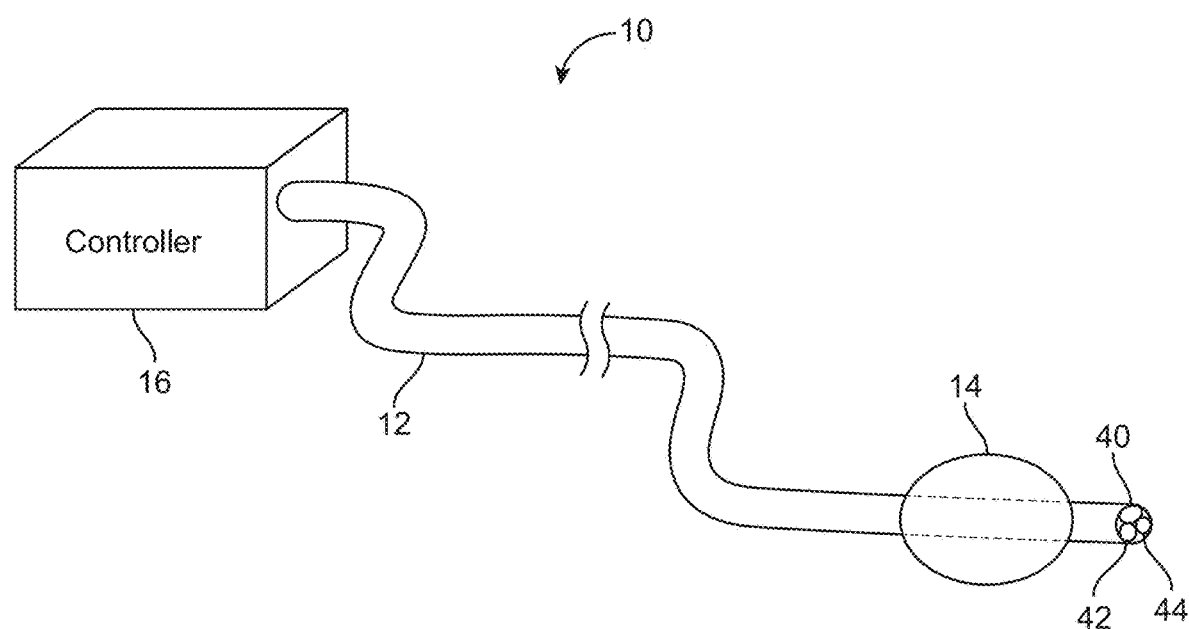
FIG. 3A shows a perspective view of one variation of a delivery sheath having an isolating component and controller.

As shown in the perspective view of FIG. 3A, the delivery sheath assembly 10, as discussed above, may generally include the elongate body of the delivery sheath 12 which may define one or more lumens through the body. The delivery sheath 12 may incorporate the isolating component 14 near or at its distal end for fluidly isolating the segment of lung containing the region of interest, and the delivery sheath 12 may be coupled directly or in communication with a controller unit 16, which will be described in further detail herein. The delivery sheath 12 may be formed from various biocompatible materials, e.g., silicone, polyurethane, PEBA-based thermoplastics, thermoplastics blends, PTFE or coextruded PEBA/PU with FEP or HDPE, etc. The body of the delivery sheath 12 may also be reinforced with a secondary structure such as inner braiding, coils or encapsulating a laser cut hypotube, and may also include varying durometers of overlying material (e.g. thermoplastic blends). The delivery sheath 12 could also have increased stiffness in the shaft proximally compared with distally to allow for steerability. As the delivery sheath 12 is flexible, its body may also be resistant to kinking during navigation within the lung.

Figure 3B:
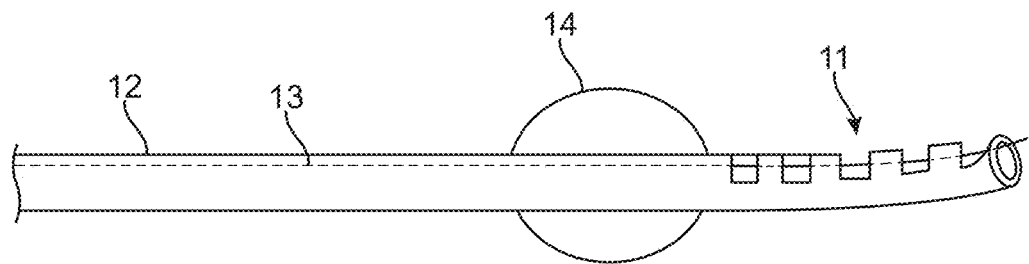
FIGS. 3B and 3C show side views of another variation of a delivery sheath having a steerable distal portion.
Figure 3C:
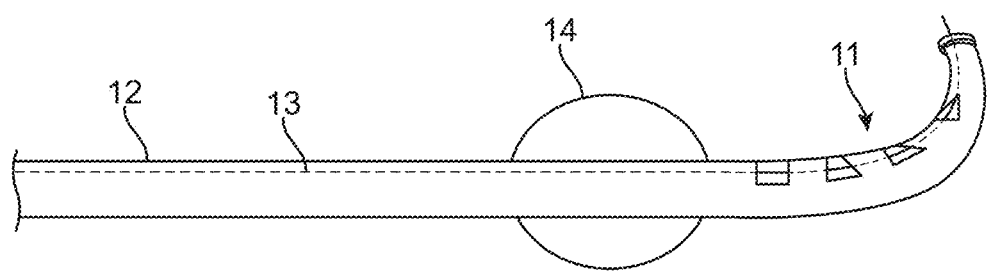
Figure 3D:
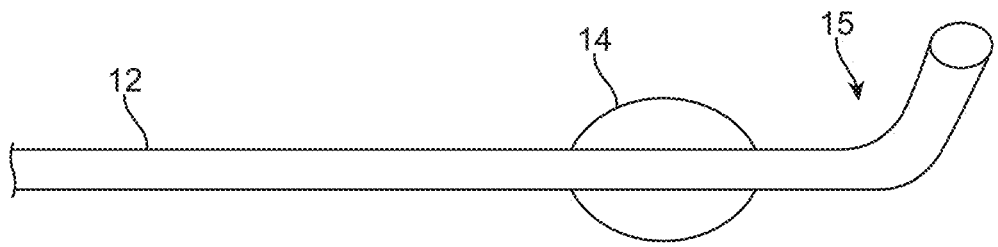
FIG. 3D shows a side view of yet another variation of a delivery sheath having a pre-curved distal portion.

Moreover, the delivery sheath 12 may include a steerable component or portion at the distal extent or tip, as shown in the side view of FIGS. 3B and 3C. The diameter of the delivery sheath 12 may range anywhere from, e.g., 2 mm up to 20 mm. Steerable mechanisms could include, e.g., a tendon-driven sheath with side notches 11 at the tip with a tendon-pulley mechanism to initiate flexion. Side notches 11 might be different sizes and shapes, allowing for tip-first bending by actuation of, e.g., a pull wire 13. The actuator for the tendon-pulley mechanism would be located at the proximal end of the delivery sheath, and could be hand or automatically actuated. If hand actuated, the actuator could be a trigger mechanism or button actuator, where the pull wire 13 is actuated by pulling or displacing the trigger or depressing the button. The steerable sheath could be constructed of shape memory alloy or an ionic metal composite and/or the sheath could be hydraulically driven with small hydraulic chambers positioned within the tip of the delivery sheath 12. The sheath could also be constructed from concentric nitinol tubes with pre-curved shapes that can provide steerability and stiffness to the delivery sheath. The steerable sheath could alternatively have a pre-curved tip 15, as shown in FIG. 3D, that would allow for manual rotation and advancement with one hand if needed. In such an embodiment, the pre-curved tip 15 may be pre-curved at any number of angles, e.g., 45 degrees, 90 degrees, 180 degrees, etc. The sheath could also be magnet driven with a deflectable tip.

The delivery sheath 12 could also be configured as a robotic delivery sheath (RDS) including, e.g., a robotic arm which may be articulated via one or more pull-wires or tendons attached at various locations along the length of the delivery sheath 12. The RDS in this instance may be steerable where the distal portion may comprise the isolating component 14. The RDS could be manually driven by a surgeon or automatically steered.

Figure 3E:
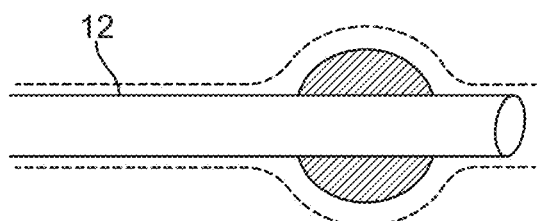
FIGS. 3E to 3J show side views of alternative variations of isolating components.
Figure 3F:
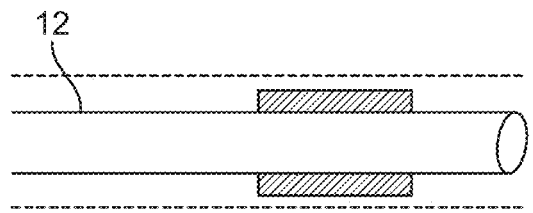
Figure 3G:
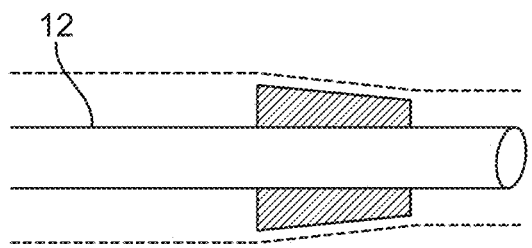
Figure 3H:
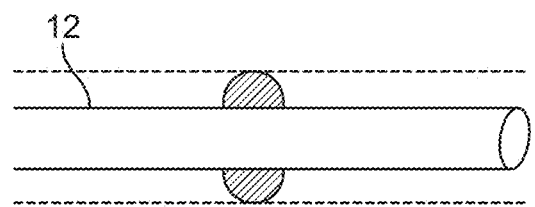

The isolating component 14 near or at the distal tip could be an expandable member, a non-expandable member, or the delivery sheath diameter itself. The isolating component may be located within 5 cm of the distal tip of the delivery sheath. The isolating component may take many shapes, from round/oval (as shown in FIG. 3E), cylindrical (as shown in FIG. 3F), conical or cork shaped (as shown in FIG. 3G), or ring shaped (as shown in FIG. 3H). If an expandable member, the delivery sheath could be an inflatable balloon which may function to isolate the region of interest AW from atmospheric or ventilator pressures within the remainder of the lung (e.g. transmittal of the pressure changes down to the smallest airway in the isolated region without significant interference from atmospheric pressure). The inflatable balloon variant of the expandable member isolating component 14 could be made from any number of compliant or non-compliant biocompatible materials, e.g., polyurethane, polyethylene (PET), nylon, among other materials, etc., and may have a diameter of, e.g., greater than 1 mm and less than 20 mm when inflated. The balloon could have many shapes. The balloon could also be designed to help stabilize the delivery sheath while instruments are placed through the delivery sheath. For example, when a biopsy needle is inserted through the delivery sheath the stiffness of the needle often displaces the tip of the delivery sheath. An expandable component could prevent such movement which could improve the accuracy of the biopsy. The shape of the balloon expandable member could be round, cylindrical, or conical, tapering in diameter from proximal to distal with the narrowing of the airways. The balloon may be less than 2 cm in length.

Figure 3I:
Figure 3J:
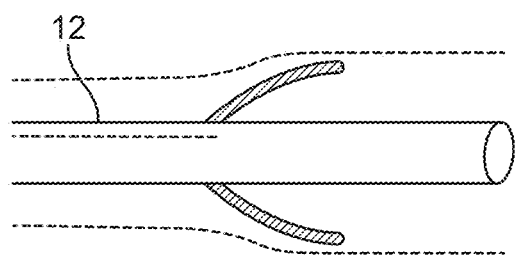

In other variations, the isolating component 14 may be configured as an expandable component such as an umbrella-shaped configuration having struts that is in a constrained low-profile configuration, as shown in the side view of FIG. 3I, when navigating the delivery sheath 12 and that may expand into a deployment configuration, as shown in the side view of FIG. 3J, to seal the airway when opened. This may include variations of an expandable member 14 having struts like a stent or truncated cone shape that could be used to keep the airway walls open around the tip of the delivery sheath 12 where the pressure changes might be greatest.

In other variations the delivery sheath 12 may instead incorporate an expandable structure 60 so as to prevent the premature collapse of the airways immediately distal to the delivery sheath tip. This premature closure prevents the negative pressure from being transmitted throughout the segment of lung containing the region of interest and reduces the visibility of the smaller airways. In one embodiment, the expandable structure is an expandable cage or stent like structure, which could for example would thus prevent the walls from collapsing. The stent-like device could be made of, or coated with, PTFE or any other suitable material so as to fluidly isolate the region of lung distal to the isolating component. One variation is shown in the perspective and end views of FIGS. 5A and 5B which show a delivery sheath 12 having expandable structure 60 formed as a stent-like device which may be deployed from a low-profile delivery configuration into an expanded curved or arcuate configuration designed to open the airways around the tip of the delivery sheath 12. The structure 60 may be formed of one or more wires which extend longitudinally along the length of the sheath 12 around the circumference of the sheath 12. Deploying the structure 60 may be accomplished by pushing or pulling one or more wires or elements which are coupled to the wires forming the structure 60. Expanding the structure 60 may prevent the airway walls from collapsing around the tip of the sheath 12 and may also prevent the transmission of pressure.

Furthermore, the delivery sheath 12 may define one or more lumens, including a lumen for the introduction of fluids, inflation of the isolating component 14, and/or the transmission of pressure information to a pressure sensing device which could be within the delivery sheath 12 or in the controller 16. The delivery sheath may also have a coaxially disposed outer sheath that could be left in place for the introduction of biopsy tools or radial ultrasound probe after navigating to the target (e.g. an extended working channel).

Alternatively, the isolating component 14 may be comprised of a non expandable member, such as a plastic component (e.g. truncated cone shape, or ring shape) that fits around the delivery sheath and sized to plug within an airway. This plug may be configured to range from 0.5 mm in diameter larger than the delivery sheath diameter to 20 mm larger than the delivery sheath.

In yet other variations, the isolating component 14 could instead be the diameter of the delivery sheath 12 alone. In order to isolate the airways of interest, contact between the outer surface of the delivery sheath 12 and the surrounding airway tissue walls may be sufficient to create a temporary seal to effectively fluidly isolate the airways for the purposes of imaging. Hence the isolating component 14 may be omitted entirely or it may remain in place but left in an unexpanded, low-profile state.

Alternatively, imaging of the airways may be performed while the patient is expiring air, so that the airways AW naturally collapse without the application of any positive or negative pressure. While the airways collapse or begin to collapse, a positive pressure may then be applied to re-open the airways, oscillating between positive pressure and negative pressure to open and then close the airways, respectively. In this manner, the airway density may be altered without affecting the remainder of the lung or other airways while enabling imaging. In addition, the airways are more amenable to closure during the expiratory phase of respiration.

Figure 4A:
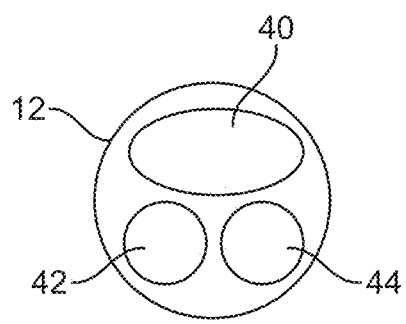
FIGS. 4A to 4D show end views of delivery sheaths having different lumen configurations.
Figure 4B:
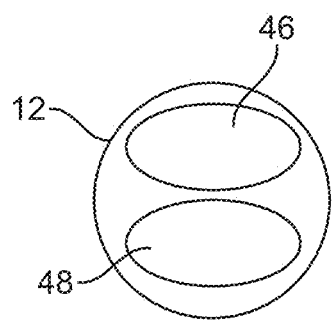
Figure 4C:
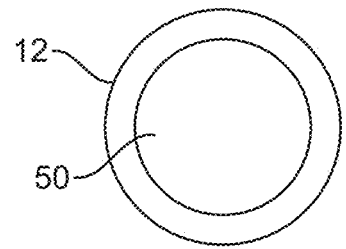
Figure 4D:
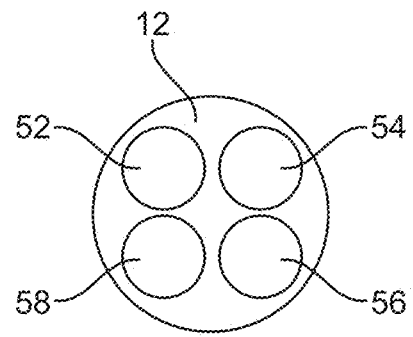

While FIG. 3A shows an example of the delivery sheath 12 having three separate lumens 40, 42, 44 (where lumen 40 may be configured to have a major and minor axis) any number of lumens may be used as desired depending upon the procedure to be performed. FIG. 4A shows the distal end of the delivery sheath 12 having working lumens 40, 42, 44 while other variations may incorporate fewer or more lumens having different cross-sectional shapes. FIG. 4B shows another variation have two lumens 46, 48 each having a major and minor axis while FIG. 4C shows another variation having a single lumen 50. FIG. 4D shows yet another variation having four separate lumens 52, 54, 56, 58.

Figure 4E:
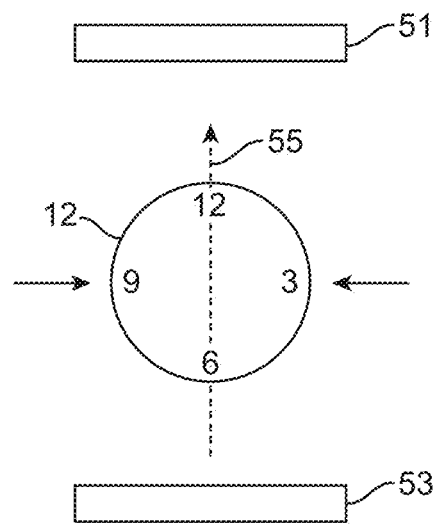
FIGS. 4E and 4F show schematic end views illustrating how the airways may be preferentially collapsed relative to the imaging source.
Figure 4F:
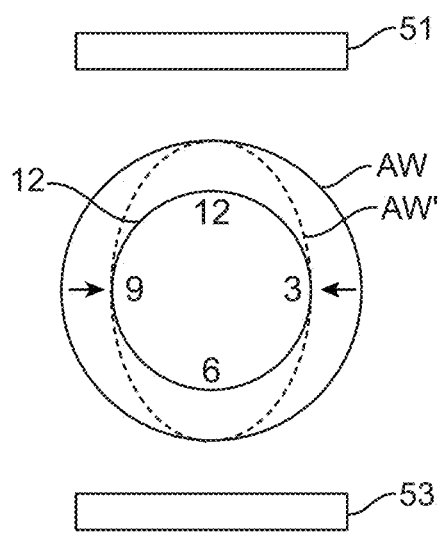

The density change in the airway tissue is highest when the airways close or collapse perpendicularly relative to the x-ray source-detector pathway 55 (e.g., the airways collapse vertically or in-line rather than flattening relative to the path between the x-ray detector 51 and x-ray source 53), as shown in the schematic end views of FIGS. 4E and 4F. Thus, it may be advantageous to create a device that can facilitate closing of the airways in such a way. For example, if the airways are illustrated a clock face, as denoted in FIG. 4E, with a straight line 55 between 12 and 6 being aligned with the x-ray source-detector pathway 55, higher pressures would be applied to 3 and 9 positions of the airway AW such that the walls collapse towards the line drawn between 12 and 6, as denoted by the collapsed airway AW'. In one embodiment, this could be done by manipulating the flow of suction such that the side walls are preferentially pulled together, as denoted by the arrows, before the top and bottom by having different lumen tip shapes. For example, the distal tip of the delivery sheath could have two exit side holes that are radially disposed around the delivery sheath tip, 180 degrees opposed from each other (on opposite sides of the tip of the delivery sheath) where the numbers 9 and 3 are indicated, as shown in FIG. 4F. A smaller exit opening could be at the very distal tip of the delivery sheath, longitudinally disposed relative to the length of the delivery sheath.

Two radiopaque markers could be disposed radially on the delivery sheath tip, 90 degrees from the side holes. By aligning the radiopaque markers with the x-ray beam such that the two markers overlap in the x-ray beam path, the side holes which are 90 degrees from the markers would then be located perpendicular to the x-ray beam. When negative pressure suction is applied through the delivery sheath, the pressure will be transmitted preferentially to the larger side holes over the smaller center opening, thus collapsing the airway walls AW perpendicular to the x-ray beam first. Once the walls are apposed with the sheath side holes, the negative pressure suction would then be transmitted through the slightly smaller end hole. Because the airways began closing perpendicular to the detector, the remainder of the walls distal to the isolating component would also preferentially collapse perpendicular to the detector, thus increasing image quality.

In another example, the lumen shape could be wider on the sides than in the middle (e.g., bowtie or butterfly shape) with radiopaque markers on the sides of the delivery sheath tip to show the orientation of the unique lumen tip configuration on x-ray. In another embodiment, the direction of collapse could be initiated by a particular delivery sheath isolating component cross-sectional geometry. For example, there could be an isolating component with an elliptical or bilobed cross-section. The major axes of the elliptical or bilobed cross sections of the isolating component would both be oriented such that they are front-to-back (in the line of transmission between the x-ray emitter and detector). As the pressure is decreased distal to the isolating component the airway would preferentially collapse such that the major axis of the collapsed airway is also oriented front-to-back.

The delivery sheath could also take the form of an adapted bronchoscope delivery sheath (BDS). The BDS would have a proximal and distal end and one or more lumens. A local imaging component, e.g., a CCD or CMOS camera component or fiber optic bundle, at the distal end may be used to see inside the body. The BDS may include a working channel for the introduction of tools such as biopsy forceps. The BDS may also be flexible and have both an isolating component 14 at the distal end and an optional steerable component. The BDS could also be navigated to the region of interest and the isolating component and pump/controller system activated, creating airway density changes within the lungs.

As described briefly above, it may be beneficial to prevent premature closure of the proximal airways from negative pressure suction. Thus, in one structure, a porous structure may be used. For example, in the variation shown in FIGS. 6A and 6B, a delivery sheath 12 having a portion 62 of the sheath distal to the isolating component 14 is configured to be porous so that negative pressure is transmitted distally into the region of interest. The portion 62 may define one or more openings or holes 64 (e.g., less than 3 mm) around the sheath 12 such that a positive and/or negative pressure may be applied via the sheath 12 uniformly to the airways around the portion 62 within the isolated portion of the airway to overcome the tendency of the airways to deform due to the high suction gradient near the distal tip of the delivery sheath 12, which could lead to occlusion or coaptation of the airway walls AW at the delivery sheath tip and prevent the transmission of the negative pressure into the peripheral airways. The openings or holes 64 may provide sufficient porosity such that when negative pressure is delivered through the delivery sheath 12, a pressure gradient is formed to prevent occlusion of the airways at only the delivery sheath tip. In this embodiment, the delivery sheath 12 may be inserted into the lung segment containing the target until it is within the distal aspect of the lung L, generally near the region of interest. The delivery sheath 12 may be placed within the distal lung either with x-ray, with direct visualization through a bronchoscope, or after performing an initial bronchogram (airway image) in more central airways. Once the delivery sheath 12 is placed in the peripheral lung, suction could be applied from the pump system which would be transferred throughout the length of the delivery sheath 12 and through all of the openings or holes 64. Each of the openings or holes 64 may then transmit the pressure outside the delivery sheath 12, with many side holes being physically close to branch points of the airways. This will also allow the direct transfer of the suction into the many side branches of the lung L (rather than creating a single point source for suction when the delivery sheath contains only one end hole), creating a uniform increase in airway density around the delivery sheath 12 and into adjacent airway branches and forming a uniform bronchogram image. The openings or holes 64 could be customized to the length of the airways to be collapsed. The isolating component could then be adjusted so that all of the side holes are distal to the isolating component 14.

Yet another variation is shown in the perspective view of FIG. 7 which shows a delivery sheath 12 having a distal portion 70 extending from the sheath 12 and having a plurality of tubular branching compliant balloons 72, e.g., five or more balloons 72, extending at an angle from the distal portion 70. When unconstrained, expanded, or advanced through distal opening 30, the branching balloons 72 can be filled with a contrast medium such as iodinated contrast liquid such that the balloons 72 expand into the surrounding airways and fill the airways for imaging their locations on x-ray.

Another alternate variation utilizing balloons may utilize eversion balloons that can fill with contrast medium. Such an eversion balloons may be inflated from the inside out such that the balloon everts while expanding to lengthen from the distal tip of the balloon. Multiple eversion balloons can be constrained together within a delivery sheath 12 and when ready for imaging, contrast can be injected into all the constrained eversion balloons, which may expand at the distal tip, filling with contrast that can be seen on x-ray. The eversion balloons may extend into the airways together, and when branch points are encountered, the balloons may naturally divide, some of them travelling down each airway. As the contrast extends the eversion balloons, the airways will be seen on x-ray and a roadmap can be generated. The eversion balloons can then be deflated and re-constrained and the delivery sheath 12 can navigate to the target.

Yet another variation is shown in the perspective and end views of FIGS. 8A and 8B. In this embodiment, the delivery sheath 12 may contain a plurality of adjacent radiopaque wires or ribbons 80 (e.g., metallic wires) that are pre-formed to curve in different radial directions. Each wire has an atraumatic, blunt, or rounded tip to avoid damage to tissues when being inserted into the airways. During delivery, the plurality of wires 80 may be positioned within the delivery sheath 12 until deployment within the airways, when the plurality of wires 80 may be advanced from the distal opening 30 of the delivery sheath 12. When the bundle of wires is inserted into a main airway, the individual wires 30 will naturally and stochastically diverge as the wires 80 encounter branch points and take different airway paths depending on the branching pattern of the region of interest. Some wires 80 will take each route as the wires are precurved and want to travel at acute angles relative to one another. This will continue for several generations of branches, with fewer and fewer wires 80 remaining bundled together. Ultimately, the wires 80 may not advance any further and the resulting image will show wires 80 within many different airways. This image can be saved and used as a roadmap. The wires 80 can be re-constrained and the delivery sheath 12 can be navigated to the target location. Additional wire bronchograms can be performed as needed.

Yet another variation may utilize thin, flexible, atraumatic, lightweight and radiopaque streamers which may be attached to the distal end of delivery sheath 12. The streamers may be initially confined or constrained within or around the delivery sheath 12 until x-ray imaging is performed. The delivery sheath 12 can be maneuvered into a starting position through the bronchoscope, alongside the bronchoscope or in place of the bronchoscope as in previous embodiments. Once ready for imaging, the streamers may then be released from their constrained state and are free to move or flow freely within the lung based on respiration. The streamers may move down the airways via natural respiration (e.g., during inhalation), or could be augmented with the use of positive air pressure through the delivery sheath 12 or endotracheal tube (e.g. with an open system of ventilation to prevent over pressurization). The streamers may move with the flow of air, and may travel down various airways, highlighting them on x-ray. Once the steamers have traveled within the airways, an image can be recorded and used as a roadmap for navigation. The streamers can once again be constrained, and the delivery sheath can then navigate down the airways according to the roadmap. Additional roadmaps can be obtained as needed until the target is reached.

In yet another variation, the delivery sheath 12 could be configured to incorporate one or more wires which may be deployed from the sheath 12 and into contact against the tissue walls of the airways to deliver an electrical stimulation. The wire (or wires) may deliver an electrical stimulation optimized to stimulate smooth muscle contraction. When imaging, stimulation may be applied such that the airway walls collapse temporarily to increase the density of the local airways that could be used for x-ray imaging. For example, the delivery sheath could have an expandable member that is not an isolating component, but would instead be composed of wires similar in orientation as FIGS. 5A and 5B. However, these wires would be in contact with an electrical generator to generate electrical stimuli within the airway smooth muscle. The generator could provide a number of voltages, frequencies and pulse durations. Various waveforms could be applied such as square wave or sine wave. Ideal conditions would include voltages between 10-30 volts, 10-35 Hz and 0.1-2 ms to stimulate the smooth muscle in the airways to contract.

In another embodiment, the delivery sheath 12 may be used to deliver medications known to cause bronchoconstriction, thus increasing the airway density. Drug classes that could be used include parasympathetic agonists (e.g. methacholine), beta blockers, cholinesterase inhibitors, angiotensin converting enzyme (ACE) inhibitors. These medications could be delivered in small quantities specifically to the airways of interest to create specific airway collapse in a region of interest.

Figure 9A:
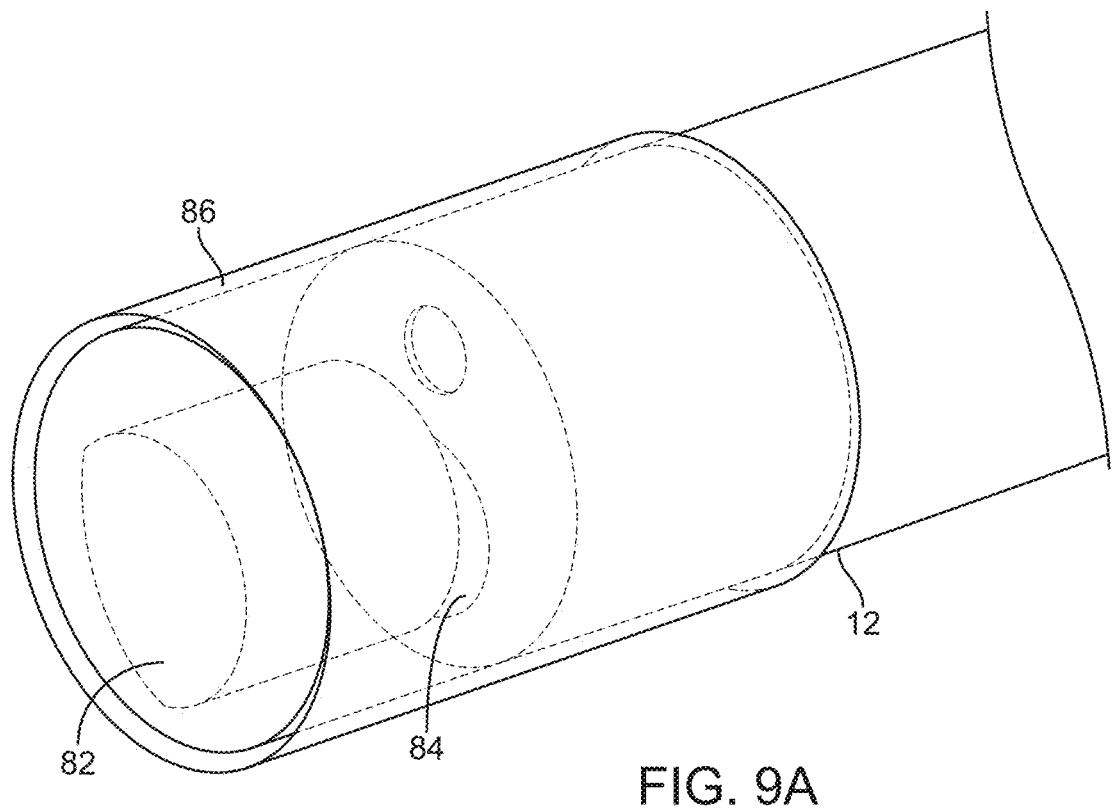
FIG. 9A shows a perspective detail view of a distal end of a delivery sheath which is configured to deliver vibrations within the airways.
Figure 9B:
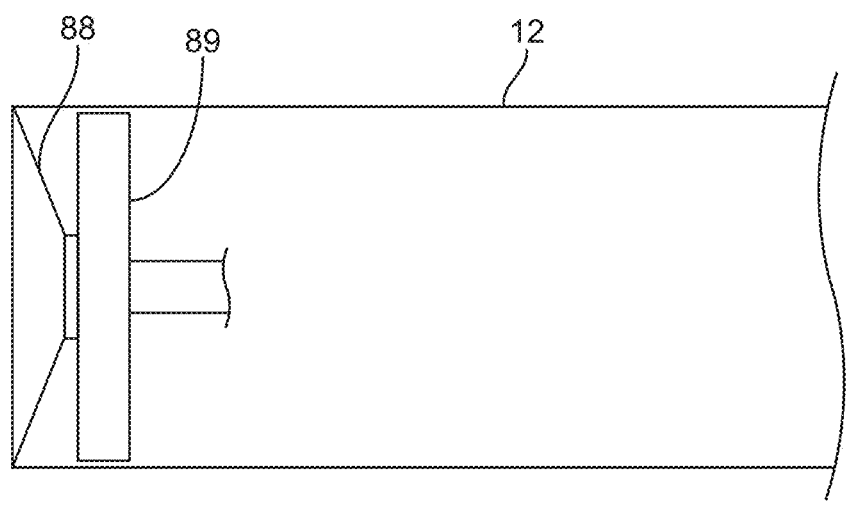
FIG. 9B shows a schematic side view of another variation utilizing a diaphragm.

In yet another embodiment, the delivery sheath 12 may be configured to deliver vibrations to the airways. These vibrations may rapidly alter the density pattern within the airways and the vibrating tissue may be detected on x-ray imaging. One example is illustrated in the perspective view of FIG. 9A which shows a distal portion of a delivery sheath 12 with an asymmetric weighted member 82 positioned to extend from the distal tip. The weighted member 82 may be movably coupled to the distal tip via a support arm 84 and the entire weighted member 82 and support arm 84 may be entirely enclosed by a cover 86. When the cover 86 and/or portions of the delivery sheath 12 are positioned into contact against the airway walls, the vibrational energy may be transmitted to the surrounding airway wall tissues via vibrational conductance at a frequency of, e.g., 0.5 to 50 Hz, again optimized to the imaging frame rate where the vibrational frequency is best seen at less than half of the frame rate. Alternatively, a liquid such as saline may be infused into the local area to provide for a vibrationally conductive medium through which the vibrational energy may be transmitted directly into the surrounding airway walls.

The weighted member 82 may be configured to vibrate when actuated in a distal-proximal direction in parallel with a longitudinal axis of the delivery sheath 12 such that vibrations are induced in a longitudinal direction from the delivery sheath 12 to create compression waves through the air within the airways and through the airway tissue walls. Alternatively, the weighted member 82 may be vibrated in a rotational direction such that a longitudinal axis of the weighted member 82 moves relative to the longitudinal axis of the delivery sheath 12 yet remains parallel with one another. In this case, the weighted member 82 may have an offset center of mass in order to induce a vibration. In another variation, the weighted member 82 may rotate in an eccentric manner relative to the delivery sheath 12 such that vibrations are induced in a radial direction from the delivery sheath. In each of these variations, a motor may be positioned within or in proximity to the distal tip of the delivery sheath 12 or the motor may be positioned within the controller and a rotational or longitudinal impulse may be transmitted along the length of the delivery sheath 12. In yet another variation, one or more piezoelectric elements may be positioned near or at the distal end of the delivery sheath 12 in which case the one or more piezoelectric elements may be positioned in one or more different locations depending upon the type and direction of vibration energy to be transmitted.

In yet other variations utilizing vibrational conductance, other mechanisms may also be used to impart vibrations into the airways of interest for imaging. In one variation, rather than using the elongate delivery sheath 12, other devices such as an endotracheal tube, mouth adapter, etc. may be used to deliver the pressure changes or even vibrations into the airways AW of interest.

In yet another variation for delivering vibrations, any of the devices described may be used to deliver sound waves or pressure waves (compression impulses) into or through the airways AW of interest. In one such embodiments, as shown in the schematic side view of FIG. 9B, the sound waves may be generated by a speaker or other vibrational component, e.g., piezoelectric actuator, oscillating piston, mechanical actuator, electromechanical actuator, etc. which may be positioned upon the delivery sheath 12, endotracheal tube, mouth adapter, etc. for imparting the sound waves or pressure waves. One example may take a weighted member 89 described for longitudinal vibrations and include a diaphragm 88 on the tip or other conical structure such as a speaker shape to create the pressure waves as the weighted member translates back and forth longitudinally. With the sound waves or pressure waves, the flow of fluid may be omitted and would also not disrupt the delicate tissues within the lungs, such as the alveoli.

In yet another variation for delivering vibrations, any of the devices can be used to deliver vibrations to the lung tissue as well as the airways. Vibrations delivered to the lung tissue can be used to outline pulmonary nodules and other structures such as blood vessels. As the vibrations move the nodules and blood vessels, it creates a density pattern change on the x-ray image which can be enhanced using digital subtraction processing. This creates an edge-enhancement effect where the edge of the nodule or blood vessel is visualized.

Controller

Turning now to the controller 16, the controller 16 may have a user interface directly incorporated upon the controller 16 or the user interface may be located remotely from the controller 16. The controller 16 could be positioned upon a moveable stand (e.g. with wheels or portable) that can freely move around the procedure room or could be hand-held by the physician or an assistant (and optionally manually activated). A pneumatic pump system may be incorporated directly within the controller 16 or the pump may be comprised of an external source of air supply and/or suction (e.g., from a hospital wall fixture) or could be comprised generally of mechanical or electromechanical pumps, valves, fluid reservoirs, and processing units (microcontroller or microprocessor). One or more pressure sensors may also be incorporated directly within the controller 16 itself and/or within or along the delivery sheath 12 such that the pressure sensors may be used to intermittently or continuously detect and relay pressure changes in the isolated segment of lungs to the controller which may provide feedback to the controller 16 for optimizing density changes of specific areas of the lung by coordinating the correct application routine as well as to prevent damage to the lung tissue from over or under pressurization.

A microcontroller or processor may be incorporated within the controller 16 and the microcontroller may be programmed with one or more routines for controlling the power, signals, pressure transmission, etc. through these interfaces in a way that creates the desired pressure distributions and substance transmission downstream to create density changes within the airways. The microcontroller may generally comprise a computer chip, microprocessor, processor, or system of computer chips that maintain a programmed routine, take inputs from external sources of electrical current and voltage, and produces signals using electrical current and voltage. This could include ROM, RAM, serial interfaces, I/O port interfaces, analog-to-digital converters, timers and other components. The ROM would store the pre-programmed or learned routine. The RAM would hold current tasks in memory. The serial interfaces would communicate with external computers and/or internal components such as stepper motors that control the position of the valves. The I/O port interfaces would sense voltage as a signal from the pressure sensor and other sensors and controls that would indicate a measurement or state change. For instance, if the user pushed a button on the control input user interface then the microcontroller would register this and enter another mode of the pre-programmed or learned sequence. The I/O port interfaces could also activate or deactivate components such as electrical relays that control the power to pump systems, imaging connectors that output to simple switch closure triggers, or indicator lights in the control input user interfaces. In an embodiment the controller 16 may be incorporated into a larger system of a bronchoscope or robotic endoscope. The controller 16 may be powered by battery power, a main source, or from an auxiliary power port of another device.

Embodiments of the controller's pre-programmed or learned routine are as follows: To begin the routine the controller 16 would wait for user input to begin the sequence. In another embodiment, the routine would begin based on input from a computer system. In another embodiment, the routine would begin based on input from an external computer system. Subsequently, the controller 16 would activate the transmission of pressure to the delivery sheath 12. In one embodiment, this pressure is a positive pressure transmitted through a gas such as air. In another embodiment, this pressure is a positive pressure transmitted through a liquid such as normal saline (0.9% saline). In one embodiment, this pressure is a negative pressure. In one embodiment, this pressure is transmitted through the opening of a valve. In another embodiment, this pressure is transmitted without the use of a valve and instead through direct modulation of the power to a pump.

Next, the controller 16 could measure the pressure within the lung. In one embodiment, this would be measured by a pressure-sensing device or transducer within the controller in which the pressure is measured through an open channel between the pressure-sensing device, the tube connector, the delivery sheath and the lung airways. In another embodiment, the pressure is measured through a pressure-sensing device mounted on or within the delivery sheath that measures pressure directly at the lung airways and transmits the pressure measurement through a wired voltage or serial connection to the controller. In another embodiment, this pressure measurement device is also mounted on or within the delivery sheath 12, but transmits the pressure measurement within the lung through a radio signal. In another embodiment, this pressure measurement is transmitted through a fiber-optic signal.

Next, once a predetermined pressure limit has been reached the controller 16 deactivates the transmission of pressure or substance through the delivery sheath. Next, in one embodiment, the controller 16 may signal to the external third party x-ray imaging machine that the imaging sequence should begin. Next, the controller 16 activates a second sequence of transmission of a positive or negative pressure in a manner that is the opposite of the first pressure transmission sequence. For instance, in one embodiment, the first pressure sequence is a negative pressure between −1 cm H2O and −150 cmH2O, and the second pressure sequence is a pressure between 0 cmH2O and 50 cmH2O relative to atmospheric. In another embodiment the second pressure sequence is equivalent to atmospheric pressure. This pressure is also applied until the pressure within the airways reaches a set or learned limit. Next, in one embodiment a set delay occurs. In another embodiment, a user-defined delay occurs until the user activates the user input controls. Next, in one embodiment the controller signals to the external third party x-ray imaging system to stop the imaging sequence.

Pump System

In one embodiment, the negative pressure suction pump and/or the positive pressure pump may be incorporated as an internal component of the controller 16. In another embodiment, the negative pressure suction pump and/or the positive pressure pump may be an external component (e.g. a hospital wall fixture supplying air and suction) for which activation, timing and pressure level, is modulated by the controller 16. Where the negative pressure suction pump and/or the positive pressure pump are external components, they are typically configured to provide a constant or nearly-constant source of pressure in which case the transmission of the pressures may be controlled by valves within the controller 16 which may limit, modulate, or stop the flow rate of substances or pressure resistance through the controller 16 and into the patient.

In embodiments where an internal pump is incorporated into the controller 16, any number of positive displacement pumps may be used, e.g., rotary vane pumps, diaphragm pumps, liquid ring pumps, piston pumps, scroll pumps, screw pumps, wankel pumps, external vane pumps, roots blowers, multistage Roots pumps, Toepler pumps, lobe pumps, or other types of positive displacement pumps), momentum transfer pumps, regenerative pumps, entrapment pumps (such as a cryopump, ion pump, sorption pump, non-evaporative getter pump or titanium sublimation pump), Venturi vacuum pump, steam ejector, or other types of vacuum pumps, etc. The pump could be used to create negative or positive pressures within the airways of the lung by removing or introducing air and/or saline (or other fluid) to the lungs.

Pump actuation could be triggered automatically through either manual triggering or through a signal from the x-ray system. The manual triggering could be selected by the user through a trigger associated with the delivery sheath, a triggering device or through the microcontroller. The automatic triggering signal could come from a component of the x-ray system (such as an acquisition pedal). The controller and pump system could be physically or wirelessly connected to the x-ray machine. Once triggered, the controller would initiate a sequence to modulate the actuation of the pump. For example, if a piston pump the controller would signal the piston to activate to create alternating positive and negative pressure. This sequence could be controlled manually or automatically. The manual sequence control could enable the user to control the piston with a control either on the microcontroller, the delivery sheath or an independent controller device. The automatic sequence control could involve feedback from pressure sensors, flow sensors, actuation sensors, distance sensors, imaging system feedback or any combination thereof. The pump system may include an air filter and humidifier for any air that might be pumped into the lungs.

For an external pump system, the valves controlling the flow could be triggered in a manner similar to the piston system. The degree of opening of the valves could modulate the amount of negative or positive pressure that would be imparted through the other components of the system. This pressure could be modulated using either manual control or automatic control. The manual control would enable the user to trigger negative pressure through a trigger associated with the delivery sheath, a triggering device or through the microcontroller. The automatic triggering signal could come from a component of the x-ray system (such as the acquisition pedal). Once triggered, the sequence and characteristics of the valve modulation could be controlled either automatically or manually. The manual modulation would enable the user to control the piston with a control either on the controller or the delivery sheath. The automatic sequence control would involve feedback from pressure sensors, flow sensors, actuation sensors, distance sensors, imaging system feedback, or any combination thereof.

The pump system could also comprise one or more pumps and these pumps may comprise a combination of gas, vacuum and/or fluid pumps. The pump system could also be comprised of an air pump or compressor to impart gas pressure where this air pump or compressor could be comprised of any number of mechanisms, e.g., bellows, air compressor, pre-pressurized tank, blower, etc. The air compressor could also be comprised of a positive displacement rotary mechanism (e.g., lobe, screw, liquid ring, scroll, vane), positive displacement reciprocating (e.g., diaphragm, double acting, single acting), or dynamic (e.g., centrifugal or axial).

Figure 10A:
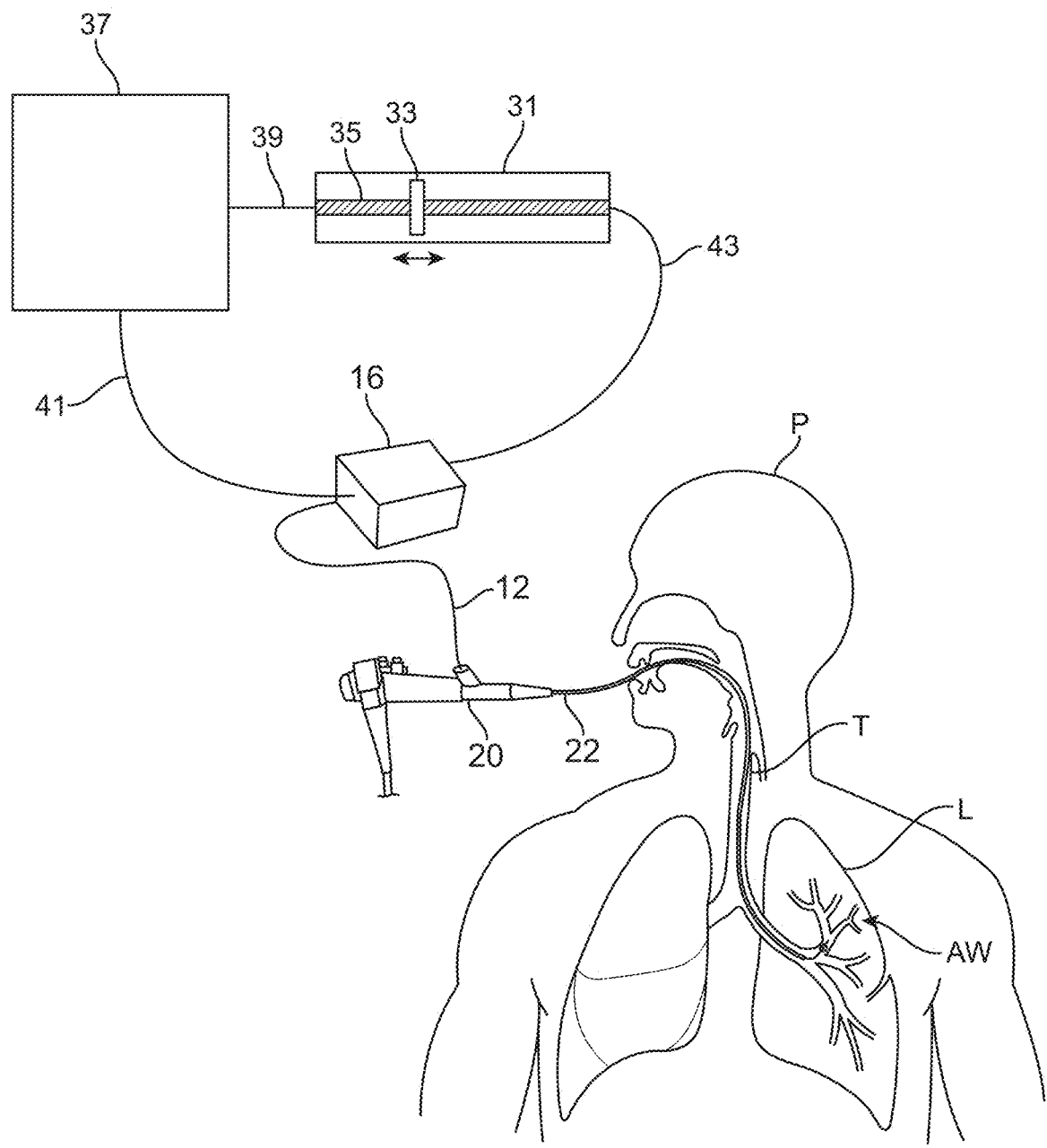
FIG. 10A shows an example in which a gas, such as air, may be infused and manipulated automatically within the airways.

FIG. 10A shows a schematic illustration of one example in which a gas, such as air, may be automatically infused and manipulated within the airways. This embodiment shows a reservoir body 31, such as a syringe, fluidly coupled via lumen 43 to the controller 16 for infusing and/or withdrawing fluids through the delivery sheath 12. The reservoir body 31 may have a piston 33 or other member such as a diaphragm sealed against the interior surface of the reservoir body 31. The piston 33 may be translated longitudinally upon a carriage 35, as indicated, via an actuator 37 (such as a motor) coupled to the carriage 35 and the actuator 37 may be electrically in communication through a wireless or wired interface 41 with the controller 16 for controlling an actuation of the actuator 37 and piston 33. In one embodiment, the piston 33 may be actuated to translate a relatively short distance at a preselected frequency (e.g., described herein) to impart a rapidly changing pressure wave for rapidly expanding and/or collapsing the airway walls within the lung. To prevent the piston 33 from imparting too great of a pressure differential, travel of the piston 33 may be limited either mechanically within the reservoir body 31 or via the actuator 37 and/or controller 16.

The piston 33 may accordingly be translated to create a positive and/or negative pressure wave within the reservoir body 31 for transmission through the delivery sheath 12 and into the airways AW. The amplitude of the pressure waves and the frequency of the pressure waves may be selected and controlled via the actuator 37 and/or controller 16 to ensure that threshold levels of pressure are not exceeded but maintained within a prescribed range, as described in detail below.

In another variation, rather than a piston 33, a diaphragm may be positioned within the reservoir body 31 attached around its circumference. This diaphragm may be actuated via the actuator 37, e.g., to displace in a distal-proximal motion to impart the pressure differential into the airways AW.

Figure 10B:
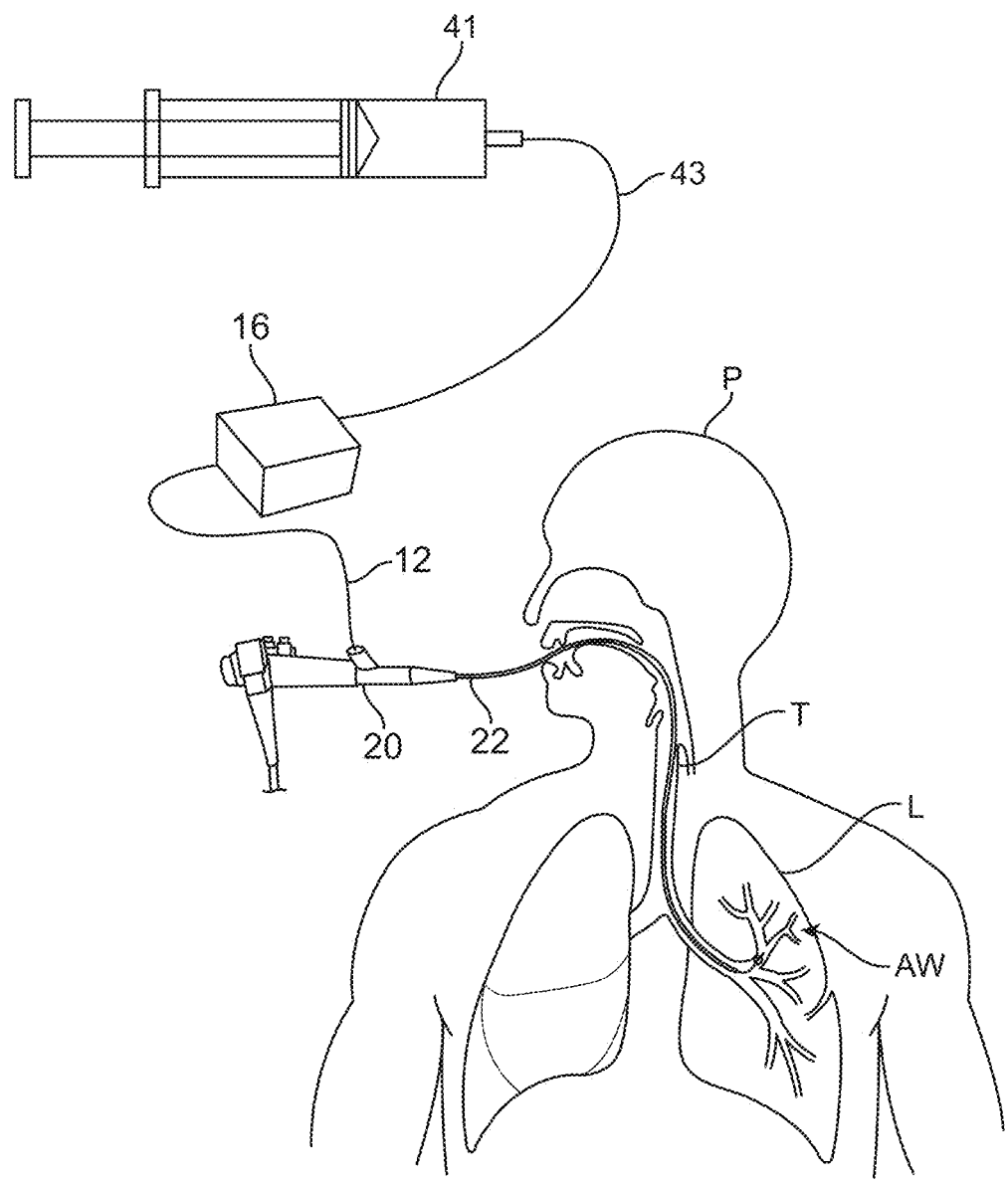
FIG. 10B shows another example in which a gas, such as air, may be manually infused and manipulated within the airways.
Figure 11A:
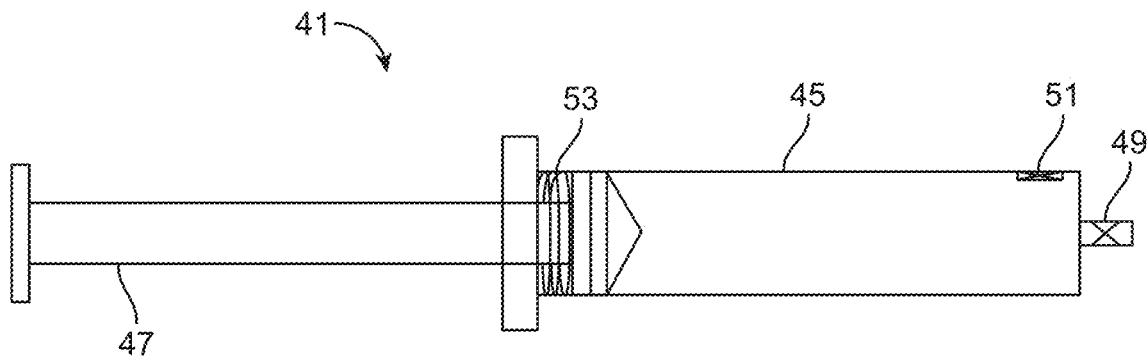
FIGS. 11A to 11C show side views of one variation of a syringe from FIG. 10B which may be used to manually infuse the airways.
Figure 11B:
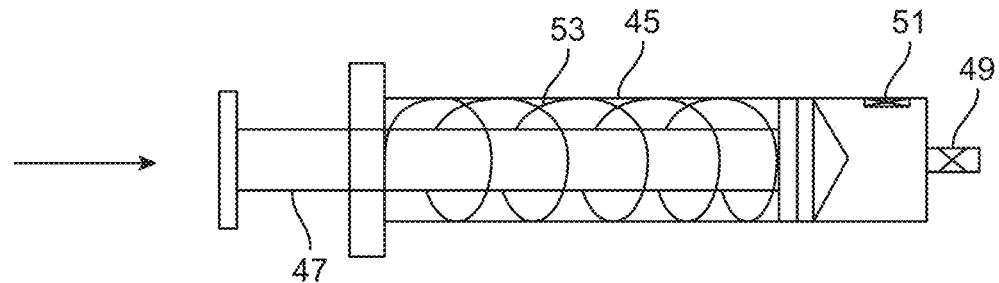
Figure 11C:
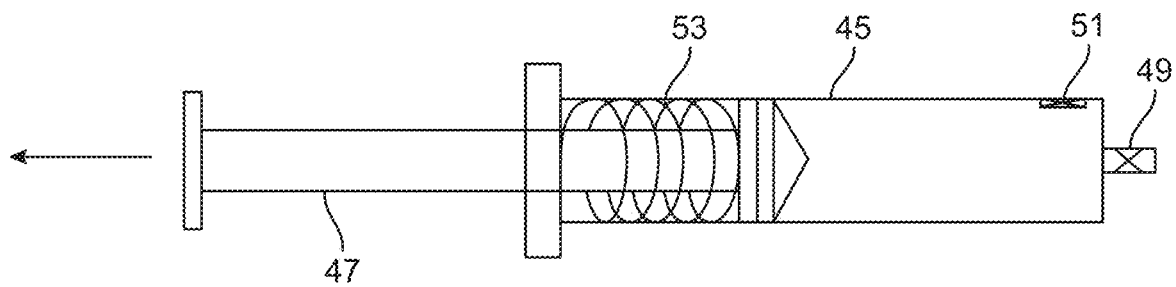

With respect to a manually actuated pumping system, FIG. 10B shows a schematic illustration of one example in which a gas, such as air, may be manually infused and manipulated within the airways. A handheld actuator such as a syringe 41 may be fluidly coupled via lumen 43 to the controller 16 or directly to the delivery sheath 12 such that air within the syringe 41 may be infused manually through the delivery sheath 12 and into the airways AW within the lung L. FIGS. 11A to 11C show side views of one variation of the syringe 41 in which the plunger 47 may incorporate a biasing element 53 such as a spring within the barrel 45 (or externally of the barrel 45). The syringe 41 may also incorporate a valve 49 configured to intermittently open and close (such as a flutter valve) as well as a safety valve 51 positioned near a distal end of the barrel 45 where the safety valve 51 may be configured to open or release at a maximum predetermined cracking pressure such as 50 cm H20 maximum. In other variations, the valve 49 may be controlled via the controller to open and close intermittently.

In use, the plunger 47 may be withdrawn and the biasing element 53 may be in its relaxed state, as shown in FIG. 11A. As the plunger 47 is advanced distally, as shown in FIG. 11B, air may be forced through the delivery sheath 12 and into the airways AW while the valve 49 intermittently opens and closes as the air passes through the valve to create pressure waves which are transmitted into the airways AW. In the event that the pressure within the barrel 45 exceeds the cracking pressure (e.g. 50 cm H20), safety valve 51 may open to expel the pressurized air from the barrel 45. In this state, the biasing element 53 is displaced and in its high energy state. The plunger 47 may be released allowing for it to be drawn proximally, as shown in FIG. 11C, by the biasing element 53. As the plunger 47 is withdrawn proximally, syringe 41 may create a suctioning force to withdraw the air within the airways while also creating pressure waves due to the valve 49 intermittently opening and closing. The suction pressure will not exceed −100 cm H20.

Controller Embodiments

Various embodiments of the controller are provided as examples but the features and components of each controller described in one embodiment may perform the same or similar function in another controller embodiment. Different features and components may be combined in any number of combinations within a single controller and are considered within the scope of this description.

Figure 12:
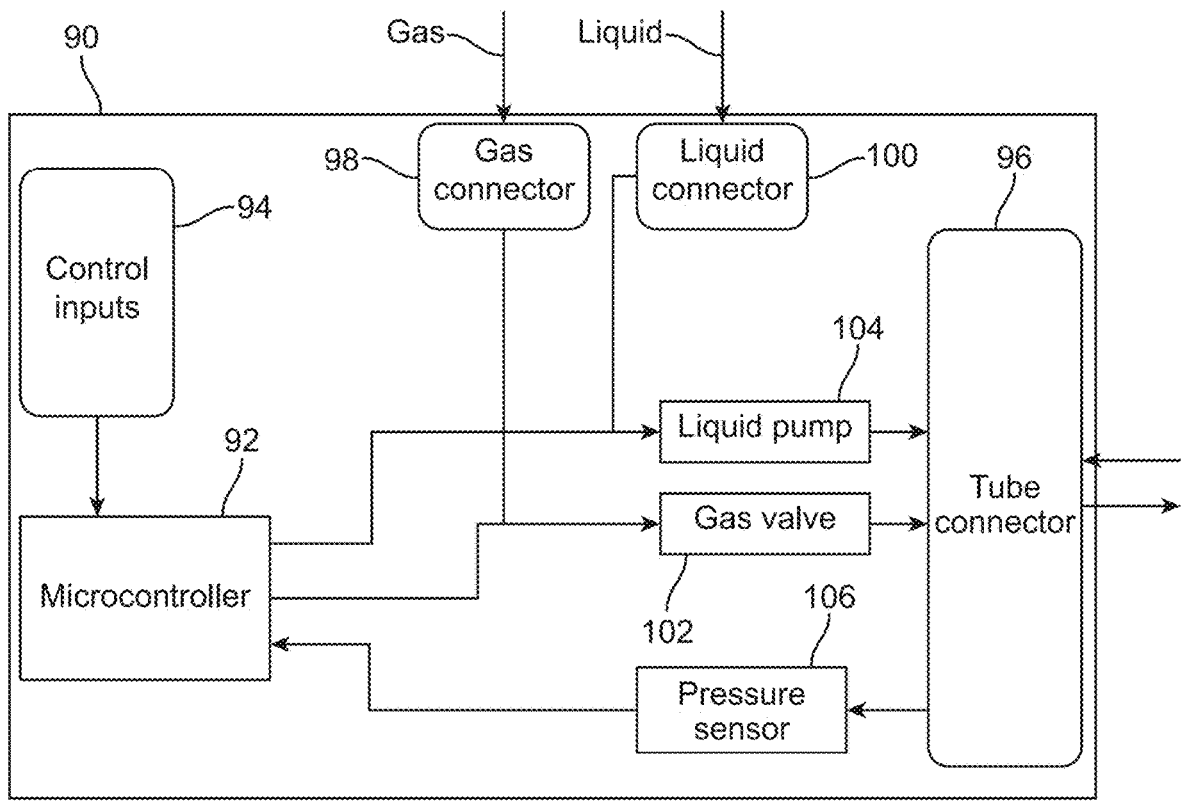
FIGS. 12 to 24 show schematic illustrations of various embodiments of the controller.

FIG. 12 shows one variation of a controller 90 embodiment which may be fluidly coupled to the delivery sheath 12 via tube connector 96. The various control parameters may be input into the controller 90 via control inputs 94 which may be in communication with the microcontroller 92. Various outputs such as active control parameters and other alerts or indications may also be displayed upon the control inputs 94 or upon an external monitor or display which is in communication with the controller 90. In this variation, the controller 90 may be fluidly coupled to an external gas source (as described herein) via gas connector 98 to provide for an infusion of gas or air into the localized airways of interest. The gas received through gas connector 98 may be flowed into the delivery sheath 12 through the tube connector 96 while the infusion is controlled via gas valve 102 (as described herein) which may be controlled via the microcontroller 92. Controller 90 may also be fluidly coupled to an external source of liquid (e.g., saline) via liquid connector 100 which may be introduced through the delivery sheath 12 also via the tube connector 96 where the infusion of the isolation component 14 is controlled via a liquid pump 104 (as described herein) in communication with the microcontroller 92. The controller 90 may also incorporate a pressure sensor 106 which may receive pressure information from the delivery sheath 12 via the tube connector 96. The pressure sensor 106 may also be in communication with the microcontroller 92, as shown. The microcontroller 92 may receive the pressure information from the patient via the pressure sensor 106 and with this information may adjust the flow of gas via gas valve 102 and liquid via liquid pump 104 accordingly.

Figure 13:
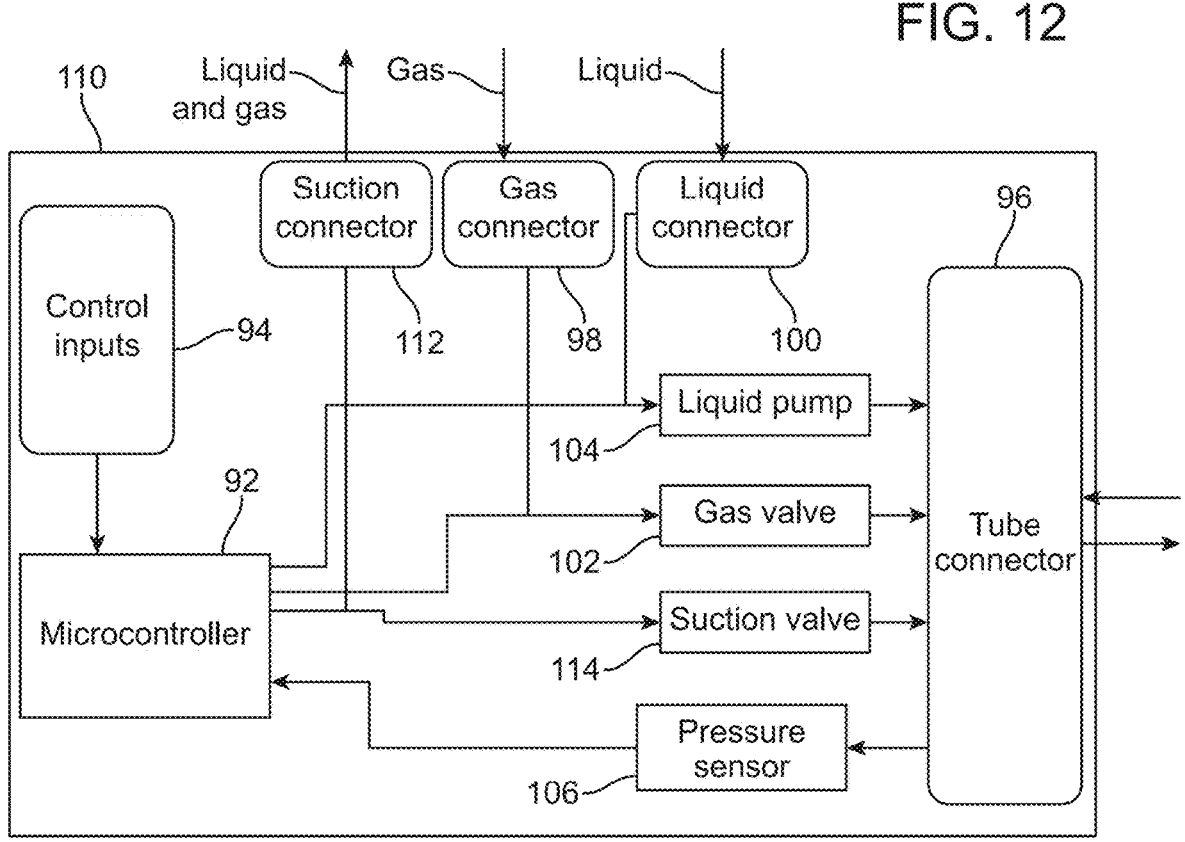

FIG. 13 shows another variation of a controller 110 which incorporates the gas connector 98 and liquid connector 100 but also incorporates a suction connector 112 relative to the embodiment of controller 90 shown above. The suction connector 112 is fluidly coupled to the tube connector 96 through a suction valve 114 which is also in communication with the microcontroller 92. This controller embodiment may allow for the controlled suctioning of liquids and gases from the airways AW of the patient P, e.g., to collapse the airways AW of interest for imaging.

Figure 14:
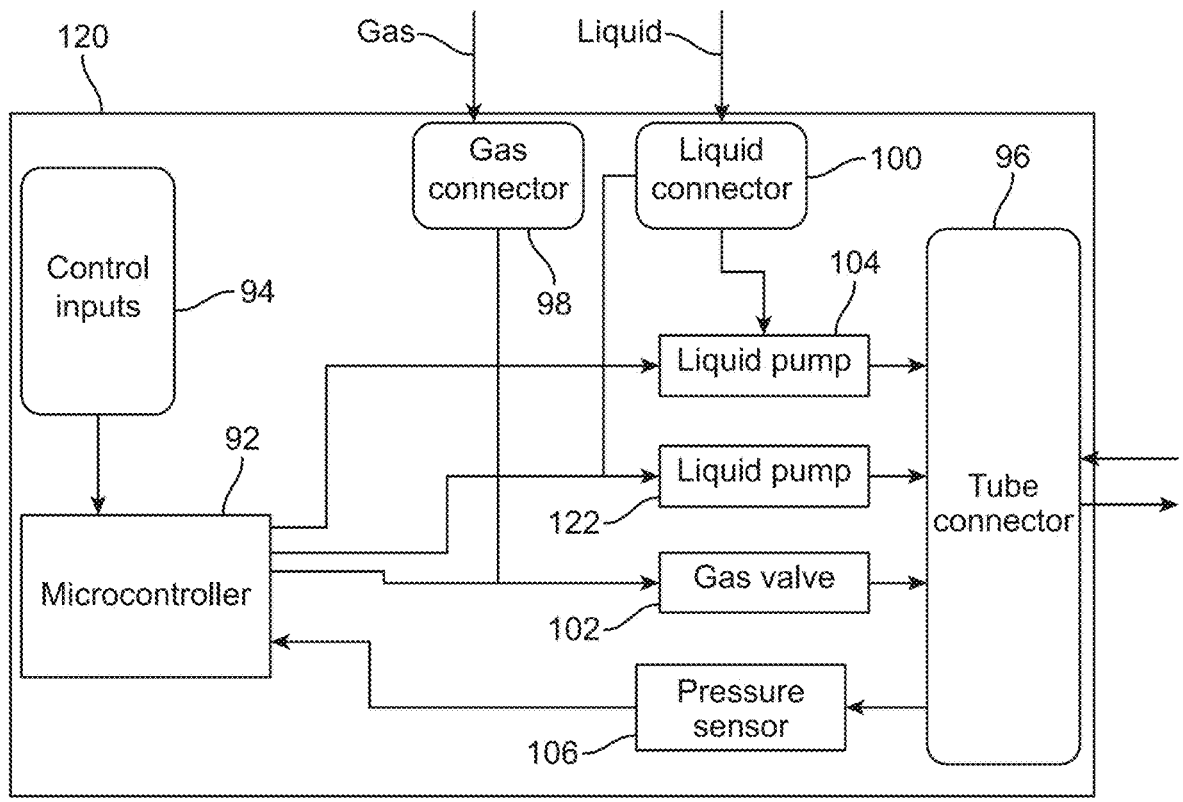

FIG. 14 shows yet another variation of a controller 120 which may incorporate a second liquid pump 122 in addition to liquid pump 104 relative to the controller embodiments shown above. The second liquid pump 122 may be fluidly coupled to liquid connector 100 along with liquid pump 104 and may be utilized to provide inflation fluid to the isolation component 14 or to provide an inflation fluid for the airways AW as well.

Figure 15:
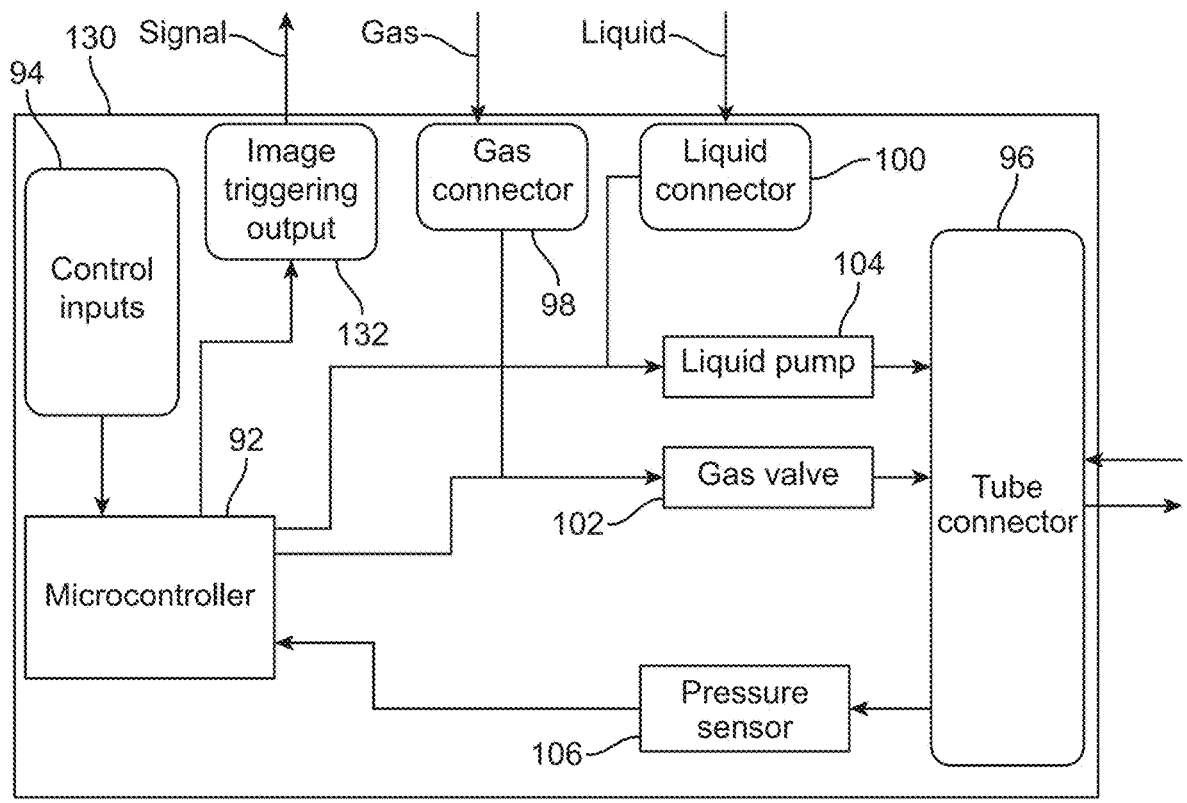

FIG. 15 shows yet another variation of a controller 130 which may incorporate an image triggering output 132 connector in communication with the microcontroller 92 for providing a triggering or gating signal to, e.g., an external imaging assembly, used to image the airways AW of interest which are altered in tissue density via controller 130 relative to the controller embodiments shown above. The microcontroller 92 may receive pressure signals from the pressure sensor 106 and control the infusion of liquid via liquid pump 104 as well as infusion of gas or air via gas valve 102. Depending upon the parameters received and the infusion (or suction) frequency of the gas or air within the airways AW, signals may be sent via the microcontroller 92 through the image triggering output 132 to the imaging assembly to image the airways AW at corresponding times to capture the change in density of the airway tissues in order to time the resulting images, as described in further detail herein.

Figure 16:
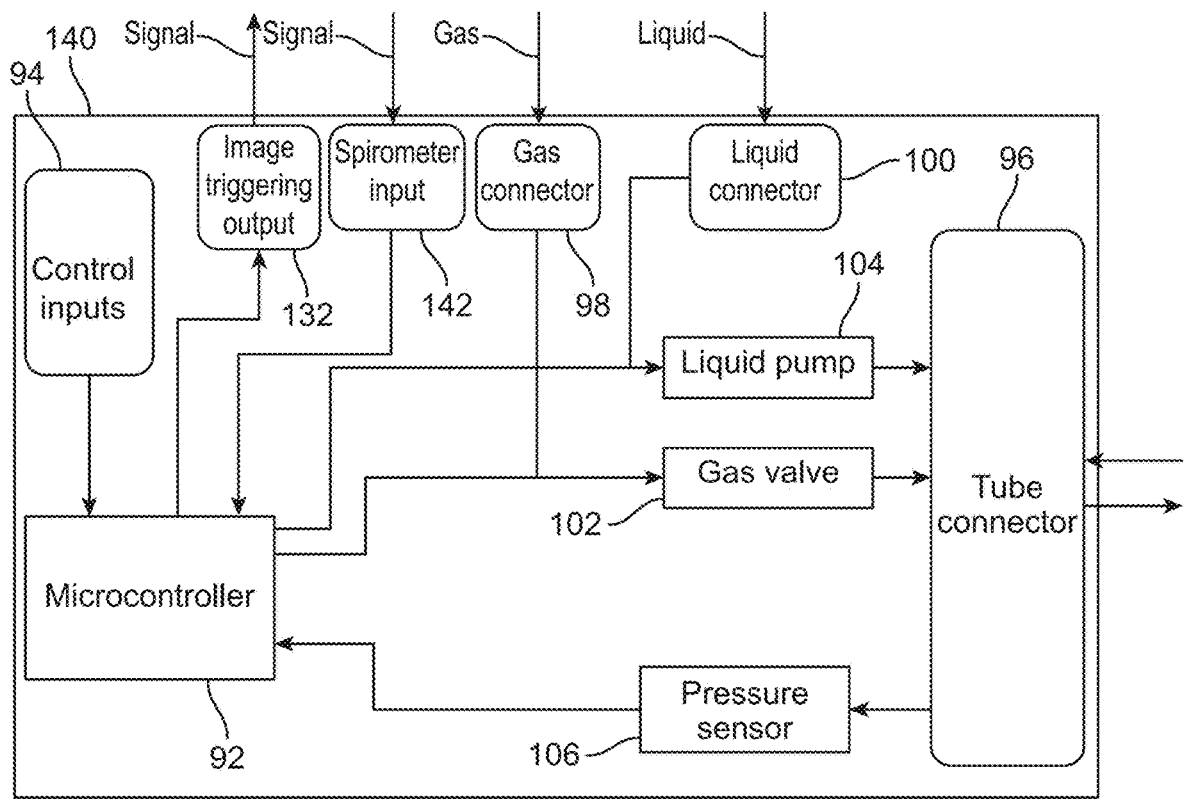

FIG. 16 shows yet another variation of a controller 140 which may further incorporate a spirometer input 142 in communication with the microcontroller 92 relative to the controller embodiments shown above. An external spirometer may be placed into communication with the microcontroller 92 through spirometer input 142 in order receive spirometry data from the patient. This spirometry data may be received by the microcontroller 92 which may also receive pressure data from pressure sensor 106 and provide a triggering or gating signal via image triggering output 132 to the imaging assembly in communication with the controller 140.

Figure 17:
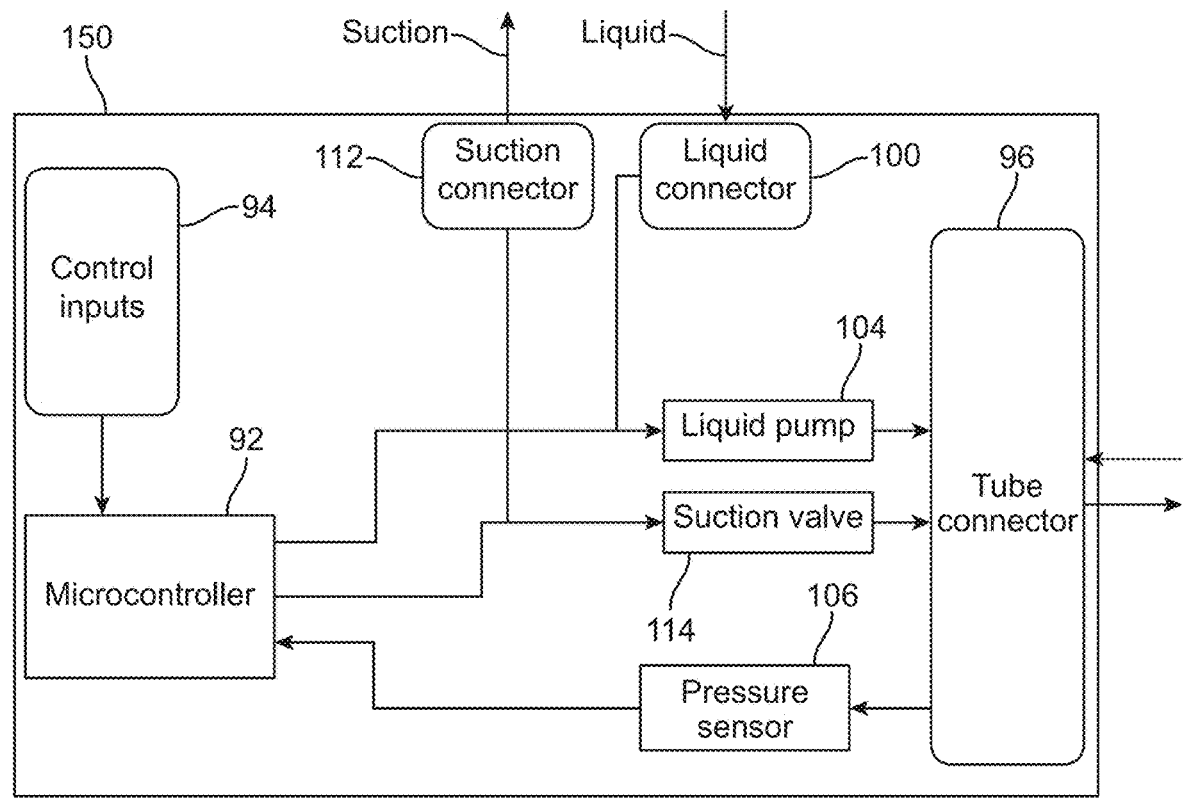

FIG. 17 shows yet another variation of a controller 150 which may incorporate a liquid connector 100 in combination with a suction connector 112 relative to the controller embodiments shown above. The microcontroller 92 may receive signals from the pressure sensor 106 and control inputs 94 and provide a negative pressure or suction via suction valve 114 to control the removal of air or fluids from the airways AW for imaging.

Figure 18:
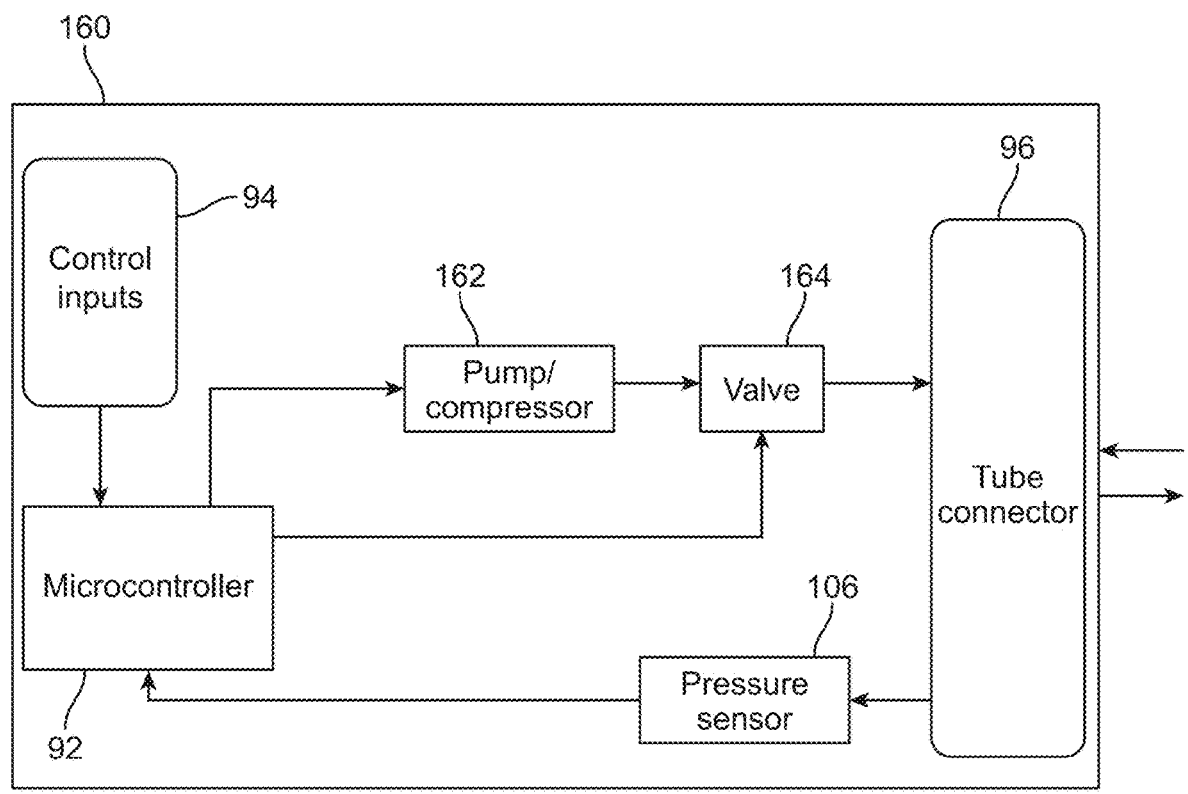

FIG. 18 shows yet another variation of a controller 160 which may directly incorporate a pump/compressor 162 in fluid communication with the tube connector 96 through valve 164 relative to the controller embodiments shown above. The microcontroller 92 may be in communication with both the pump/compressor 162 as well as the valve 164 to control the actuation of the pump/compressor 162 as well as flow through the valve 164.

Figure 19:
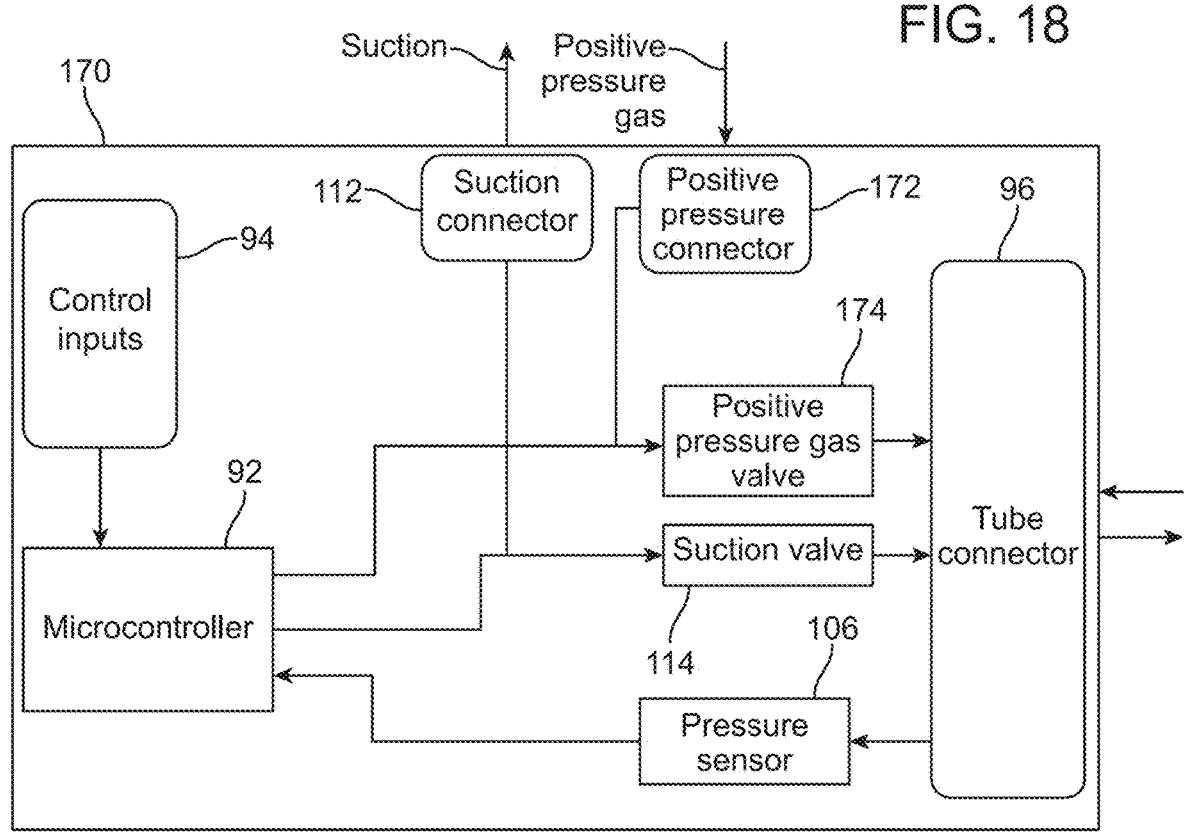

FIG. 19 shows yet another variation of a controller 170 which may incorporate a positive pressure connector 172 in communication with the tube connector 96 via a positive pressure gas valve 174 relative to the controller embodiments shown above. The controller 170 may also incorporate a suction connector 112 as well and the gas valve 174 may be in communication with the microcontroller 92.

Figure 20:
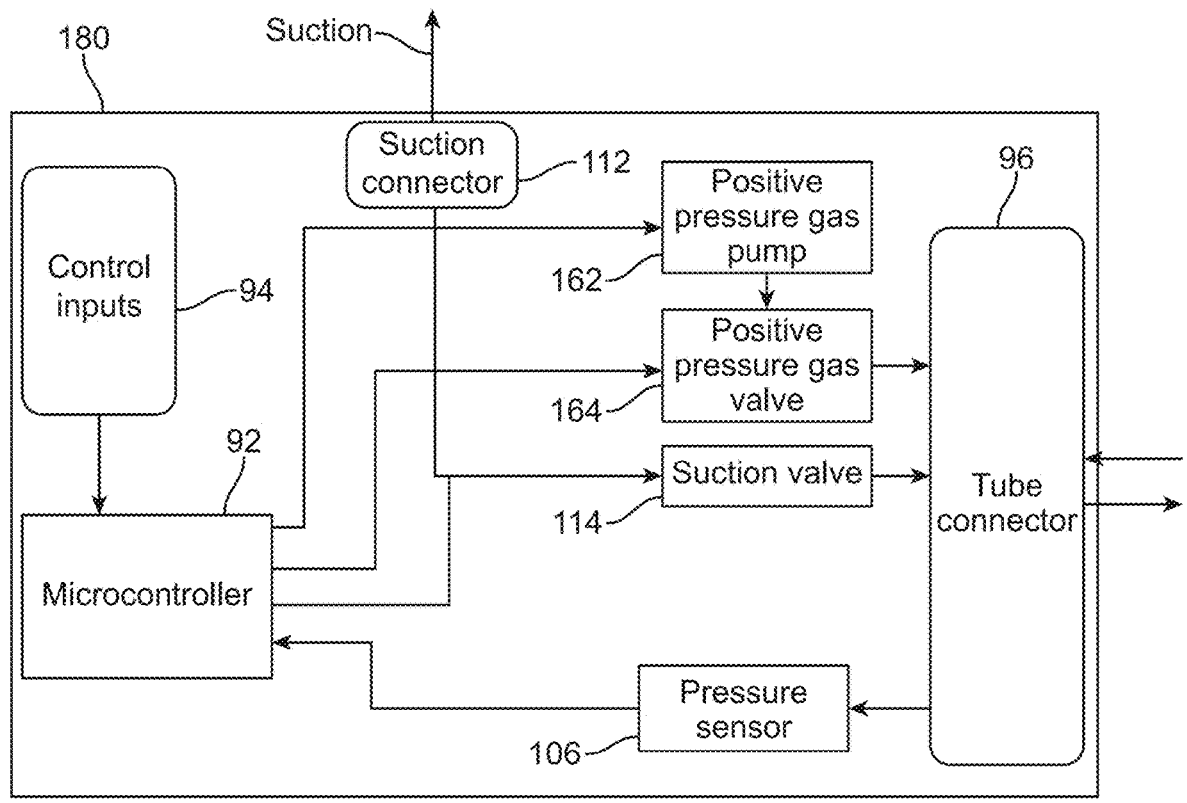

FIG. 20 shows yet another variation of a controller 180 which may incorporate a suction connector 112 in communication with suction valve 114 in combination with a positive pressure gas pump 162 in communication with the tube connector 96 through a positive pressure gas valve 164 relative to the controller embodiments shown above.

Figure 21A:
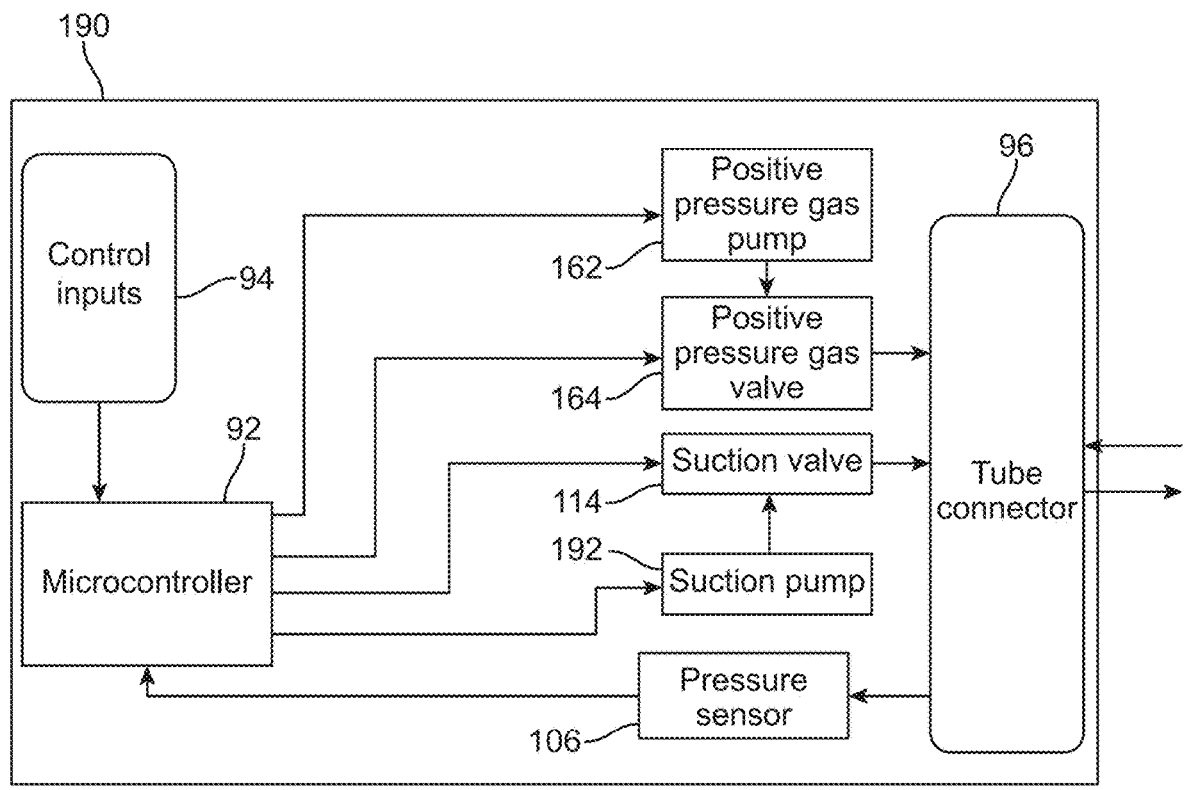

FIG. 21A shows yet another variation of a controller 190 which may incorporate a positive pressure gas pump 162 in communication with a positive pressure gas valve 164 in combination with a suction pump 192 in communication with suction valve 114. Both the pump 162 and suction pump 192 may be in communication with the microcontroller 92.

Figure 21C:
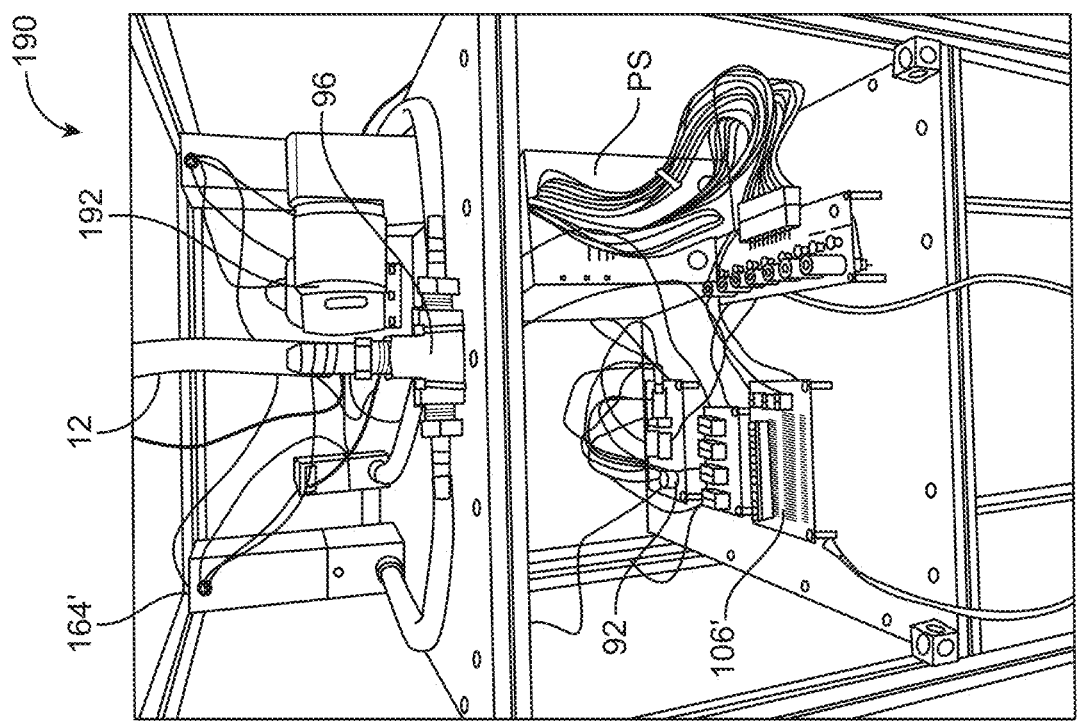
Figure 21B:
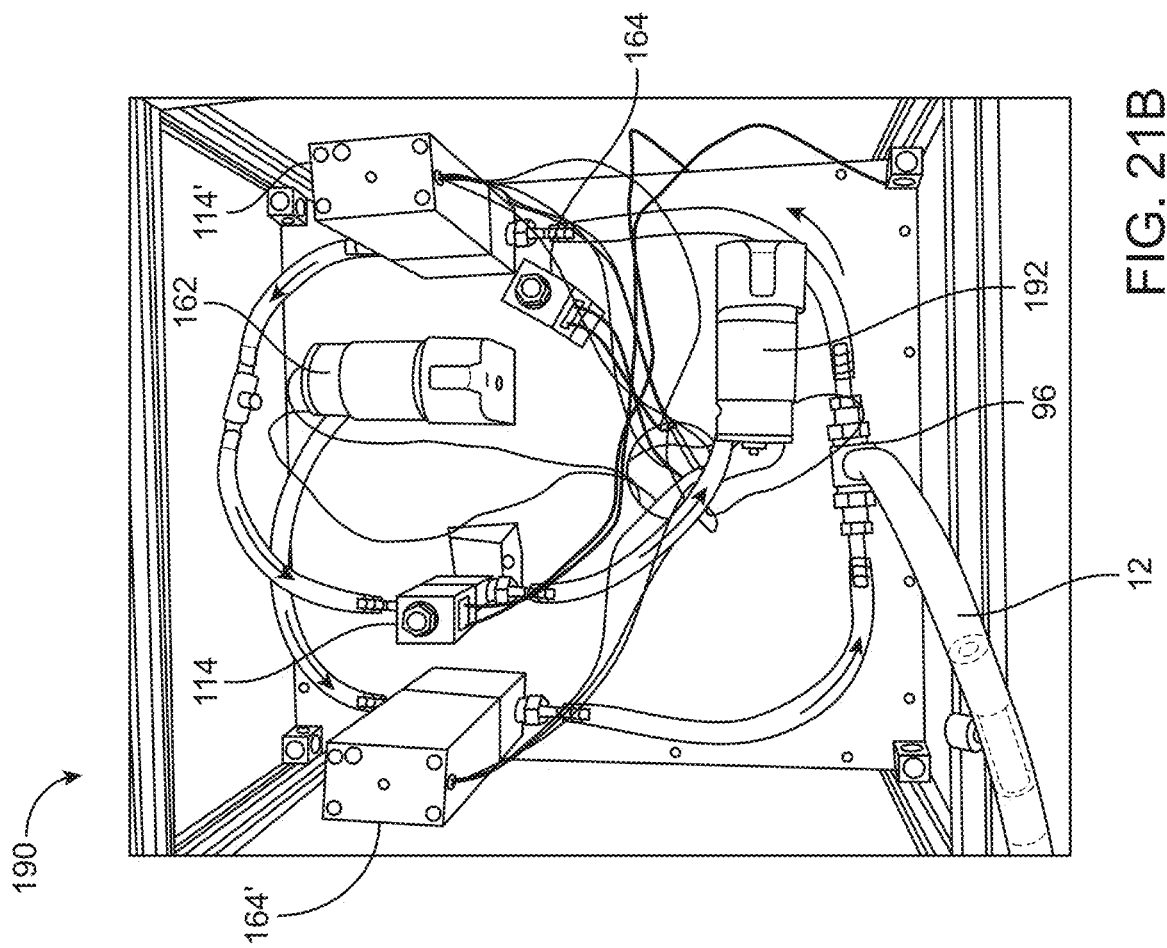

FIGS. 21B and 21C show perspective views of an embodiment of the controller incorporating the features shown above in FIG. 21A. For instance, components of the controller 190 is shown in the perspective view of FIG. 21B illustrating an embodiment of the positive pressure gas pump 162 which is fluidly coupled with a positive pressure gas valve 164, e.g., a solenoid valve. A positive pressure regulator 164' is also shown as being fluidly coupled to the positive pressure gas pump 162 and is further fluidly coupled to tube connector 96 which in turn is fluid coupled to the delivery sheath 12. The arrows illustrate the flow of gas from the positive pressure gas pump 162 and ultimately to through the tube connector 96 and to the delivery sheath.

The suction pump 192 is also shown in fluid communication with the suction valve 114, e.g., a solenoid valve, and a negative pressure regulator 114'. The regulator 114' may be in fluid communication with the tube connector 96, as illustrated. As with the positive pressure flow, the arrows indicate the direction of gas flow when the suction pump 192 is actuated to induce a negative pressure through the delivery sheath 12, through the negative pressure regulator 114', through the suction valve 114, and through the suction pump 192.

FIG. 21C shows a perspective view of the microcontroller 92 in electrical communication with each of the components described and shown. A pressure sensor connector 106' is illustrated for electrical connection to the pressure sensor 106 which may be located either within the controller 190 or delivery sheath 12. A power supply PS is also shown for electrical connection to the components within the controller 190. Although the controller 190 is illustrated as separate components, all or some of the components may be enclosed within a singular housing unit or separate housing units, as illustrated in FIG. 21D and above in FIG. 1.

Figure 21D:
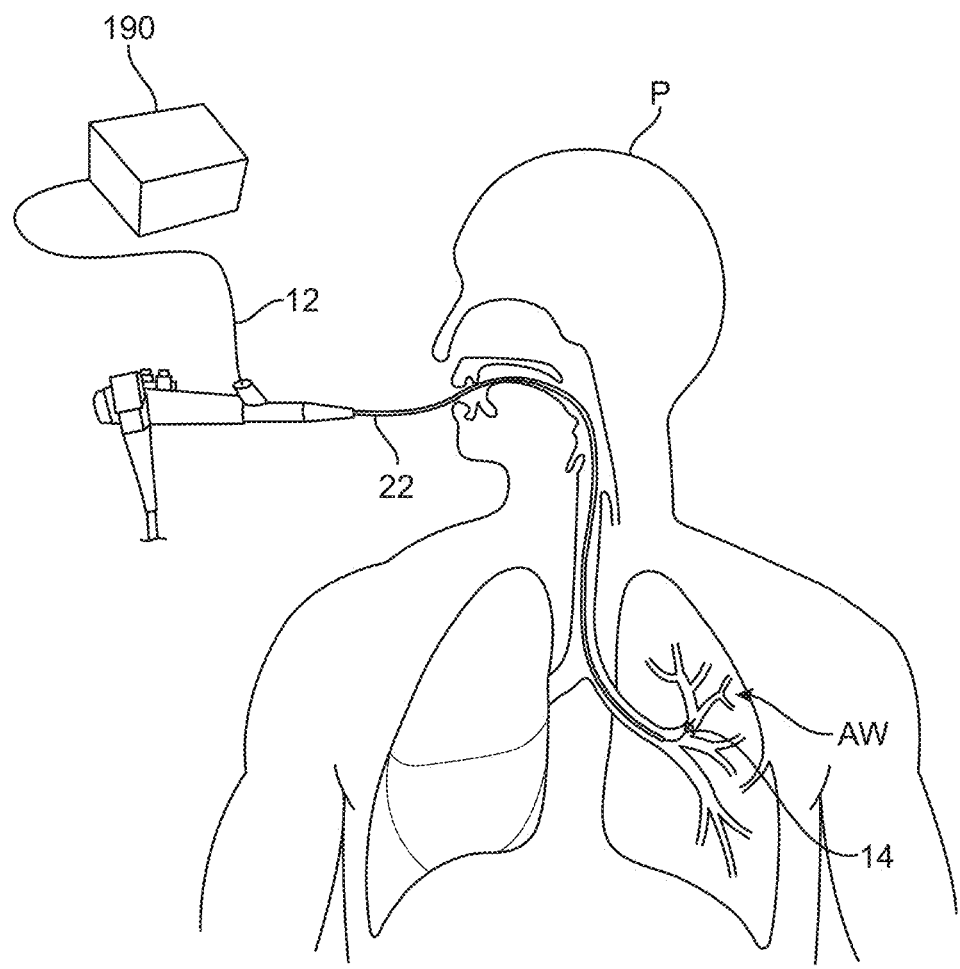
Figure 45A:
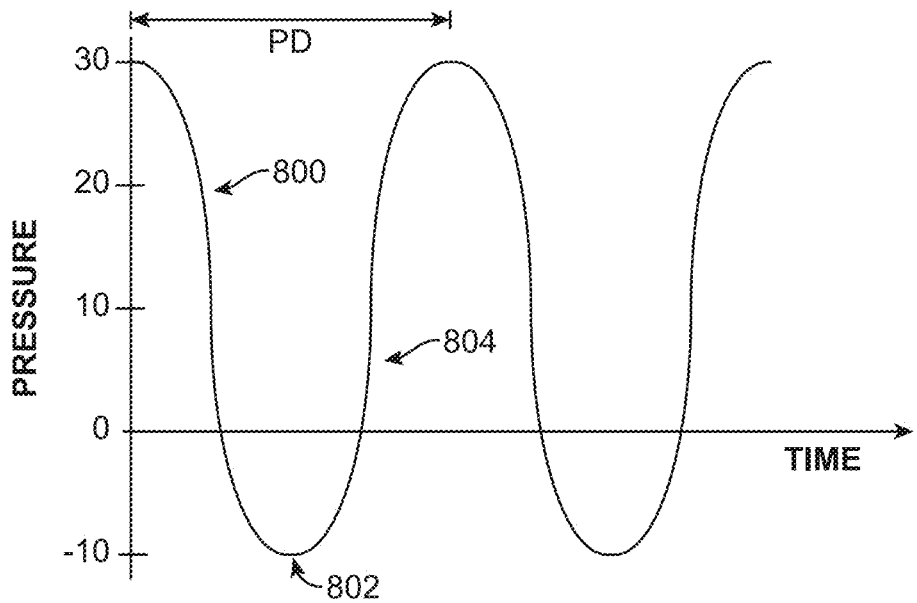
FIGS. 45A to 45C show graphs illustrating examples of how the pressures may be applied to cycle between a maximum and minimum pressure level.
Figure 45B:
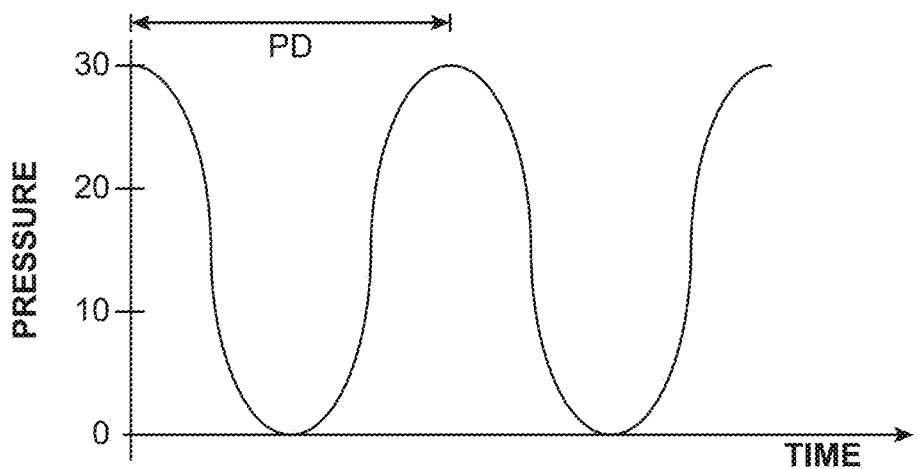
Figure 45C:
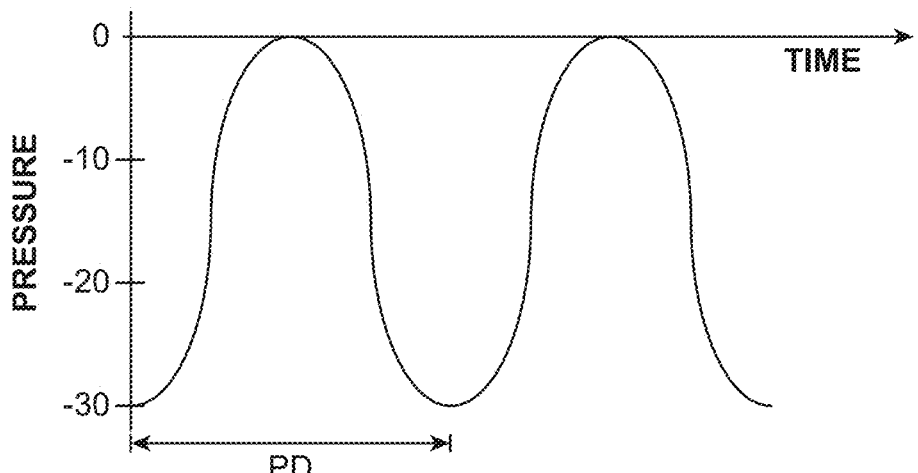

Furthermore, the microcontroller 92 in controller 190 may be programmed to impart pressure changes to the airways AW utilizing the application of the maximum pressure and minimum pressure, waveform shapes (e.g. square or sine waves) and frequency of cycling between maximum and minimum pressures, as illustrated in the graphs of FIGS. 45A to 45C and described below in further detail, as illustrated in FIG. 21D.

Figure 22:
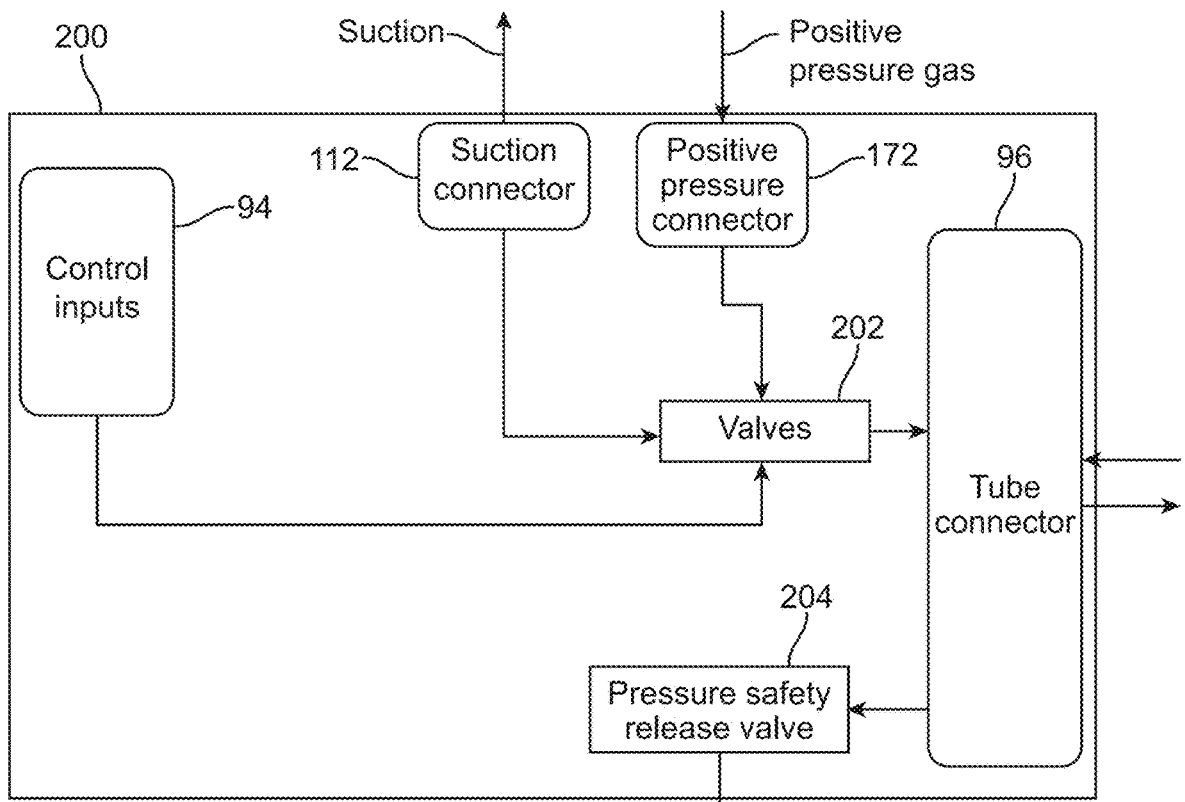

FIG. 22 shows yet another variation of a controller 200 which may incorporate a suction connector 112 and a positive pressure connector 172 in fluid communication with one or more valves 202 which is also in direct communication with the control inputs 94. The one or more valves 202 may directly control the suction and/or positive pressure through the tube connector 96 and delivery sheath 12. A pressure safety release valve 204 may be fluidly coupled directly to the tube connector 96 as a safety measure to prevent suction pressure from dropping below a threshold level, e.g., −150 cmH2O, or to prevent positive pressure gas from exceeding a threshold level, e.g., 50 cmH2O.

Figure 23:
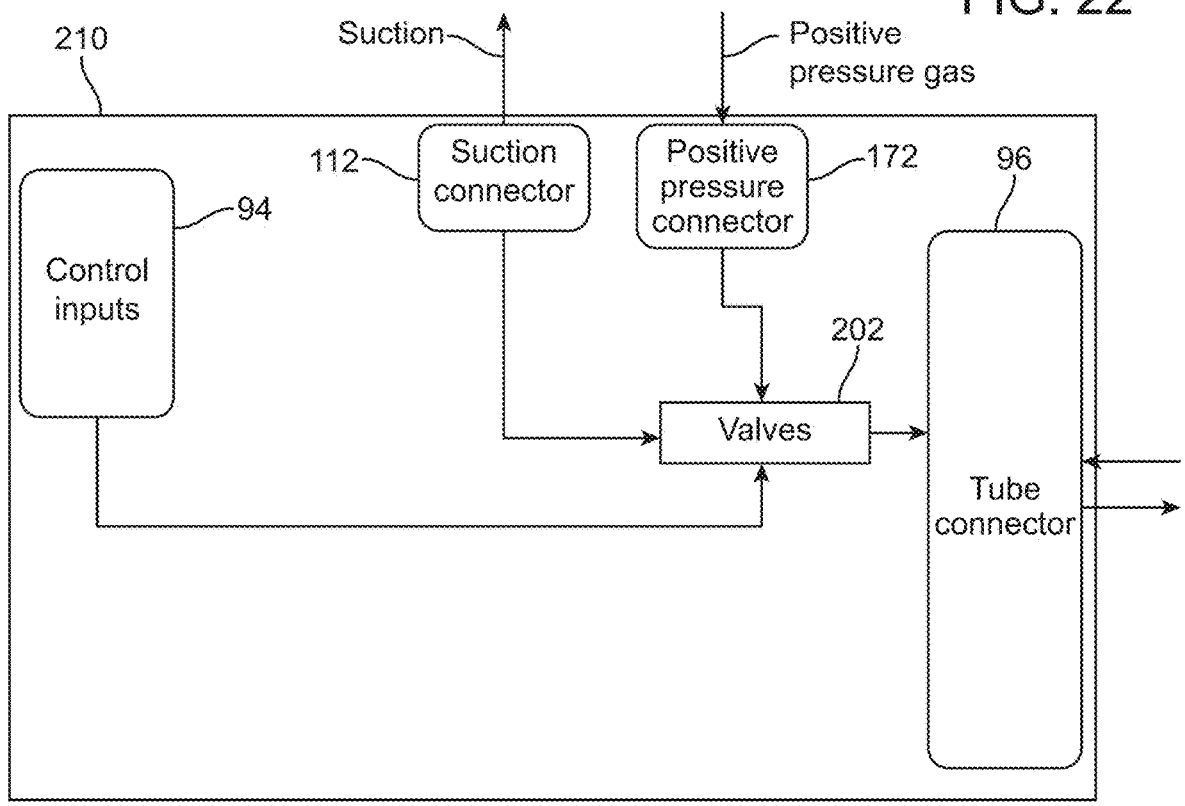

FIG. 23 shows yet another variation of a controller 210 which may incorporate a suction connector 112 and a positive pressure connector 172 in fluid communication with one or more valves 202 which is also in direct communication with the control inputs 94, as described above. In this variation, the pressure safety release valve 204 may be omitted from the controller 210.

Figure 24:
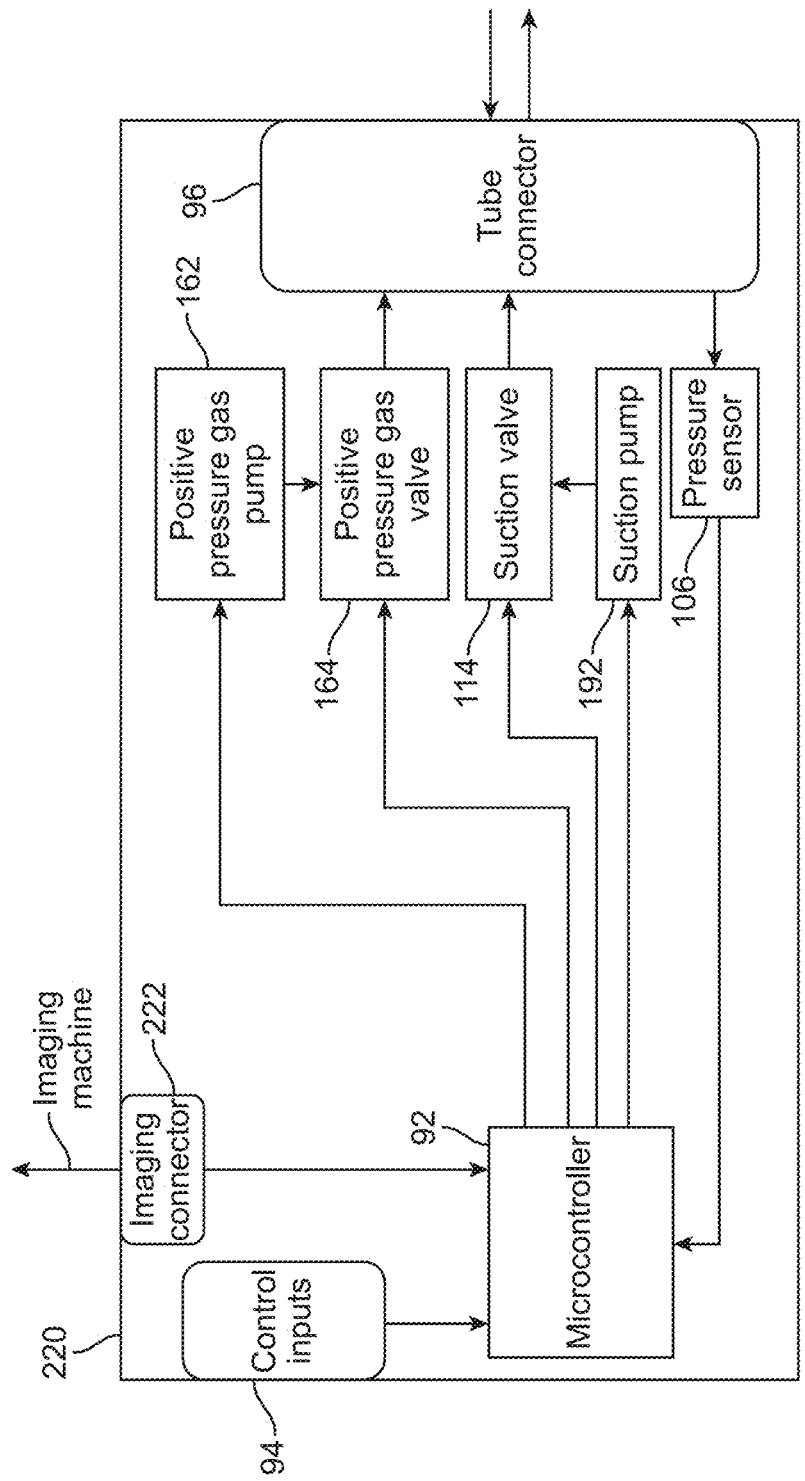

FIG. 24 shows yet another variation of a controller 220 which incorporates a combination of the positive pressure gas pump 162 in communication with the tube connector 96 via the positive pressure gas valve 164, and suction pump 192 in communication with the tube connector 96 via the suction valve 114. The microcontroller 92 is in communication with each of the positive pressure gas pump 162, positive pressure gas valve 164, suction pump 192, and suction valve 114. The microcontroller 92 may also be in communication with the imaging connector 222 and control inputs 94 such that the microcontroller 92 may control an output to an external imager to enable the controller, e.g., to trigger or gate the imaging assembly and/or synchronize the imager with the functionality of the controller 220.

As previously discussed, the various embodiments of the controller are provided as examples but the features and components of each controller described in one embodiment may perform the same or similar function in another controller embodiment. Different features and components may be combined in any number of combinations within a single controller and are considered within the scope of this description.

EXAMPLES

Utilizing any of the controller embodiments and system features described herein, the system may image the airways of interest by providing a suction or infusion of a gas such as air or a liquid such as saline to temporarily alter the density of the airway tissues, as described herein. The imaging system may take advantage of the local tissue density changes relative to the remainder of the lung which remains unchanged by imaging the airways of interest as the tissue density changes.

Figure 25A:
FIG. 25A shows an illustration of an x-ray image from a human cadaver lung in which negative pressure was applied to increase the density of only the airways.

Examples of the imaging results may be seen in FIG. 25A which illustrates an x-ray image 230 of the experimental results from a lung of a human cadaver in which a negative pressure was applied to increase the density of only the airways relative to the background lung tissue while x-ray imaging was performed. As shown, the airways may be seen as the relatively darker branching structures which would otherwise not be visible for x-ray imaging. In this example, a delivery sheath was advanced to a region of interest in the right lung. An isolation component was deployed in the trachea of the lung. The controller settings were max pressure of 25 cm H20, minimum pressure of 0 cm H20 and frequency of 0.5 Hz. The controller initially activated the positive pressure pump to a level of 25 cm H20, expanding the airways. Once achieved, the positive pressure was terminated, x-ray imaging with subtraction processing was initiated and the negative pressure suction was activated to bring the pressure down to 0 cm H20. The airways then collapsed which is displayed as dark branching airways.

Figure 25B:
FIG. 25B shows an illustration of the human cadaver lung from FIG. 25A but imaged after injection of liquid iodinated contrast as a control for comparison purposes against an x-ray image using the methods described herein which does not use contrast.

FIG. 25B shows an x-ray image 232 of the same human cadaver lung from FIG. 25A but imaged using contrast as a control for comparison purposes against x-ray images using the methods described herein which does not use contrast. When compared against, for example, the image shown in FIG. 25A which was imaged utilizing the density alteration methods described herein, the images obtained utilizing density changes are comparable to the image of FIG. 25B but without having to utilize any contrast agent.

Figure 25C:
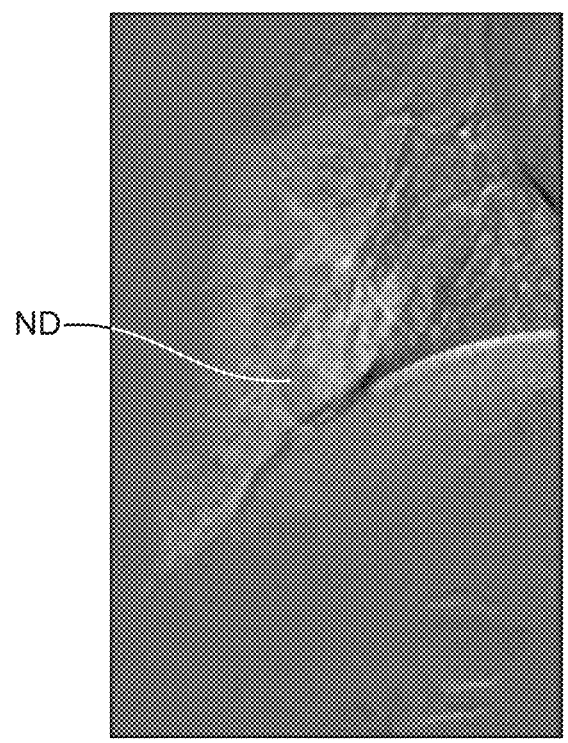
FIG. 25C shows an illustration of a lung nodule imaged via x-ray using the airway density change methods described herein.

FIG. 25C shows an example of an x-ray image showing the presence of a lung nodule ND which was imaged using the density alternation methods described. In this particular example, the controller was configured to apply a minimum negative pressure of −30 cm H20 which, once reached, terminated the negative pressure, initiated x-ray imaging, and applied positive pressure to 20 cm H20 to fully expand the alveolar tissue around the nodule ND. While the nodule ND itself does not change in density during the airway alternation, the surrounding lung tissue may appear as a white image upon subtraction processing enhancement. The resulting image shows the nodule ND as a dark structure on a light background.

Figure 26A:
FIGS. 26A to 26C show x-ray images of an in vivo porcine model in which the airways become visible after density changes to the airways and density change enhancement with subtraction image processing have been applied.
Figure 26C:
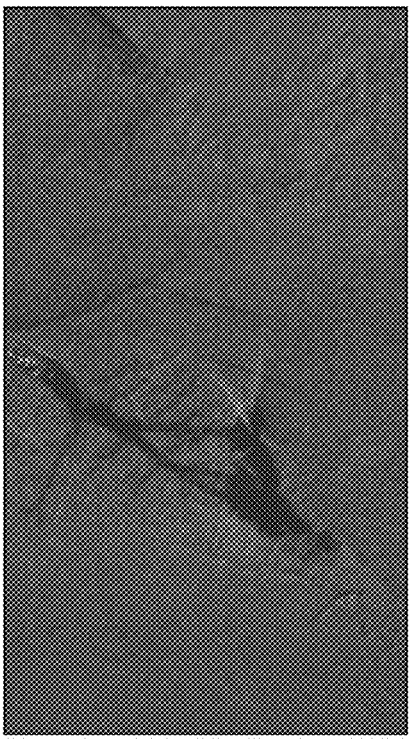
Figure 26B:
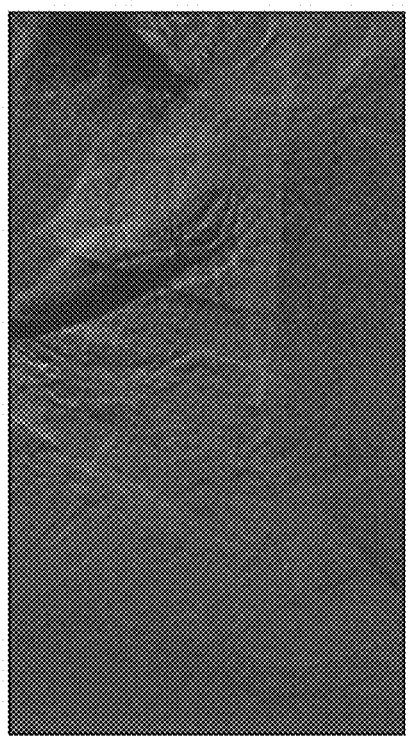

FIGS. 26A to 26C show x-ray images of a right lung of an in vivo porcine model. In this example, a steerable delivery sheath with 10 mm diameter expandable balloon isolating component was used to fluidly isolate the lung segment of interest. The same controller routine that was performed on the previous example was performed on the in vivo image. An initial x-ray image taken of a live porcine lung may be seen in image 240 of FIG. 26A before any density changes have been applied to the airways which are not visible on this x-ray image 240. FIG. 26B shows the image 242 taken after subtraction processing enhancement has been applied but prior to any airway density changes such that the airways are still not visible. FIG. 26C shows the image 244 after the negative pressure component of the controller cycle was applied to increase tissue density of the airways relative to the background lung tissue. The airways are now visible as relatively darker branching structures on x-ray subtraction imaging utilizing the methods described herein.

FIGS. 27A to 27C show x-ray images of a left lung of an in vivo porcine model. In this example, a steerable delivery sheath with 10 mm diameter expandable balloon isolating component was used to fluidly isolate the lung segment of interest. A similar controller routine that was performed on the previous examples was performed on the in vivo image. An initial unsubtracted x-ray image taken of a live porcine lung may be seen in image 250 of FIG. 27A before any density changes have been applied to the airways which are not visible on this x-ray image 250. FIG. 27B shows the image 252 taken after subtraction processing enhancement has been applied but prior to any airway density changes such that the airways are still not visible. FIG. 27C shows the image 254 after the negative pressure component of the controller cycle was applied to increase tissue density of the airways relative to the background lung tissue. The airways are now visible as relatively darker branching structures on x-ray subtraction imaging utilizing the methods described herein.

Figure 28:
FIG. 28 shows an illustration of an x-ray image from an ex vivo porcine lung where the density of the airway of interest was decreased with positive pressure expansion of the airway.

FIG. 28 shows an experimental result from an ex vivo porcine lung. Specifically, a delivery sheath was placed into the trachea of the pig lung and an expandable balloon isolating component was deployed to fluidly isolate the lung from atmospheric pressure. The controller settings were a minimum pressure of −50 cm H20, maximum pressure of 20 cm H20 and frequency of 0.5 Hz. The controller was initiated and negative pressure to −50 cm H20 was administered. Once −50 cm H20 was reached, x-ray imaging was initiated with subtraction processing and the controller began the positive pressure component of the cycle, reaching 20 cm H20 and expanding the airways. The entire routine lasted 2 seconds (0.5 cycles/second). The resulting image 260 illustrates the effect of generating a lower tissue density within the airways relative to the background lung tissue where the airways may be seen as white branching structures (enhanced with existing x-ray subtraction processing).

Figure 29:
FIG. 29 shows an illustration of an x-ray image from an ex vivo porcine lung where the density of the airway of interest was increased with 0.9% concentration saline fluid.

FIG. 29 shows an experimental result from an ex vivo porcine lung in which the tissue density of the airway walls was increased relative to the background after the injection of normal (0.9%) saline fluid to a pressure of 15 cm H20. The resulting image 270 shows the airways having saline infused within (enhanced with subtraction processing).

Figure 30:
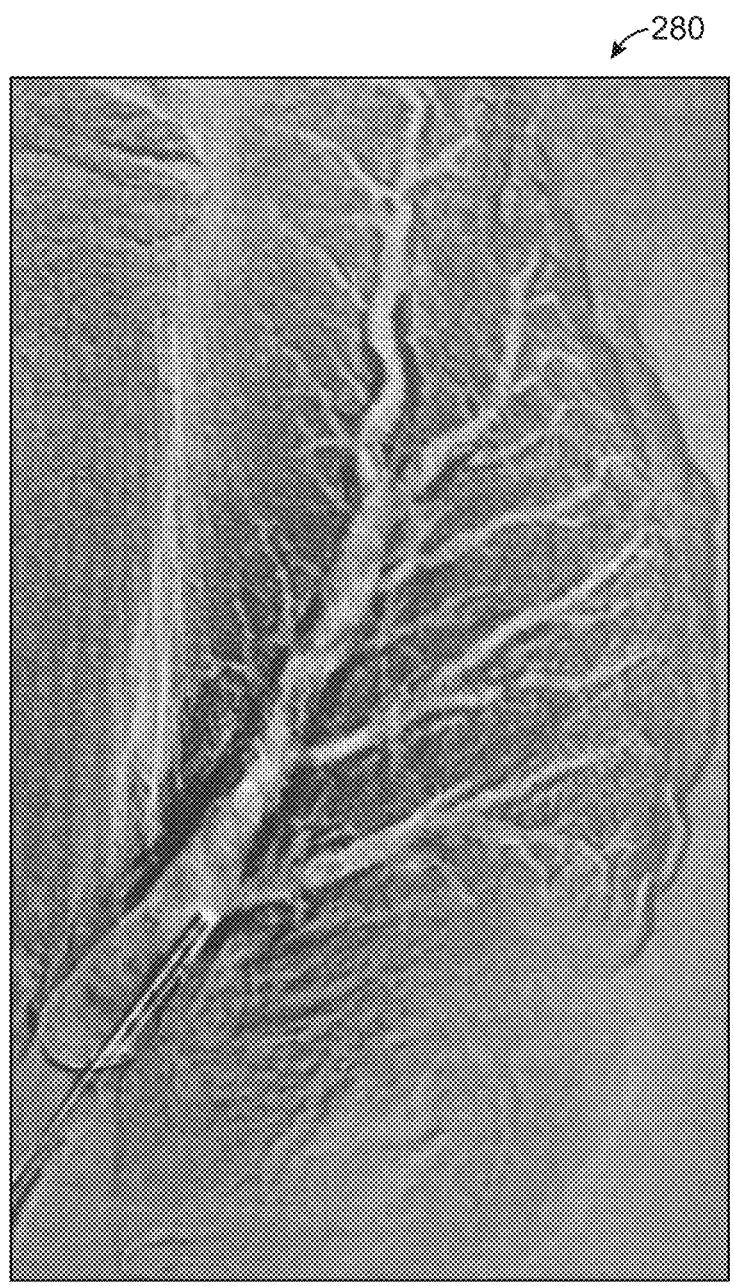
FIG. 30 shows an illustration of an x-ray image from an ex vivo porcine lung where the density of the airway of interest was increased and the image inverted and then superimposed onto a live x-ray image as a roadmap.

FIG. 30 shows an image 280 of the experimental results from an ex vivo porcine lung in which the image 280 was generated using the method described with respect to FIGS. 25A, 26A to C and 27A to C. The image 280 was obtained via x-ray and then inverted, made semi-transparent, and overlaid onto a live x-ray so as to act as a roadmap for the delivery sheath. A delivery sheath was then navigated into various airways using the roadmap generated from the controller routine.

Figure 31A:
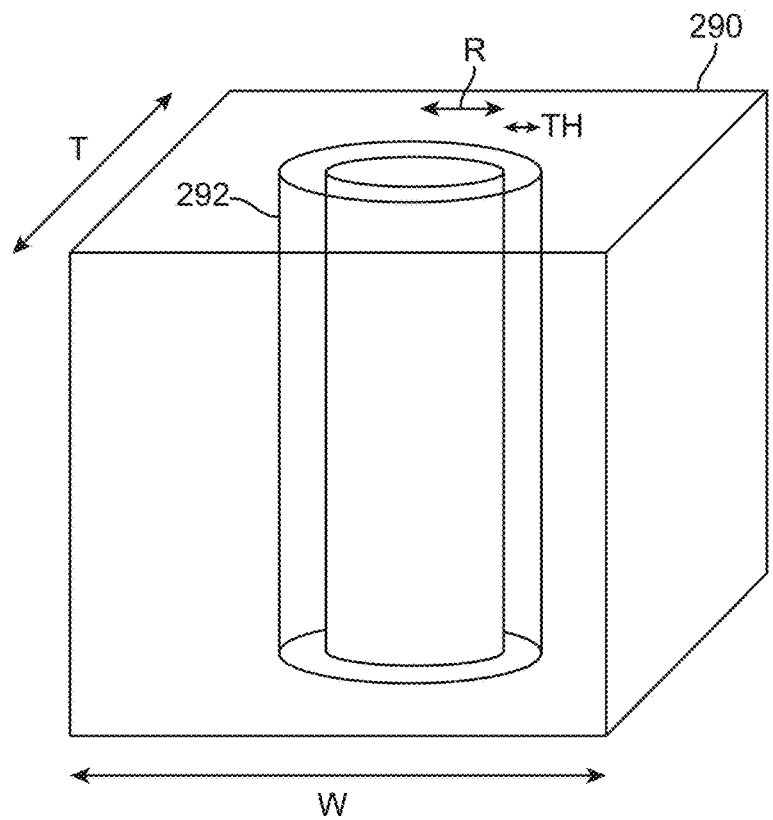
FIGS. 31A and 31B show schematic illustrations representing the changing airway structure when open and collapsed.
Figure 31B:
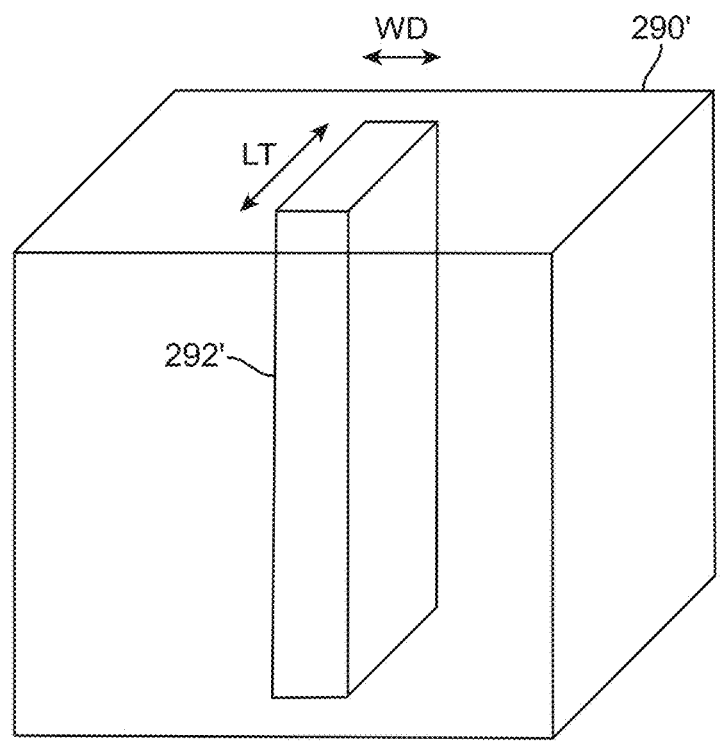

As the airway walls undergo localized movement from the suction or infusion of a gas or liquid, an example of the airway collapse and/or expansion is shown in the representative schematic illustrations of FIGS. 31A and 31B. FIG. 31A represents a typical cross-section 290 of an airway. In this representation, the thickness T, width W, and length represents a 20 mm cross-section where the airway 292 has a radius R of 2.5 mm and a wall thickness TH of 1.7 mm. As air is suctioned from the airways, in this example, the walls of the airway may collapse upon itself 292', as shown in the cross-section 290' of FIG. 31B, forming a collapsed tissue section having a length LT of 9.8 mm and a width WD of 3.4 mm. It is this variation or movement between the initial airway wall position and the collapsed (or expanded) airway wall position that the x-ray system is able to image when subtraction processing is applied.

Figure 32A:
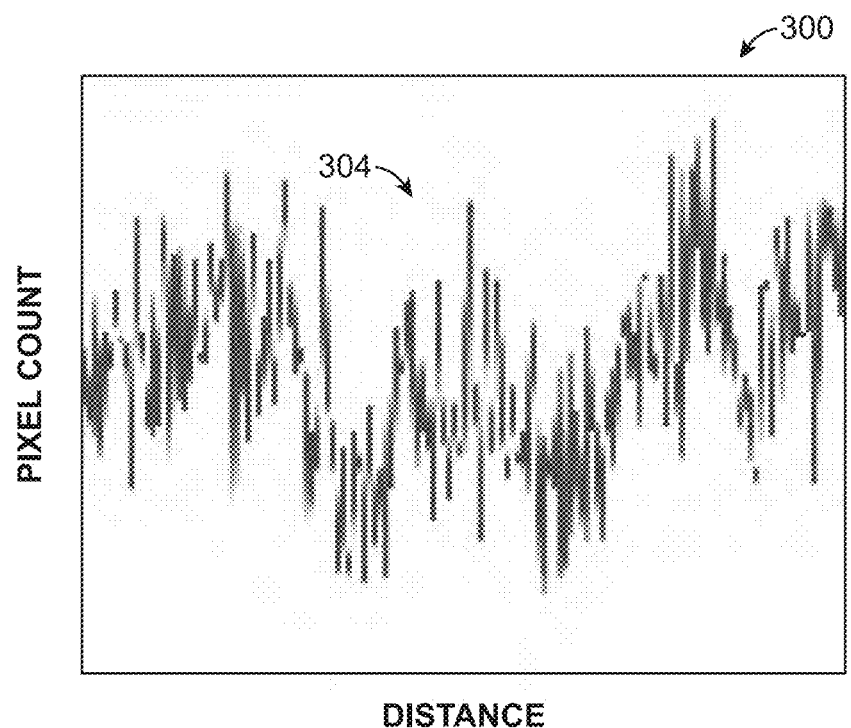
FIGS. 32A and 32B show examples of a line integral of the attenuation of x-rays as they pass through each respective simulation of FIGS. 31A and 31B.
Figure 32B:
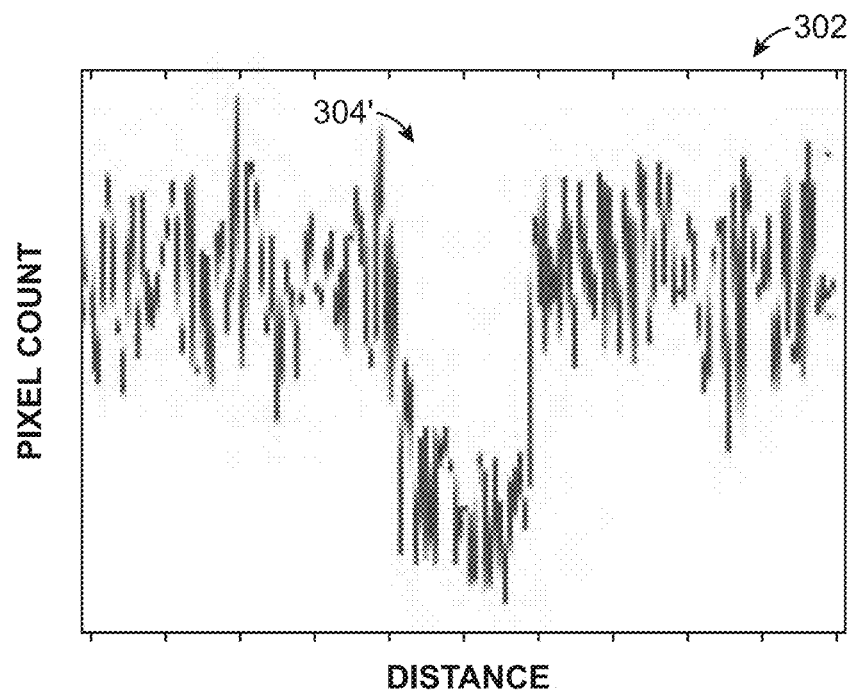

As the x-rays pass through the airway walls, FIGS. 32A and 32B show examples of a line integral of the attenuation of x-rays as they pass through each respective simulation of FIGS. 31A and 31B, respectively, in an axial (or x) plane. As shown in FIG. 32A, the pixel count (Y-axis) drops when the tissue density is relatively higher than the surrounding tissue as x-rays are absorbed. FIG. 32A shows in chart 300 that there is a small decrease in the pixel count as the x-rays pass through the center 304 of the airway while FIG. 32B in chart 302 shows a relatively larger, more uniform drop in pixel count when the airway is closed or collapsed 304'.

METHODS

The various methods illustrated in the flowcharts may be implemented with any of the various embodiments of the controller and components described herein. Alternative steps in any of the methods are intended to be within the scope of the description.

For example, the maximum pressure and minimum pressure, waveform shape (e.g. square or sine waves) and frequency of cycling between maximum and minimum pressures can be prescribed, as illustrated in the graphs of FIGS. 45A to 45C. For example, a maximum pressure can be set to, e.g., 30 cm H20, and a minimum pressure set to, e.g., −10 cm H20 with frequency at, e.g., 5 Hz. In this variation, the controller would trigger the pump system to reach a positive pressure of 30 cm H20 in the airways (using positive pressure), and once 30 cm H20 is reached, the positive pressure pump would terminate and the negative pressure suction would be triggered to bring the pressure down to −10 cm H20. The cycle from 30 cm H20 to 0 cm H20 could occur at a frequency of 5 times per second. As illustrated in the graph of FIG. 45A, the negative pressure 800 may be activated once the maximum pressure of 30 cmH2O has been reached to decrease the pressure to the minimum pressure 802 of −10 cm H2O has been reached. The positive pressure may then be activated 804 to increase the pressure back up to 30 cmH2O. A single cycle may occur within a period PD of ⅕ sec such that five cycles (5 Hz) of the pressure cycling may occur within one second.

Alternatively, the maximum pressure could be set at, e.g., 30 cm H20 and the minimum pressure set to, e.g., 0 cm H20 (i.e. atmospheric pressure) with frequency of, e.g., 3 Hz. In this example, as shown in the graph of FIG. 45B, the positive pressure pump would activate until airway pressures reached 30 cm H20, and once reached the positive pressure pump would terminate and the negative pressure pump would activate to bring the pressure down to 0 cm H20. The cycle from maximum pressure to minimum pressure could occur 3 times per second while imaging.

Alternatively, the maximum pressure could be set to, e.g., 0 cm H20 and the minimum pressure to, e.g., −30 cm H20 and the frequency to 5 Hz, as shown in the graph of FIG. 45C. In this example, depending on the baseline pressure in the airway which would be measured by the pressor sensor, either the negative or positive pump would activate to bring the pressure to 0 cm H20, and then would terminate and the negative pressure pump would be activated to bring the pressure down to −30 cm H20. The negative pressure pump would stop, and the positive pressure pump would activate to raise the pressure back to 0 cm H20. This full cycle from 0 cm H20 to −30 cm H20 back to 0 cm H20 could occur 5 times per second.

Alternatively, both maximum and minimum pressures could both be above or below 0 cm H20 (i.e. atmospheric) and the controller would function in a similar manner as above, oscillating between the maximum and minimum pressures using the alternating positive and negative pressure pumps. The frequency could be set in a range from 0.5-50 Hz.

Alternatively, the maximum and minimum pressure values may be set equal to one another and the frequency could be 0 Hz. In this case, the pumps would coordinate together to maintain a specific airway pressure (e.g. 15 cm H20). This could be used to inflate an area of lung and maintain this level of pressure during x-ray imaging. Of note, activation of x-ray imaging can occur during any phase of the prescribed pressure routines described above but can be optimized by linking the controller and the x-ray system such that imaging is initiated during either a maximum or minimum pressure value.

Figure 33:
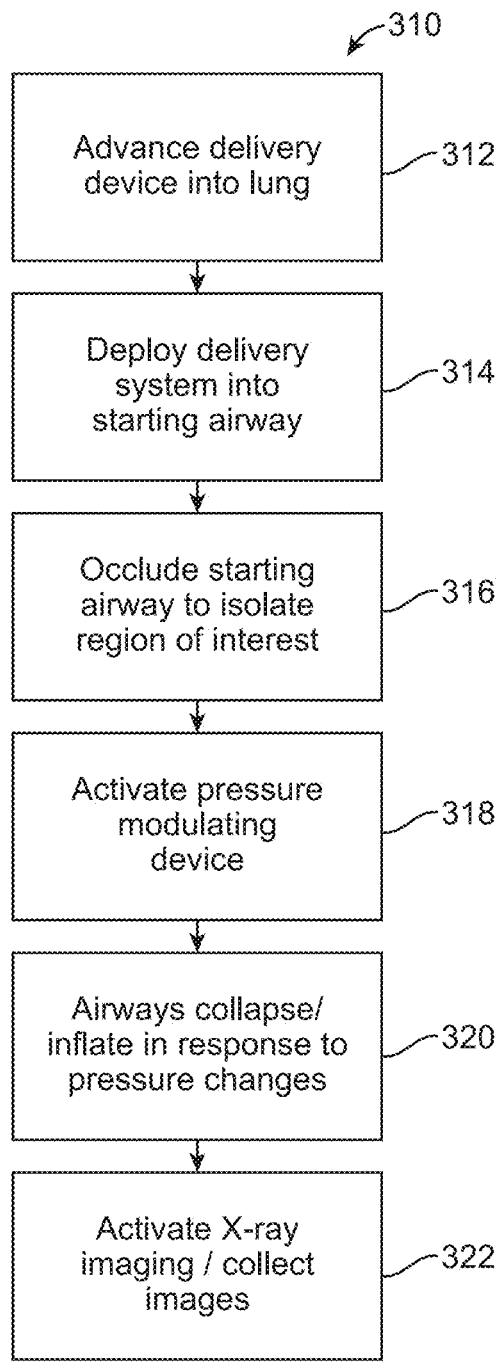
FIGS. 33 to 37 show examples of different methods for altering the airway density and imaging.

Turning now to some examples of the methods, FIG. 33 shows a flowchart 310 which may be used with any of the systems and components herein. An initial step 312 may include advancing the delivery device or sheath 12 into the airways of at least one of the lungs and into proximity of a tissue region of interest. The delivery system may be deployed into the starting airway 314 and a portion of the airway may be occluded to isolate the tissue region of interest 316. The pressure modulation of the system may be activated 318, e.g., to collapse and/or inflate the airways of interest 320. If the airways of interest are to be collapsed, a suction pressure may be applied to collapse the airway walls from their initial position and then released allowing for the airway walls to expand naturally from their collapsed position back to their initial, natural position. As the airway walls are manipulated, the remainder of the lung may remain relatively unaltered and unmoved by the airway wall movement. Also, as the airway walls are moved, the x-ray imaging may be activated to collect the images as the tissue walls are moved 322. The microcontroller may be configured to trigger and/or gate the activation of the x-ray imager, e.g., by the initiation of the airway wall pressure changes.

The pressure changes may be constrained by the imaging system used with the system. For example, if the x-ray imager is running at 30 frames per second, then the pressure changes imparted within the airways may be constrained to be less than 30 Hz and possibly less than half the imaging rate of the x-ray imager according to the Nyquist rate or frequency where the minimum rate at which a signal is sampled without introducing errors is twice the highest frequency present in the signal. The imparted rate of pressure change frequency in the tissue should ideally be less than the frame rate of the x-ray imager and ideally less than half in order for the airway wall displacements to be sufficiently detected by the x-ray detector. In other words, the greater the ratio of the x-ray frame rate relative to the air pressure oscillation frequency, the smoother the image detection of the airway displacements.

Figure 34:
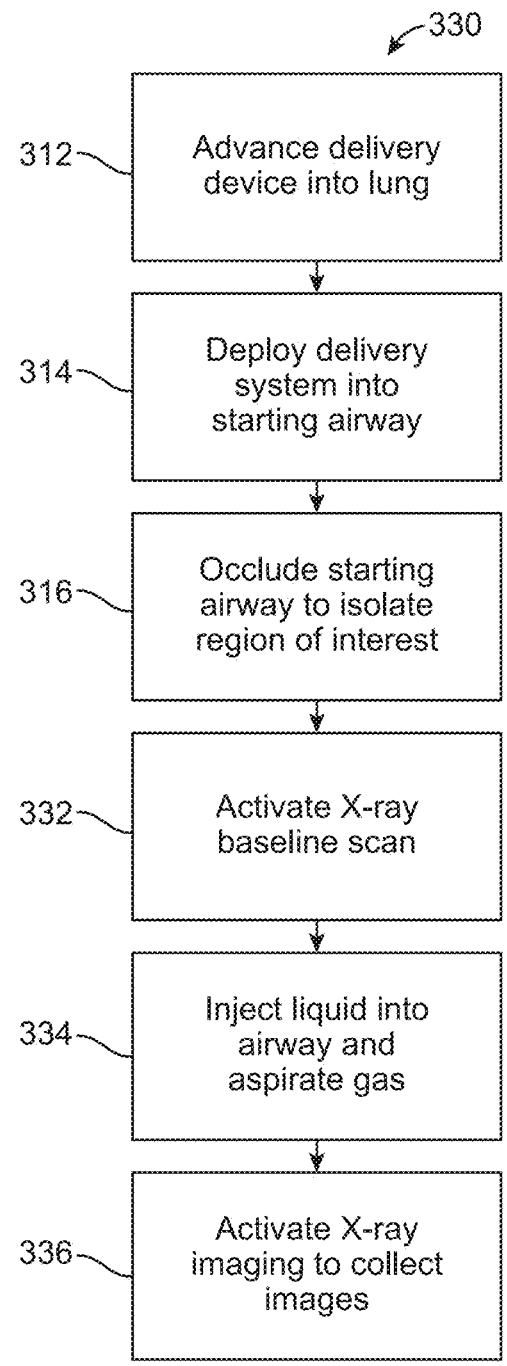

FIG. 34 shows a flowchart 330 of another method where after the airway of interest is occluded 316, an initial x-ray image may be taken to obtain a baseline scan 332. A liquid, such as saline, may be injected into the airways of interest and gas may be aspirated 334 to induce the localized displacement of the airway walls. The x-ray images may accordingly be collected 336, as described above.

Figure 35:
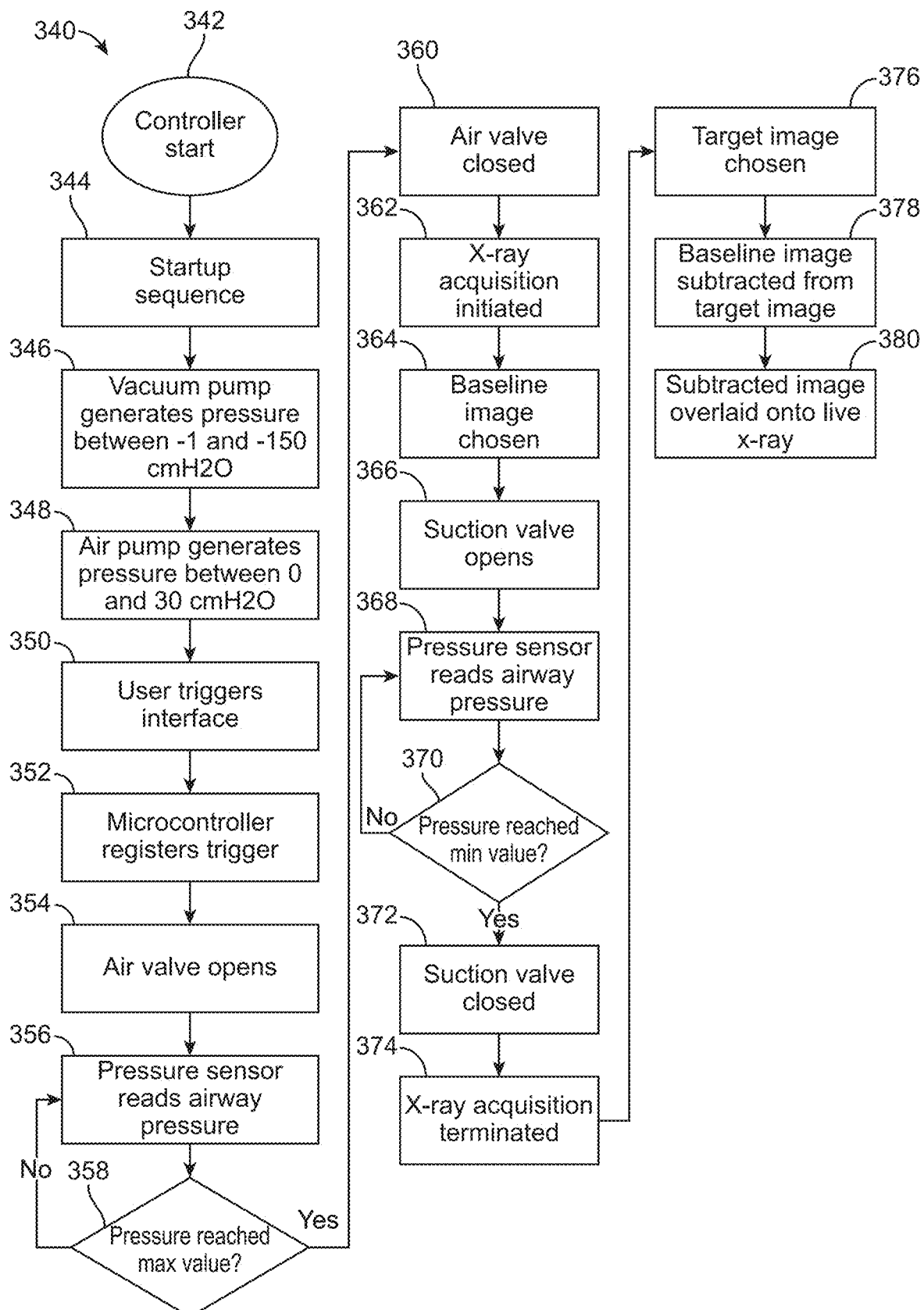

FIG. 35 shows a flowchart 340 of yet another method where the once the controller has been activated 342 and a startup sequence 344 has completed, a vacuum pump may be activated to generate a negative pressure in the airway of interest of anywhere between −1 and −150 cmH2O 346 and an air pump may also be activated to generate a positive pressure of anywhere between 0 and 50 cmH2O 348. The user may trigger an interface 350 on the controller such that the microcontroller registers the trigger 352 and opens the air valve 354 such that the airways of interest are infused with positive pressure air.

The pressure sensor may detect the airway pressure 356 and the microcontroller may monitor the airway pressure until a predetermined maximum pressure value has been reached 358 upon which the air valve may be closed 360. X-ray acquisition may then be initiated 362 by the microcontroller and an initial baseline image may be acquired 364. Then, the suction valve may be opened 366 by the microcontroller to remove the infused air from the airways while the pressure sensor may detect the airway pressure 368 until a predetermined minimum pressure value has been reached 370. Afterwards the suction valve may be closed 372 and x-ray acquisition may be terminated 374. Termination of the suction pressure may occur after a period of, e.g., between 0.1 and 240 seconds. A target image may be selected 376 by the microcontroller and the initial baseline image (from step 364) may be subtracted from the selected target image (from step 376) 378 and the resulting subtracted image may be optionally overlaid onto a real-time or live x-ray image 380. The introduction of the positive pressure from step 354 to the suction valve being closed in step 372 may be optionally repeated multiple times to obtain the subtracted image in step 378 and overlay onto the x-ray image in step 380.

Figure 36:
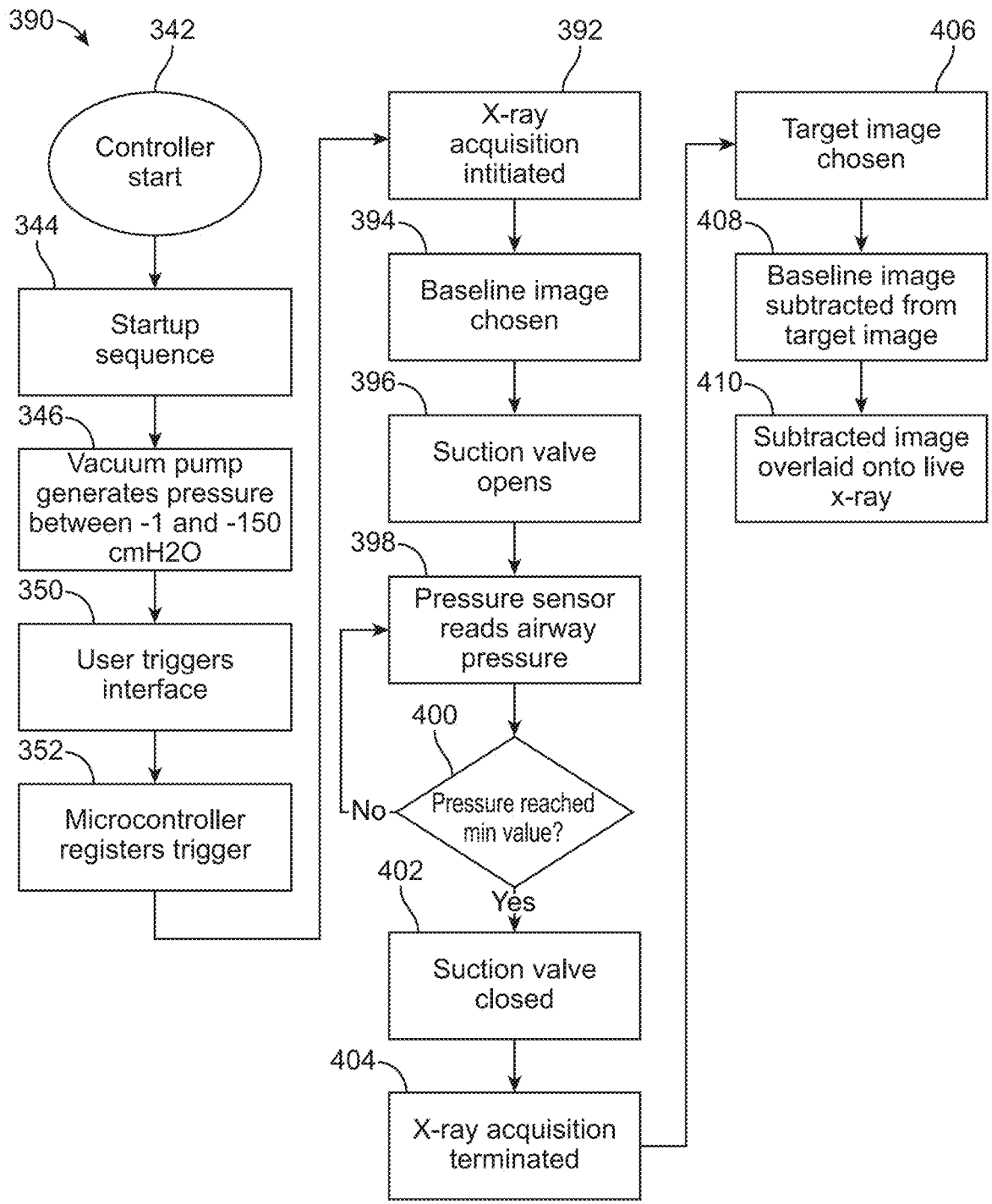

FIG. 36 shows a flowchart 390 of yet another method in which the initial steps are similar to those shown in FIG. 35. However, after the microcontroller registering a trigger 352, the microcontroller may instead initiate x-ray acquisition 392 and a baseline image may be chosen 394 by the microcontroller. The suction valve may then be opened 396 by the microcontroller to remove the infused air from the airways while the pressure sensor may detect the airway pressure 398 until a predetermined minimum pressure value has been reached 400. Afterwards the suction valve may be closed 402 and x-ray acquisition may be terminated 404. Termination of the suction pressure may occur after a period of, e.g., between 0.1 and 240 seconds. A target image may be selected 406 by the microcontroller and the initial baseline image may be subtracted from the selected target image 408 and the resulting subtracted image may be optionally overlaid onto a real-time or live x-ray image 410. As above, the introduction of the positive pressure to the suction valve being closed may be optionally repeated multiple times to obtain the subtracted image and overlay onto the x-ray image.

Figure 37:
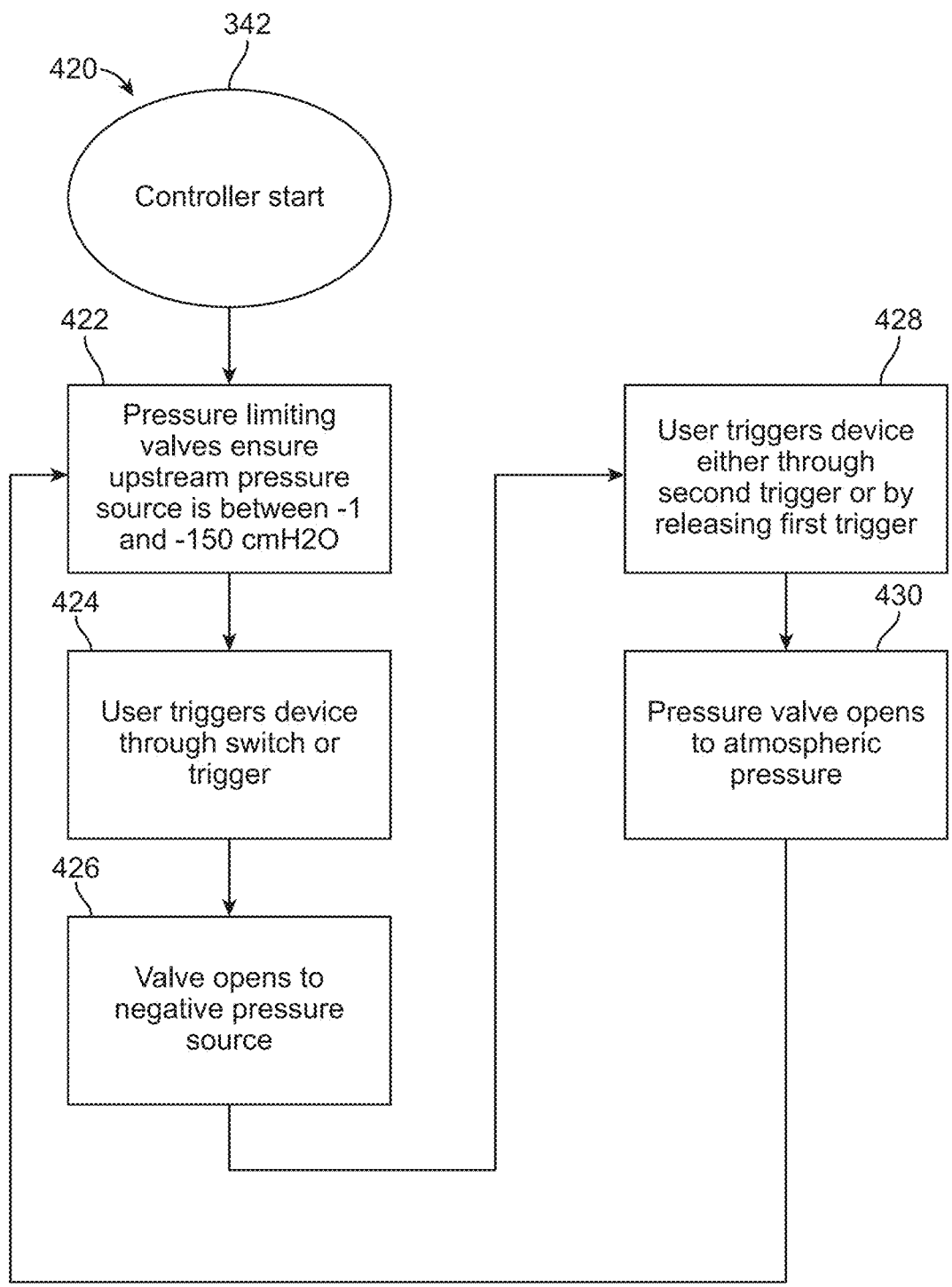

FIG. 37 shows a flowchart 420 of yet another method which may be performed by the controller in which the negative pressure pump may be controlled via pressure limiting valves to ensure that the upstream pressure pump remains between, e.g., −1 and −150 cmH2O 422. The user may trigger the controller, e.g., through a switch or trigger, 424 to cause the valve to open to the negative pressure source 426. The user may then active the controller further by either releasing the trigger or actuating a second trigger 428 to cause a valve within the controller to either stop or limit the suction pressure and open to atmospheric pressure 430.

Figure 38:
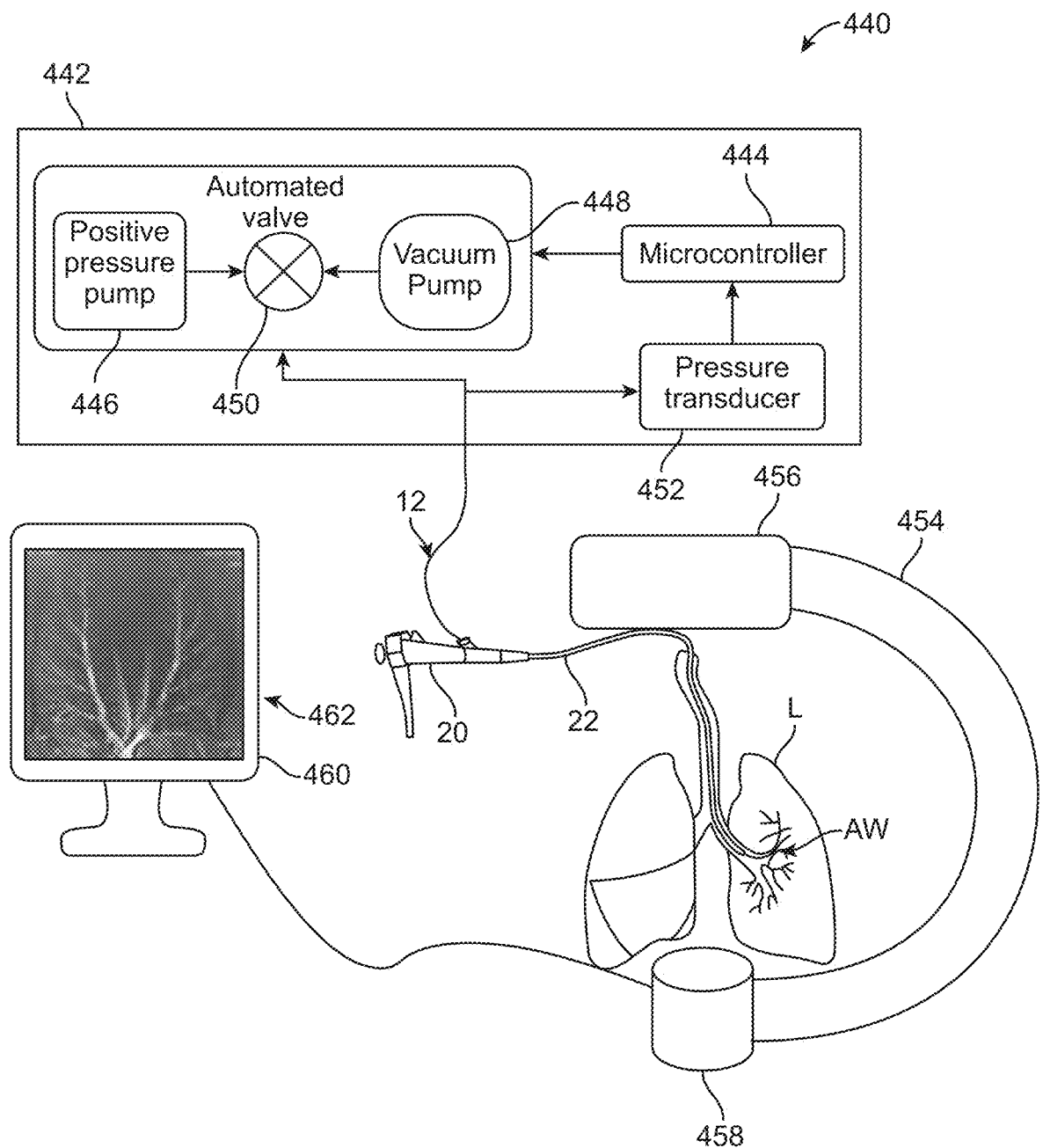
FIG. 38 shows a schematic illustration of one variation of a controller system used with an imaging system for altering airway density and imaging.

Turning now to FIG. 38, a schematic diagram 440 of one variation of the pressure system and the imaging system. The controller 442 is illustrated as having a positive pressure pump 446, vacuum pump 448, and automated valve 450 each in communication with the microcontroller 444 as well as the pressure transducer 452 being in communication with the microcontroller 444; however, any of the controller embodiments described herein may be utilized. The controller 442 may be in communication with the delivery sheath 12 which is advanced into the lung L of the patient through the elongate body 22 of the bronchoscope 20 and into the airways AW of interest. The patient may be positioned into proximity of the x-ray imager prior to the delivery sheath 12 being introduced into the patient's lung L. While any number of imaging assemblies may be used, a X-ray machine 454 fluoroscopy imager is illustrated as an example where the patient may be positioned between the x-ray source 458 and image receptor 456. As the pressure is modulated within the patient for imaging, the resulting x-ray images 462 may be displayed, e.g., upon a monitor 460, and the x-ray imager may be in communication with the controller 442 such that the image acquisition and subtraction processing enhancement may be applied automatically by the imager when triggered or gated by the controller 442.

Figure 39A:
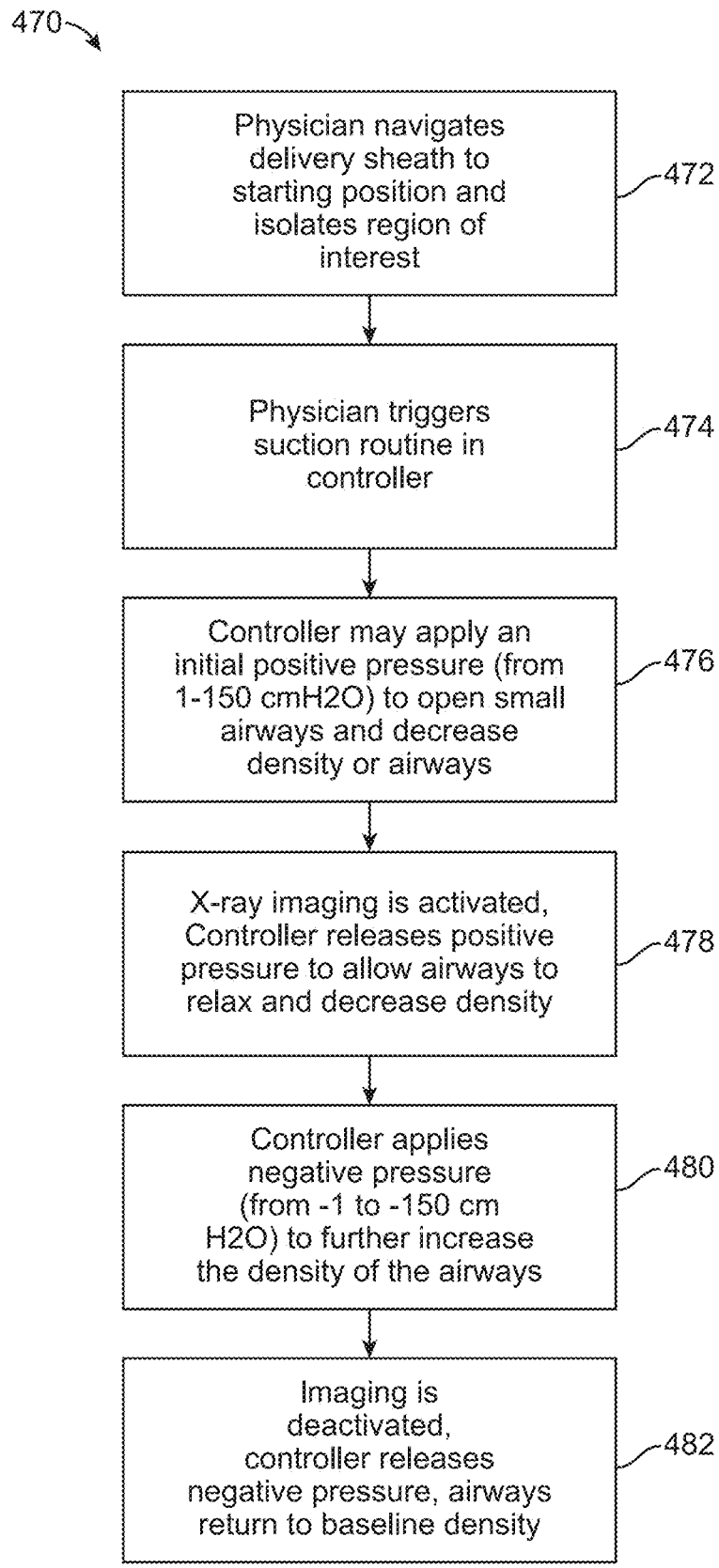
FIGS. 39A and 39B show a flowchart and method for implementing one variation of the method.

Turning now to FIG. 39A, yet another flowchart 470 is illustrated for a method to increase the density of the tissue airway walls by applying a negative pressure. As shown, the user may navigate the delivery sheath 12 to an initial starting position within the lung and isolate the tissue region of interest 472. The user may trigger a suction routing programmed within the microcontroller within the controller 474 such that the controller applies an initial positive pressure anywhere between, e.g., 1 to 50 cmH2O, to initially open the airways of interest and thereby decrease the density of the airway tissues 476. The x-ray imaging may be activated, e.g., automatically by the controller, as the controller actuates the release of the positive pressure to allow the airways to relax and decrease in tissue density 478. The controller may then apply a negative pressure anywhere between, e.g., −1 to −150 cmH2O, to collapse the airways and further increase the tissue density 480. The imaging may then be deactivated and the controller may release the negative pressure allowing for the airways to return to their baseline density 482.

Figure 39B:
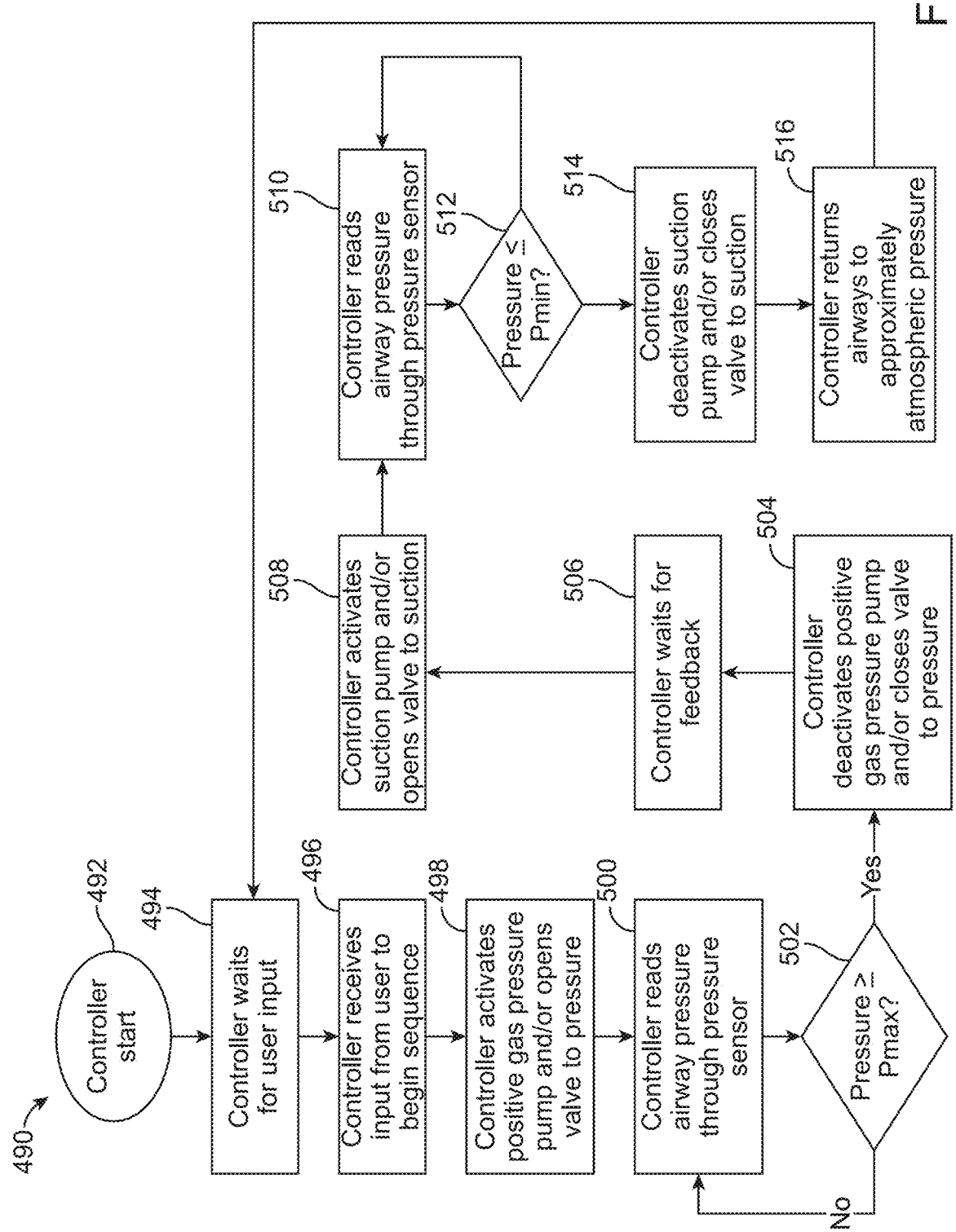

FIG. 39B illustrates a flowchart 490 by which the controller may correspondingly implement the method shown in FIG. 39A. Once the controller has been actuated to start 492, the controller may wait for user input 494, e.g., via control input 94. Once the controller has received an input from the user to begin a sequence 496, the controller may actuate a positive gas pressure pump and/or open a valve to an external pressure source 498. The controller may monitor the airway pressure through the pressure sensor 500 until a threshold maximum pressure has been reached 502. Once the maximum pressure is reached, the controller may deactivate the positive gas pressure pump and/or close the valve to the pressure source 504 and the controller may then optionally wait for feedback 506. The controller may then activate a suction pump and/or open a valve to an external suction source 508 while the controller monitors the airway pressure through the pressure sensor 510 until a threshold minimum pressure has been reached 512. The controller may then deactivate the suction pump and/or close the valve to the suction source 514 and the controller may then allow for the airways to return to atmospheric pressure 516. The process may be repeated as necessary or desired to obtain the images of the tissue density changes.

Figure 40A:
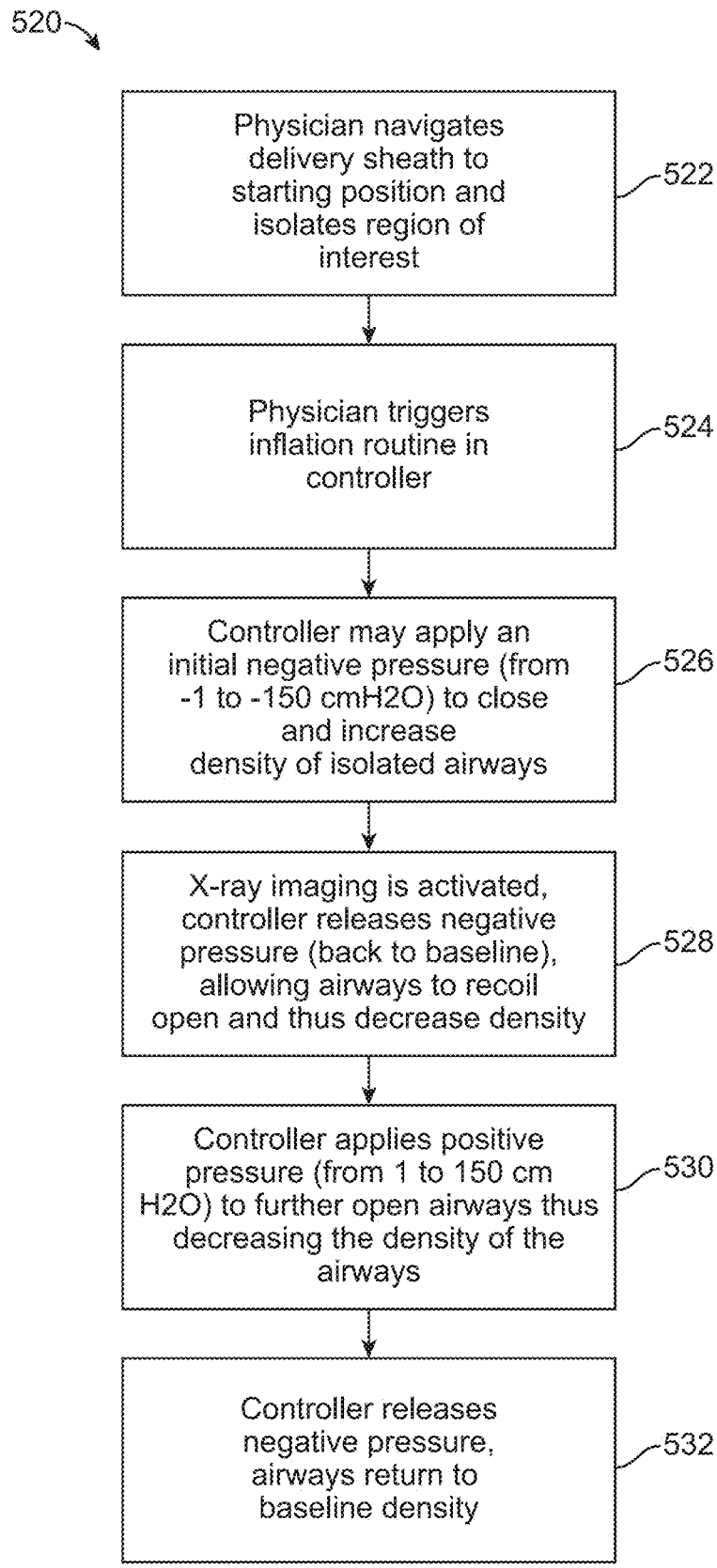
FIGS. 40A and 40B show a flowchart and method for implementing another variation of the method.

FIG. 40A shows yet another variation of a flowchart 520 illustrating another example where after the user has navigated the delivery sheath 12 into proximity to the airways of interest 522, the user may trigger an inflation routine in the controller 524 such that the controller applies an initial negative pressure of anywhere from, e.g., −1 to −150 cmH2O, to close and increase a density of the isolated airway tissue walls 526. The controller may actuate x-ray imaging and release the negative pressure back to the baseline pressure such that the airways may naturally recoil back to their open state and thus decrease the tissue density of the airway walls 528. The controller may then apply a positive pressure of anywhere from, e.g., 1 to 50 cmH2O, to further open the airways and thus decrease the tissue density of the airway walls 530. This process could be repeated to oscillate the airway walls from open (or partially open) to closed (or partially closed) rapidly at a frequency ideally chosen based on the imaging frame rate (ideally less than half the frame rate). This will have the effect of rapidly altering the density of the airway which can be detected on x-ray imaging. After cycling, the controller may then release the pressure and allow the airway walls to return to their baseline density 532.

Figure 40B:
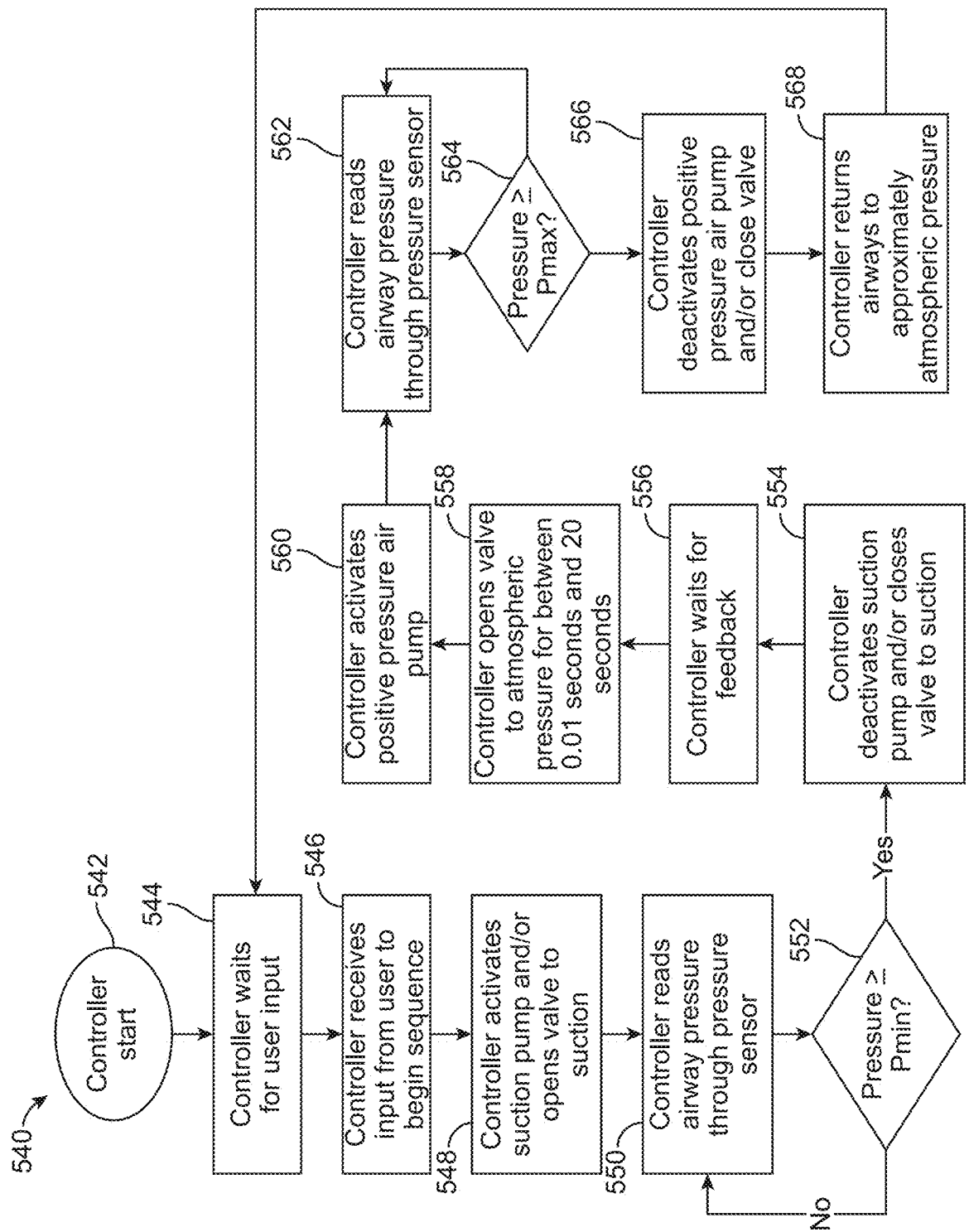

FIG. 40B illustrates a flowchart 540 by which the controller may correspondingly implement the method shown in FIG. 40A. Once the controller has been actuated to start 542, the controller may wait for user input 544, e.g., via control input 94. Once the controller has received an input from the user to begin a sequence 546, the controller may actuate a suction pump and/or open a valve to an external suction source 548. The controller may monitor the airway pressure through the pressure sensor 550 until a threshold minimum pressure has been reached 552. Once the minimum pressure is reached, the controller may deactivate the suction pump and/or close the valve to the suction source 554 and the controller may then optionally wait for feedback 556. The controller may then open a valve to atmospheric pressure for anywhere between, e.g., 0.01 to 20 seconds, 558 while the controller activates the positive pressure air pump 560 while monitoring the airway pressure through the pressure sensor 562 until a threshold maximum pressure has been reached 564. The controller may then deactivate the positive pressure air pump and/or close the valve to the suction source 566 and the controller may then allow for the airways to return to atmospheric pressure 568. The process may be repeated as necessary or desired to obtain the images of the tissue density changes.

Figure 41A:
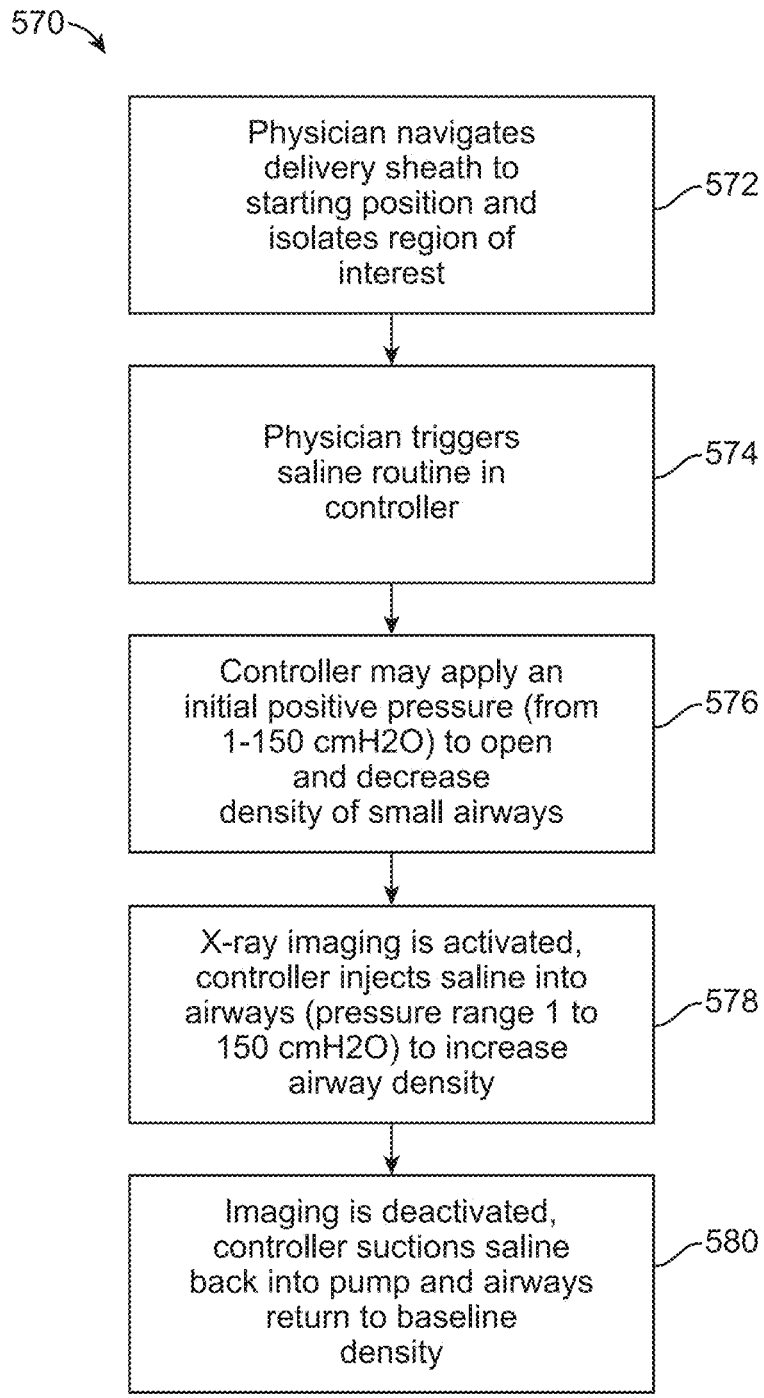
FIGS. 41A and 41B show a flowchart and method for implementing another variation of the method.

FIG. 41A shows yet another variation of a flowchart 570 illustrating another example where after the user has navigated the delivery sheath 12 into proximity to the airways of interest 572, the user may trigger a saline inflation routine in the controller 574 such that the controller applies an initial positive pressure of anywhere from, e.g., 1 to 50 cmH2O, to open and decrease a density of the isolated airway tissue walls 576. The controller may actuate x-ray imaging as the saline is injected into the airways between the pressure range of, e.g., 1 to 50 cmH2O, to increase the airway density 578. The controller may then deactivate the imaging and actuate the suction of saline from the airways to return the airway tissue walls back to their baseline density 580.

Figure 41B:
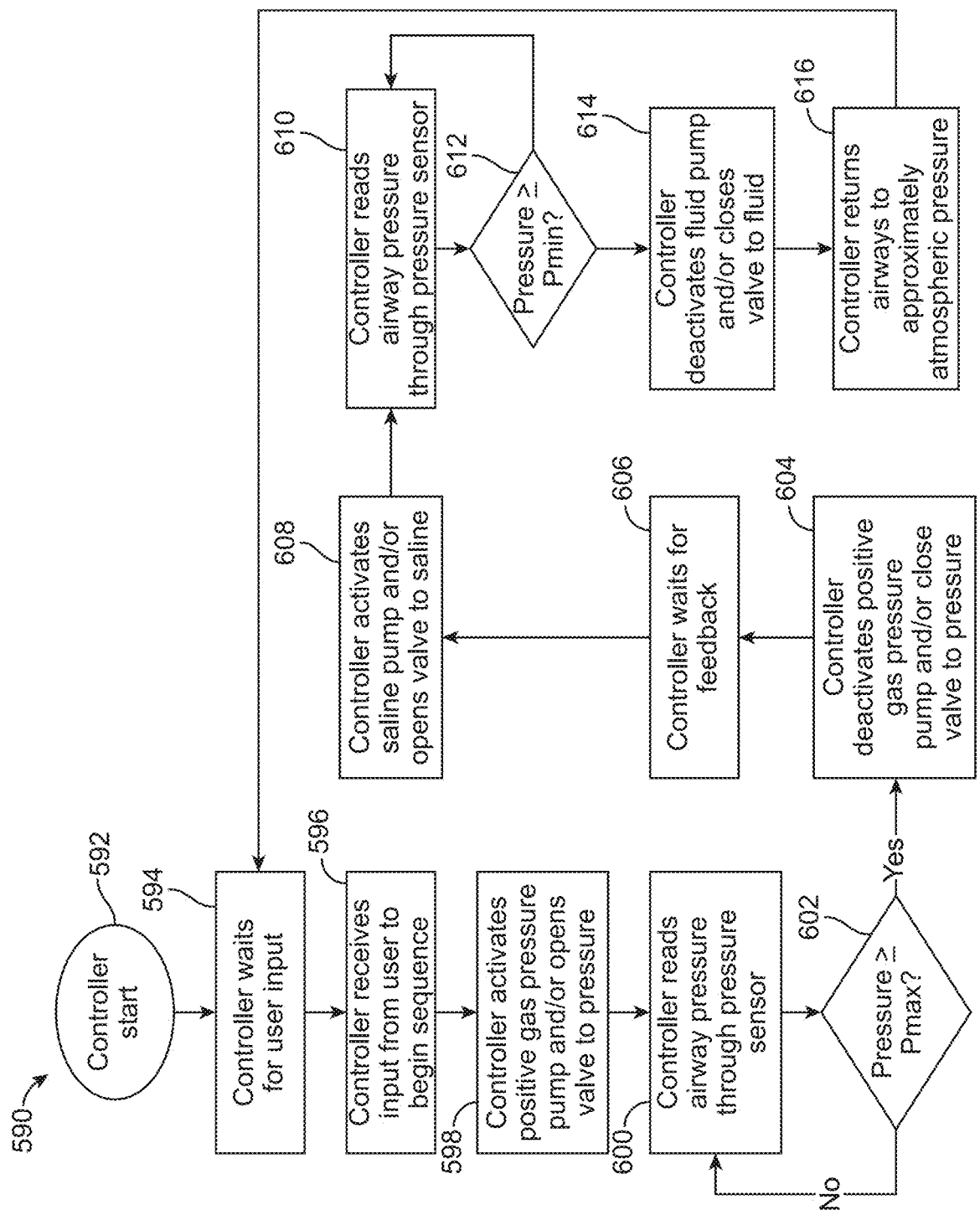

FIG. 41B illustrates a flowchart 590 by which the controller may correspondingly implement the method shown in FIG. 41A. Once the controller has been actuated to start 592, the controller may wait for user input 594, e.g., via control input 94. Once the controller has received an input from the user to begin a sequence 596, the controller may actuate a positive gas pressure pump and/or open a valve to an external pressure source 598. The controller may monitor the airway pressure through the pressure sensor 600 until a threshold maximum pressure has been reached 602. Once the maximum pressure is reached, the controller may deactivate the positive gas pressure pump and/or close the valve to the pressure source 604 and the controller may then optionally wait for feedback 606. The controller may then activate a fluid pump and/or open a valve to an external saline source 608 while the controller monitors the airway pressure through the pressure sensor 610 until a threshold minimum pressure has been reached 612. The controller may then deactivate the fluid pump and/or close the valve to the suction source 614 and the controller may then allow for the airways to return to atmospheric pressure 616. The process may be repeated as necessary or desired to obtain the images of the tissue density changes.

Figure 42A:
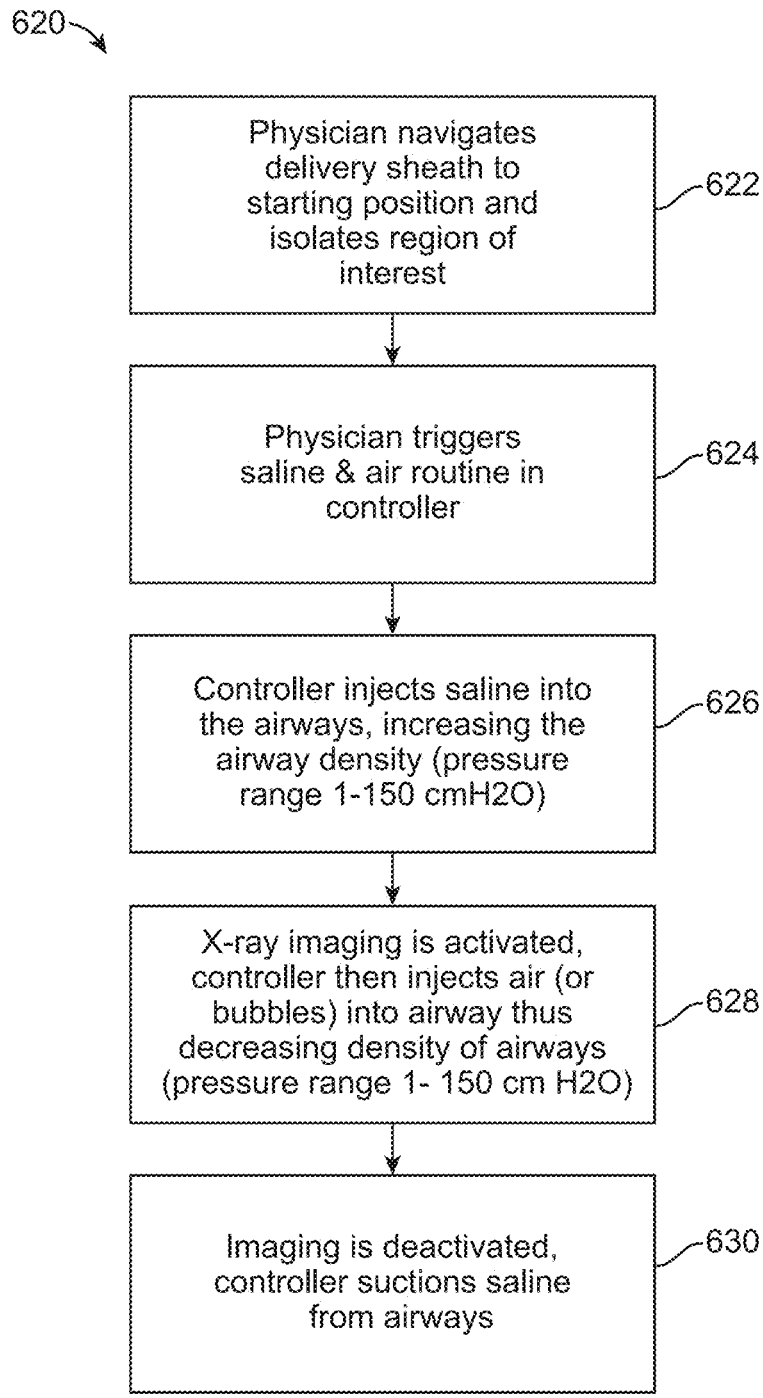
FIGS. 42A and 42B show a flowchart and method for implementing another variation of the method.

FIG. 42A shows yet another variation of a flowchart 620 illustrating another example where after the user has navigated the delivery sheath 12 into proximity to the airways of interest 622, the user may trigger a liquid and gas (e.g., saline and air, respectively) inflation routine in the controller 624 such that the controller injects saline into the airways of interest while increasing the pressure to anywhere between, e.g., 1 to 50 cmH2O, 626. The controller may actuate x-ray imaging and further inject air (which may be released into the saline and through the airways as bubbles) thereby decreasing the tissue density of the airway walls 628. The bubbles may be formed by introducing air into the liquid, for example, via a venturi catheter to aspirate air into the fluid stream during introduction at a rate of, e.g., 0 to 10 cc/second. The imaging may be deactivated and the controller may be actuated to suction the saline from the airways 630.

Figure 42B:
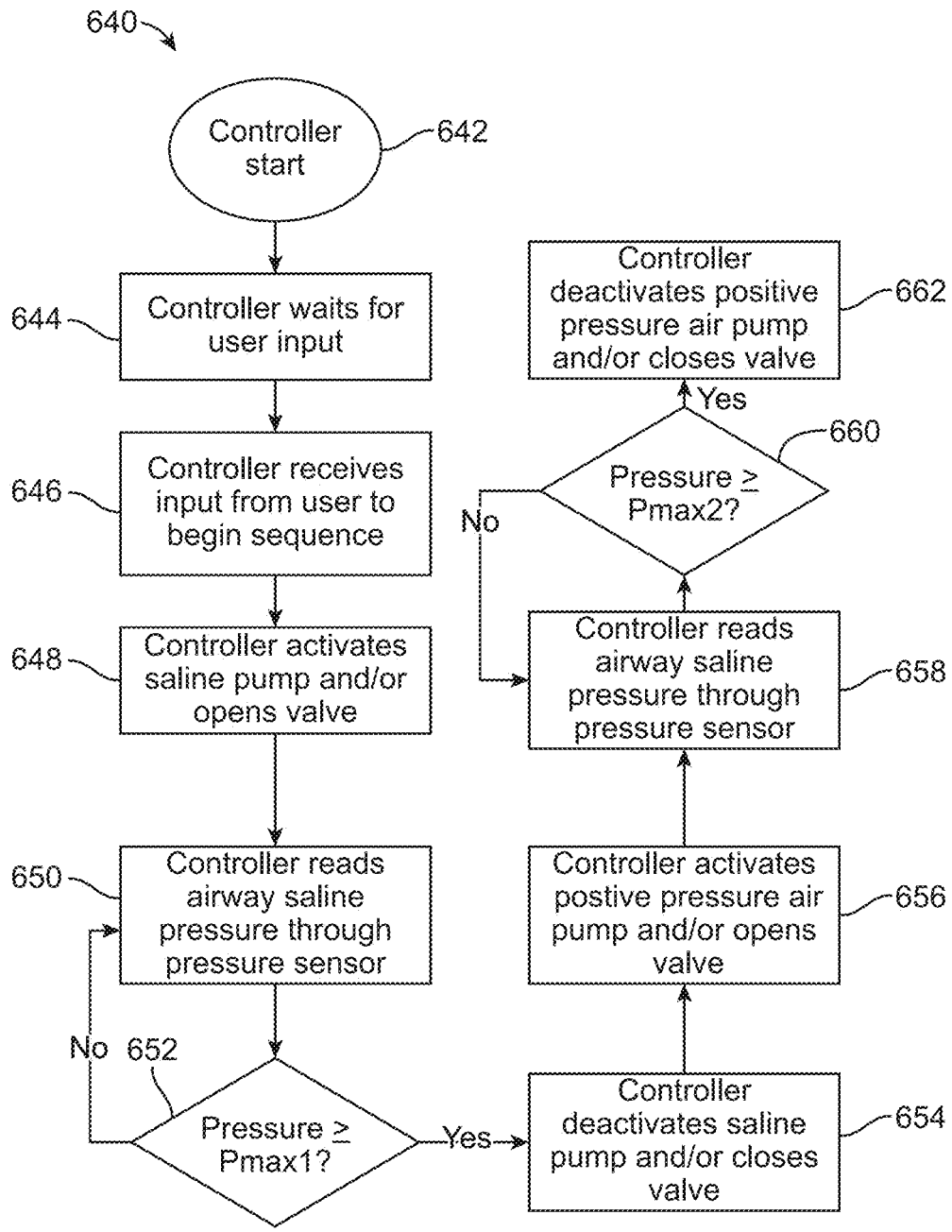

FIG. 42B illustrates a flowchart 640 by which the controller may correspondingly implement the method shown in FIG. 42A. Once the controller has been actuated to start 642, the controller may wait for user input 644, e.g., via control input 94. Once the controller has received an input from the user to begin a sequence 646, the controller may actuate a fluid pump and/or open a valve to an external fluid source 648. The controller may monitor the airway fluid pressure through the pressure sensor 650 until a threshold maximum pressure has been reached 652. Once the maximum pressure is reached, the controller may deactivate the fluid pump and/or close the valve to the fluid source 654. The controller may then activate a positive pressure air pump and/or open a valve to an external pressure source 656 while the controller monitors the airway pressure through the pressure sensor 658 until a threshold maximum pressure has been reached 660. The controller may then deactivate the positive pressure air pump and/or close the valve to the external pressure source 662 and the controller may then allow for the airways to return to atmospheric pressure. The process may be repeated as necessary or desired to obtain the images of the tissue density changes.

Figure 43A:
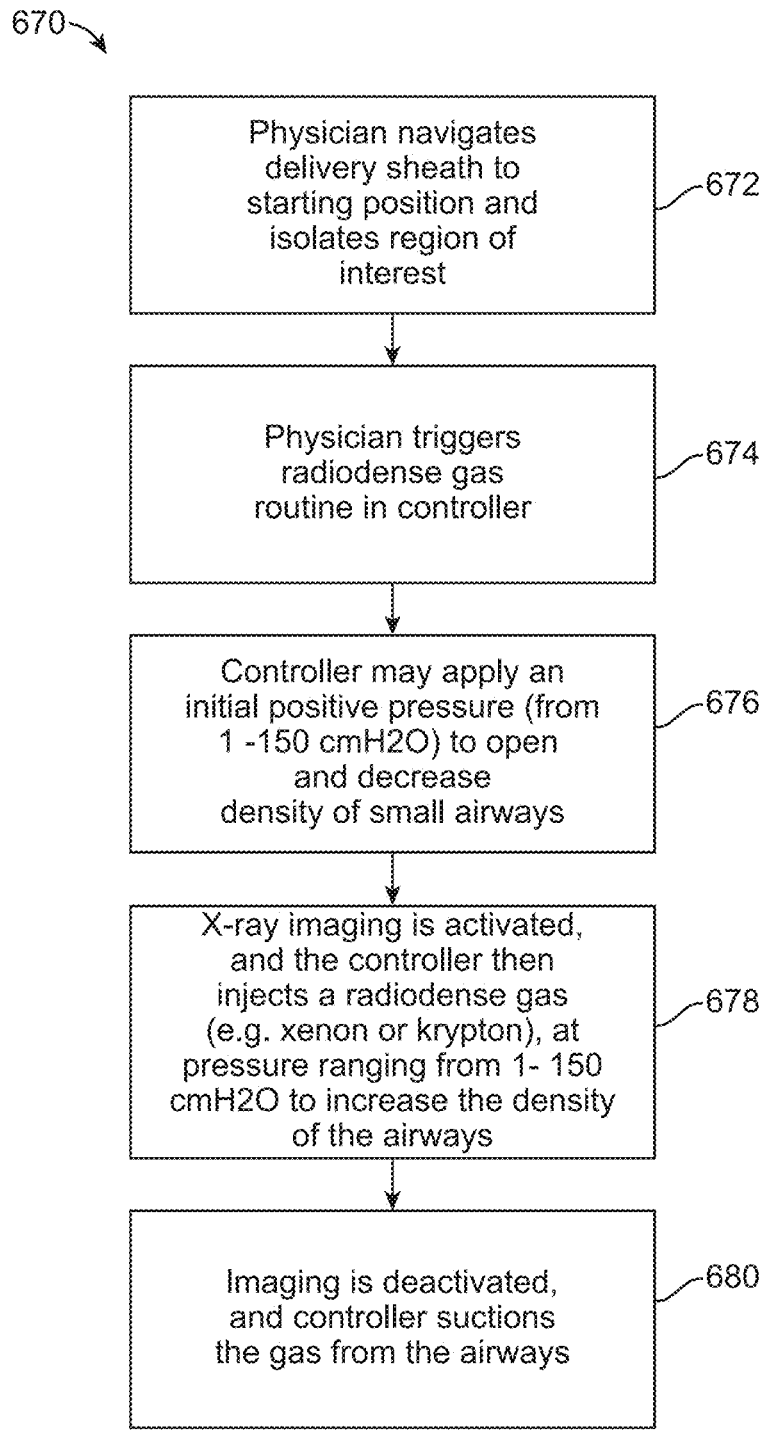
FIGS. 43A and 43B show a flowchart and method for implementing another variation of the method.

FIG. 43A shows yet another variation of a flowchart 670 illustrating another example where after the user has navigated the delivery sheath 12 into proximity to the airways of interest 672, the user may trigger an infusion routine in the controller 674 such that the controller applies an initial positive pressure of anywhere from, e.g., 1 to 50 cmH2O, to open and decrease a density of the isolated airway tissue walls 676. The controller may actuate x-ray imaging and inject a radiodense gas (e.g., Xenon, Krypton, etc.) at a positive pressure of anywhere from, e.g., 1 to 50 cmH2O, to increase the tissue density of the airway walls 678 after which the controller may deactivate the imaging and suction the radiodense gas from the airways 680.

Figure 43B:
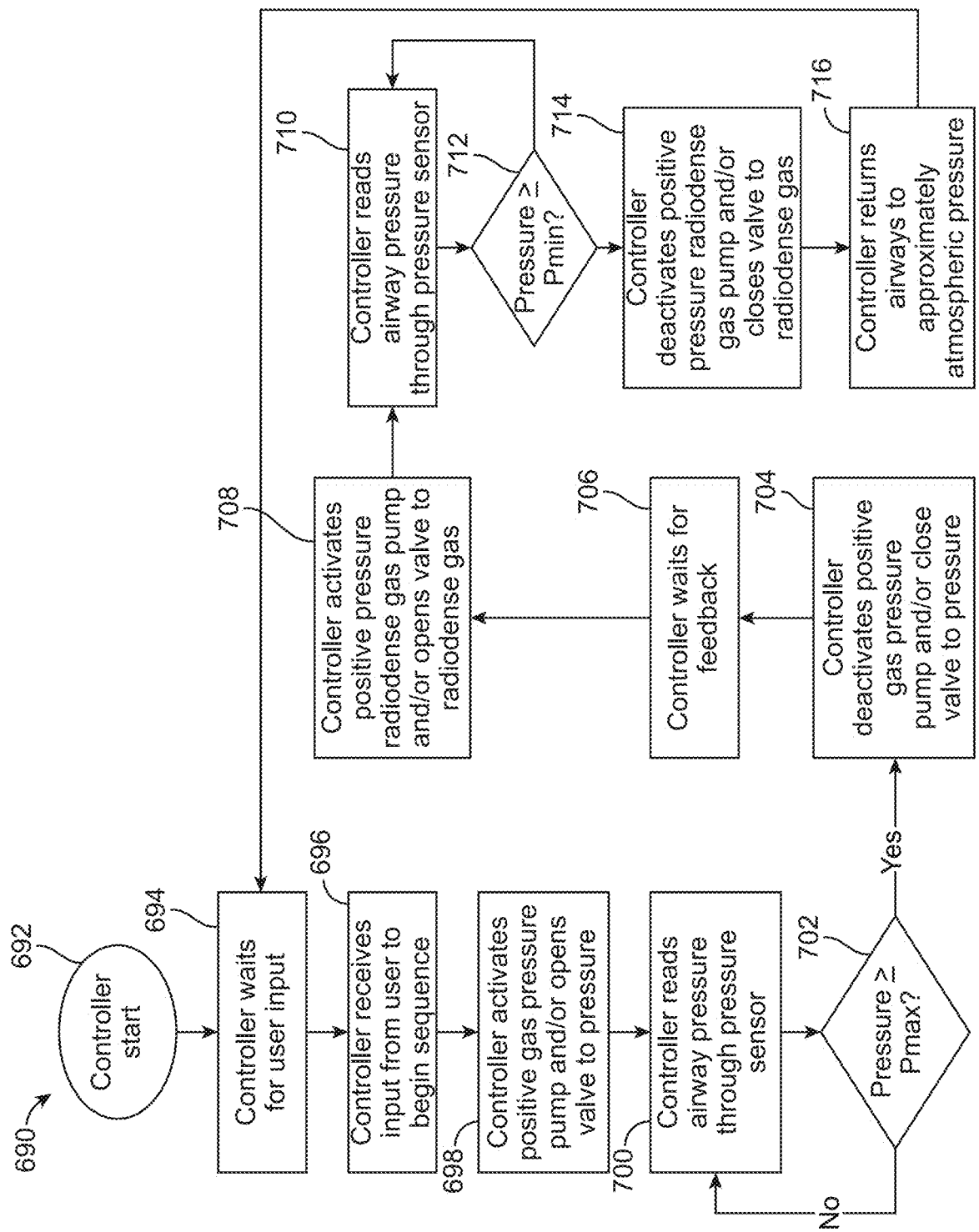

FIG. 43B illustrates a flowchart 690 by which the controller may correspondingly implement the method shown in FIG. 43A. Once the controller has been actuated to start 692, the controller may wait for user input 694, e.g., via control input 94. Once the controller has received an input from the user to begin a sequence 696, the controller may actuate a positive gas pressure pump and/or open a valve to an external pressure source 698. The controller may monitor the airway pressure through the pressure sensor 700 until a threshold maximum pressure has been reached 702. Once the maximum pressure is reached, the controller may deactivate the positive gas pressure pump and/or close the valve to the pressure source 704 and the controller may then optionally wait for feedback 706. The controller may then activate a positive pressure pump to a source of radiodense gas and/or open a valve to an external source of radiodense gase 708 while the controller monitors the airway pressure through the pressure sensor 710 until a threshold minimum pressure has been reached 712. The controller may then deactivate the positive pressure pump and/or close the valve to the radiodense gas source 714 and the controller may then allow for the airways to return to atmospheric pressure 716. The process may be repeated as necessary or desired to obtain the images of the tissue density changes.

Figure 44:
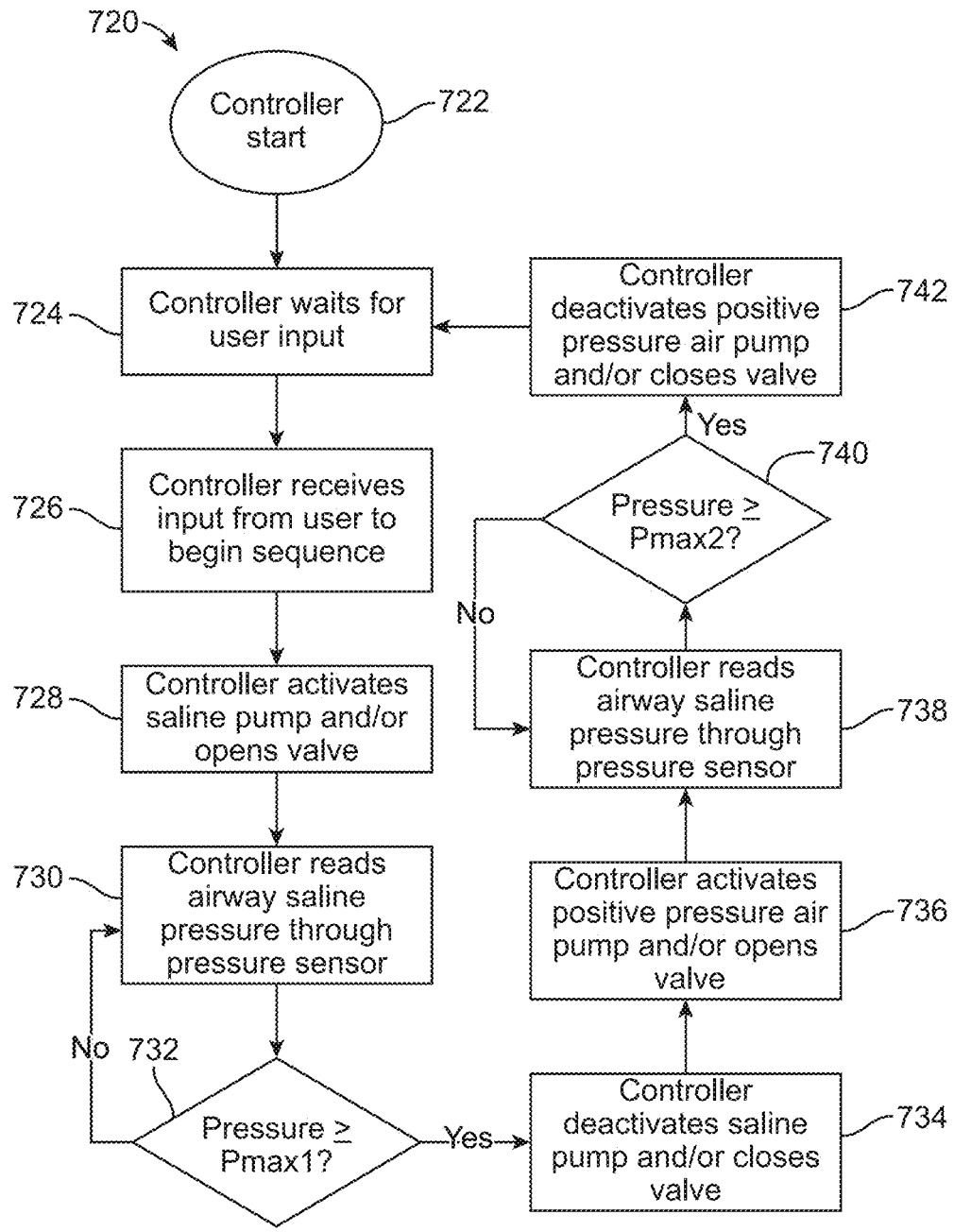
FIG. 44 shows a flowchart for implementing another variation of the method.

FIG. 44 shows yet another variation of a flowchart 720 where once the controller has been actuated to start 722, the controller may wait for user input 724, e.g., via control input 94. Once the controller has received an input from the user to begin a sequence 726, the controller may actuate a fluid pump and/or open a valve to an external fluid source 728. The controller may monitor the airway pressure through the pressure sensor 730 until a threshold maximum pressure has been reached 732. Once the maximum pressure is reached, the controller may deactivate the fluid pump and/or close the valve to the external fluid source 734 and the controller may then activate a positive pressure pump and/or open a valve to an external positive pressure source 736 while the controller monitors the airway pressure through the pressure sensor 738 until a threshold minimum pressure has been reached 740. The controller may then deactivate the positive pressure pump and/or close the valve to the external pressure source 742 and the controller may then allow for the airways to return to atmospheric pressure. The process may be repeated as necessary or desired to obtain the images of the tissue density changes.

With any of the various methods described herein, oscillation of the airways for imaging may be performed with a uniform pressure differential to create the movement and resulting density changes. However, any of the methods described may be altered to create the airway oscillations at an increasing or dampening rate. For instance, the pressures used for negative pressure and positive pressure can be applied with an increasing (or deceasing in the case of negative pressure) subsequent pressure levels. In one example, the pressure applied may begin at a positive pressure of, e.g., 5 cmH2O, followed by a subsequent negative pressure of, e.g., −5 cmH2O, then a subsequent positive pressure of, e.g., 10 cmH2O, then a subsequent negative pressure of, e.g., −10 cmH2O, etc. This could make more airways available for imaging with each successive change in pressure oscillation during an imaging session.

Other variations may include different increments between each of the subsequent pressure levels applied, or the pressure levels may be subsequently decreased beginning from a relatively higher level. Yet other variations may have subsequent pressures being applied at non-uniform increments. Other variations not described are intended to be included within this disclosure.

The disclosed invention herein is not limited to the embodiments and methods described, but may include any number of other applications and uses as well as applications in other regions of the body such as the vascular, urological, GI, and biliary systems. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An airway visualization system, comprising:
a delivery sheath having a length and defining at least one lumen therethrough, wherein the length is positionable within an airway of a subject; and
a controller in communication with the delivery sheath, wherein the controller is configured to manipulate a fluid flow through the at least one lumen whereby a pressure change within the airway of the subject is imparted sufficiently to at least partially manipulate a diameter of the airway to reconfigure between an open resting configuration and a collapsed configuration such that a change in density a position of the airway is imparted at a rate detectable by an imager.

2. The airway visualization system of claim 1 further comprising an isolation component positioned near or at a distal end of the delivery sheath and expandable to at least partially obstruct the airway.

3. The airway visualization system of claim 1 wherein the controller comprises a microcontroller in communication with the delivery sheath.

4. The airway visualization system of claim 3 further comprising a pressure sensor configured to monitor a pressure within the airway and in communication with the microcontroller.

5. The airway visualization system of claim 3 wherein the controller further comprises a fluid pump or suction pump in communication with the microcontroller.

6. The airway visualization system of claim 3 wherein the controller further comprises one or more valves in communication with the microcontroller and also in fluid communication with an external source of gas or a suction pump.

7. The airway visualization system of claim 3 wherein the microcontroller is configured to output an image triggering signal.

8. The airway visualization system of claim 1 further comprising an imaging system in communication with the controller.

9. The airway visualization system of claim 8 wherein the imaging system comprises an x-ray imager.

10. The airway visualization system of claim 8 wherein the controller is configured to trigger or gate the imaging system with the pressure change.

11. The airway visualization system of claim 1 wherein the controller is configured to manipulate the fluid flow at a frequency of between 0.5 to 50 Hz.

12. The airway visualization system of claim 1 wherein the controller is configured to manipulate the fluid flow to have a pressure change of between 1 to 50 cmH2O or between −1 and −150 cmH2O.

13. The airway visualization system of claim 1 further comprising a vibrational component in communication with the delivery sheath and configured to vibrationally conduct to the airway.

14. A method of visualizing an airway within a subject, comprising:
positioning a delivery sheath through at least a portion of the airway and into proximity to a tissue region of interest within a lung;
manipulating a fluid flow through at least one lumen of the delivery sheath such that a pressure change is imparted within the airway sufficient to at least partially manipulate a diameter of the airway to reconfigure between an open resting configuration and a collapsed configuration such that a change in density of the airway is imparted while a remainder of the lung remains unaffected; and
obtaining an image of the airway via an imager while the position of the airway is manipulated.

15. The method of claim 14 further comprising:
obtaining a baseline image of the airway via the imager prior to manipulating the fluid flow;
obtaining a target image of the airway via the imager while the position of the airway is manipulated; and
digitally subtracting the target image from the baseline image to obtain a visual representation of the airway.

16. The method of claim 14 wherein positioning the delivery sheath further comprises fluidly isolating the airway.

17. The method of claim 14 wherein manipulating the fluid flow comprises infusing a fluid at a positive pressure through the at least one lumen to at least partially expand the airway.

18. The method of claim 17 further comprising suctioning the fluid from the airway to at least partially collapse the airway.

19. The method of claim 14 wherein manipulating the fluid flow comprises suctioning a fluid from the airway at a negative pressure through the at least one lumen to at least partially collapse the airway.

20. The method of claim 19 further comprising infusing the fluid at a positive pressure through the at least one lumen to at least partially expand the airway.

21. The method of claim 14 wherein obtaining the image of the airway comprises imaging the airway at a rate detectable by the imager.

22. The method of claim 21 wherein an imager frame rate is at least twice a frequency of pressure change.

23. The method of claim 14 wherein manipulating the fluid flow comprises manipulating the pressure change at a frequency of between 0.5 to 50 Hz.

24. The method of claim 14 wherein manipulating the fluid flow comprises imparting a positive pressure to the airway of between 1 to 50 cmH2O.

25. The method of claim 14 wherein manipulating the fluid flow comprises imparting a negative pressure to the airway of between −1 and −150 cmH2O.

26. The method of claim 14 wherein obtaining the image comprises obtaining an x-ray image of the airway.

27. The method of claim 14 wherein obtaining the image comprises timing the image to correspond to the manipulation of the fluid flow.

28. The method of claim 14 wherein obtaining the image comprises gating when the image is obtained to correspond to a physical parameter of the subject.

29. The method of claim 14 further comprising superimposing the visual representation of the airway upon a real-time image of the airway.

30. A method of visualizing an airway within a subject, comprising:

positioning a delivery sheath through at least a portion of the airway and into proximity to a tissue region of interest;

obtaining a baseline image of the airway via an imager;

manipulating a fluid flow through at least one lumen of the delivery sheath such that a pressure change is imparted within the airway sufficient to at least partially expand or collapse the airway such that a diameter of the airway is reconfigured to impart a change in density of the airway at a rate detectable by the imager;

obtaining a target image of the airway via the imager; and digitally subtracting the target image from the baseline image to obtain a visual representation of the airway.

31. An airway visualization system, comprising:

a delivery sheath having a length and defining at least one lumen therethrough, wherein the length is positionable within an airway of a subject; and a controller in communication with the delivery sheath, wherein the controller is configured to manipulate a fluid flow through the at least one lumen whereby an alternating pressure change is imparted within the airway of the subject to reconfigure a diameter of the airway between a first diameter configuration and a collapsed second configuration to correspondingly alter a density of the airway for visualization.

32. The airway visualization system of claim 31 further comprising an isolation component positioned near or at a distal end of the delivery sheath and expandable to at least partially obstruct the airway.

33. The airway visualization system of claim 31 wherein the controller comprises a microcontroller in communication with the delivery sheath.

34. The airway visualization system of claim 33 further comprising a pressure sensor configured to monitor a pressure within the airway and in communication with the microcontroller.

35. The airway visualization system of claim 33 wherein the controller further comprises a fluid pump or suction pump in communication with the microcontroller.

36. The airway visualization system of claim 33 wherein the controller further comprises one or more valves in communication with the microcontroller and also in fluid communication with an external source of gas or a suction pump.

37. The airway visualization system of claim 33 wherein the microcontroller is configured to output an image triggering signal.

38. The airway visualization system of claim 31 further comprising an imaging system in communication with the controller.

39. The airway visualization system of claim 38 wherein the imaging system comprises an x-ray imager.

40. The airway visualization system of claim 38 wherein the controller is configured to trigger or gate the imaging system with the pressure change.

41. The airway visualization system of claim 31 wherein the controller is configured to manipulate the fluid flow at a frequency of between 0.5 to 50 Hz.

42. The airway visualization system of claim 31 wherein the controller is configured to manipulate the fluid flow to have a pressure change of between −10 to 30 cmH2O.

43. The airway visualization system of claim 31 wherein the controller is configured to manipulate the fluid flow to have a pressure change of between 0 to 30 cmH2O.

44. The airway visualization system of claim 31 wherein the controller is configured to manipulate the fluid flow to have a pressure change of between −30 to 0 cmH2O.

45. The airway visualization system of claim 31 further comprising a vibrational component in communication with the delivery sheath and configured to vibrationally conduct to the airway.

46. A method of visualizing an airway within a subject, comprising:

positioning a delivery sheath through at least a portion of the airway and into proximity to a tissue region of interest within a lung;

manipulating a fluid flow through at least one lumen of the delivery sheath such that an alternating pressure change is imparted within the airway;

altering a diameter of the airway to reconfigure between a first diameter and a collapsed second diameter such that a change in density of the airway is imparted corresponding to the alternating pressure change; and visualizing the airway via an imager.

47. The method of claim 46 wherein visualizing the airway comprises:

obtaining a baseline image of the airway via the imager prior to manipulating the fluid flow;

obtaining a target image of the airway via the imager while the position of the airway is manipulated; and digitally subtracting the target image from the baseline image to obtain a visual representation of the airway.

48. The method of claim 46 wherein positioning the delivery sheath further comprises fluidly isolating the airway.

49. The method of claim 46 wherein manipulating the fluid flow comprises infusing a fluid at a positive pressure through the at least one lumen to at least partially expand the airway.

50. The method of claim 49 further comprising suctioning the fluid from the airway to at least partially collapse the airway.

51. The method of claim 50 wherein infusing the fluid comprises infusing the fluid at a pressure of 30 cmH2O and suctioning the fluid at a pressure of −10 cmH2O.

52. The method of claim 50 wherein infusing the fluid comprises infusing the fluid at a pressure of 30 cmH2O and suctioning the fluid at a pressure of 0 cmH2O.

53. The method of claim 50 wherein infusing the fluid comprises infusing the fluid at a pressure of 0 cmH2O and suctioning the fluid at a pressure of −30 cmH2O.

54. The method of claim 46 wherein visualizing the airway comprises imaging the airway at a rate detectable by the imager.

55. The method of claim 54 wherein an imager frame rate is at least twice a frequency of pressure change.

56. The method of claim 46 wherein visualizing the airway comprises obtaining an x-ray image of the airway.

57. The method of claim 46 wherein visualizing the airway comprises timing the image to correspond to the manipulation of the fluid flow.

58. The method of claim 46 wherein visualizing the airway comprises gating when the image is obtained to correspond to a physical parameter of the subject.

59. The method of claim 46 further comprising superimposing a visual representation of the airway upon a real-time image of the airway.

60. A method of altering a density of tissue within a subject, comprising:

positioning a delivery sheath through at least a portion of the airways and into proximity to one or more structures of interest within a lung;

manipulating a fluid flow through at least one lumen of the delivery sheath such that an alternating pressure change is imparted within the airways;

altering a diameter of the airways to reconfigure between a first diameter and a collapsed second diameter such that the density of the airways is altered corresponding to the alternating pressure change, wherein the airways are in proximity to the one or more structures of interest; and visualizing the one or more structures of interest based on the airways in proximity to the one or more structures of interest via an imager.

61. The method of claim 60 wherein visualizing the one or more structures comprises:

obtaining a baseline image of the airways in proximity to the one or more structures of interest via the imager prior to manipulating the fluid flow;

obtaining a target image of the airways in proximity to the one or more structures of interest via the imager while the position of the airways is manipulated; and digitally subtracting the target image from the baseline image to obtain a visual representation of the one or more structures.

62. The method of claim 60 wherein positioning the delivery sheath further comprises fluidly isolating the airway.

63. The method of claim 60 wherein manipulating the fluid flow comprises infusing a fluid at a positive pressure through the at least one lumen to at least partially expand the airway.

64. The method of claim 63 further comprising suctioning the fluid from the airway to at least partially collapse the airway.

65. The method of claim 64 wherein infusing the fluid comprises infusing the fluid at a pressure of 30 cmH2O and suctioning the fluid at a pressure of −10 cmH2O.

66. The method of claim 64 wherein infusing the fluid comprises infusing the fluid at a pressure of 30 cmH2O and suctioning the fluid at a pressure of 0 cmH2O.

67. The method of claim 64 wherein infusing the fluid comprises infusing the fluid at a pressure of 0 cmH2O and suctioning the fluid at a pressure of −30 cmH2O.

68. The method of claim 60 wherein visualizing the one or more structures comprises imaging the airways at a rate detectable by the imager.

69. The method of claim 68 wherein an imager frame rate is at least twice a frequency of pressure change.

70. The method of claim 60 wherein visualizing the one or more structures comprises obtaining an x-ray image of one or more nodules.

71. The method of claim 60 wherein visualizing the one or more structures comprises timing the image to correspond to the manipulation of the fluid flow.

72. The method of claim 60 wherein visualizing the one or more structures comprises gating when the image is obtained to correspond to a physical parameter of the subject.

73. The method of claim 60 further comprising superimposing a visual representation of the one or more structures upon a real-time image of the one or more structures.

74. A method of visualizing a tissue region of interest within a subject, comprising:

positioning a delivery sheath through at least a portion of the airway and into proximity to the tissue region of interest within a lung;

contacting a tissue wall of the airway with a portion of the delivery sheath;

conducting a vibration from the portion of the delivery sheath and into the tissue wall such that the vibration is transmitted to the tissue region of interest;

altering a density of the tissue region of interest between a first density and a second density such that a change in the density is imparted to the tissue region of interest via the vibration; and visualizing the tissue region of interest via an imager.

75. The method of claim 74 wherein visualizing the tissue region of interest comprises:

obtaining a baseline image of the tissue region of interest via the imager prior to conducting the vibration;

obtaining a target image of the tissue region of interest via the imager while the position of the tissue region of interest is manipulated; and digitally subtracting the target image from the baseline image to obtain a visual representation of the tissue region of interest.

76. The method of claim 74 wherein visualizing the tissue region of interest comprises imaging at least the portion of the airway.

77. The method of claim 74 wherein visualizing the tissue region of interest comprises imaging one or more nodules within the lung.

78. The method of claim 74 wherein conducting the vibration comprises imparting the vibration at a frequency of 0.5 to 50 Hz.

79. The method of claim 74 wherein visualizing the tissue region of interest comprises imaging the airway at a rate detectable by the imager.

80. The method of claim 79 wherein an imager frame rate is at least twice a frequency of the vibration.

81. The method of claim 74 wherein visualizing the tissue region of interest comprises obtaining an x-ray image of the tissue region of interest.

82. The method of claim 74 wherein visualizing the tissue region of interest comprises gating when the image is obtained to correspond to a physical parameter of the subject.

83. The method of claim 74 further comprising superimposing a visual representation of the tissue region of interest upon a real-time image of the tissue region of interest.

* * * * *